(12) United States Patent
Chen et al.

(10) Patent No.: US 9,174,989 B2
(45) Date of Patent: Nov. 3, 2015

(54) PROCESS FOR MAKING CGRP RECEPTOR ANTAGONISTS

(71) Applicant: Merck Sharp & Dohme Corp., Rahway, NJ (US)

(72) Inventors: Frank Chen, Plainsboro, NJ (US); Carmela Molinaro, Colonia, NJ (US); W. Peter Wuelfing, Harleysville, PA (US); Nobuyoshi Yasuda, Mountainside, NJ (US); Jianguo Yin, Plainsboro, NJ (US); Yong-Li Zhong, Edison, NJ (US); Joseph Lynch, Plainsboro, NJ (US); Teresa Andreani, Matawan, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/399,483

(22) PCT Filed: Mar. 12, 2013

(86) PCT No.: PCT/US2013/030692
§ 371 (c)(1),
(2) Date: Nov. 6, 2014

(87) PCT Pub. No.: WO2013/169348
PCT Pub. Date: Nov. 14, 2013

(65) Prior Publication Data
US 2015/0112067 A1 Apr. 23, 2015

Related U.S. Application Data

(60) Provisional application No. 61/644,631, filed on May 9, 2012.

(51) Int. Cl.
| | | |
|---|---|---|
| C07D 471/20 | (2006.01) |
| C07D 209/42 | (2006.01) |
| C07D 417/04 | (2006.01) |
| C07D 471/10 | (2006.01) |
| C07C 57/38 | (2006.01) |
| C07C 59/245 | (2006.01) |
| C07C 63/04 | (2006.01) |
| C07C 205/57 | (2006.01) |
| C07C 233/47 | (2006.01) |
| C07D 211/76 | (2006.01) |

(52) U.S. Cl.
CPC ............ *C07D 471/20* (2013.01); *C07C 57/38* (2013.01); *C07C 59/245* (2013.01); *C07C 63/04* (2013.01); *C07C 205/57* (2013.01); *C07C 233/47* (2013.01); *C07D 209/42* (2013.01); *C07D 211/76* (2013.01); *C07D 417/04* (2013.01); *C07D 471/10* (2013.01); *C07B 2200/13* (2013.01)

(58) Field of Classification Search
CPC ... C07D 471/20; C07D 471/04; C07D 471/10
USPC .................................................. 546/15, 201
See application file for complete search history.

(56) References Cited

U.S. PATENT DOCUMENTS

| | | | |
|---|---|---|---|
| 7,390,798 B2 | 6/2008 | Williams et al. |
| 2009/0054408 A1 | 2/2009 | Bell et al. |
| 2010/0160334 A1 | 6/2010 | Bell et al. |
| 2010/0179166 A1 | 7/2010 | Bell et al. |
| 2012/0122899 A1 | 5/2012 | Bell et al. |
| 2012/0122900 A1 | 5/2012 | Bell et al. |
| 2012/0122911 A1 | 5/2012 | Bell et al. |

*Primary Examiner* — Rita Desai
(74) *Attorney, Agent, or Firm* — H. Eric Fischer; John C. Todaro

(57) ABSTRACT

The disclosure encompasses a novel process for making piperidinone carboxamide indane and azainane derivatives, having less steps and improved yields as compared to previous synthetic methods for making these compounds, which are CGRP receptor antagonists, useful for the treatment of migraine. Conditions for an amide bond formation between an acid and amine include for example reacting the compounds of Formulae B (after salt break) and C with an amide coupling reagent and optionally an additive and an acid and/or a base in a non-reactive solvent.

11 Claims, 17 Drawing Sheets

SEQUENCE LISTING

```
<160> NUMBER OF SEQ ID NOS: 2

<210> SEQ ID NO 1
<211> LENGTH: 330
<212> TYPE: PRT
<213> ORGANISM: Artificial Sequence
<220> FEATURE:
<223> OTHER INFORMATION: Engineered variant of Arthrobacter transaminase

<400> SEQUENCE: 1
```

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Trp Val Ala Ile Thr
        115                 120                 125

Arg Gly Tyr Ser Ser Thr Pro Leu Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Ala
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

```
Tyr Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
        290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 2
<211> LENGTH: 990
<212> TYPE: DNA
<213> ORGANISM: Artificial Sequence
<220> FEATURE:
<223> OTHER INFORMATION: Engineered variant of Arthrobacter transaminase

<400> SEQUENCE: 2
atggcgttct cagcggacac ccctgaaatc gtttacaccc cgacaccgg tctggactat      60 atcacctact ctgactacga actggacccg gctaacccgc tggctggtgg tgctgcttgg    120
atcgaaggtg ctttcgttcc gccgtctgaa gctcgtatct ctatcttcga ccagggtttt   180
tatacttctg acgctaccta caccgtcttc cacgtttgga acggtaacgc tttccgtctg   240
ggggaccaca tcgaacgtct gttctctaat gcggaatcta ttcgtttgat cccgccgctg   300
acccaggacg aagttaaaga gatcgctctg gaactggttg ctaaaaccga actgcgtgaa   360
gcgattgttt gggttgcaat cacccgtggt tactcttcta ccccattgga gcgtgacatc   420
accaaacatc gtccgcaggt ttacatgtat gctgttccgt accagtggat cgtaccgttt   480
gaccgcatcc gtgacggtgt tcacctgatg gttgctcagt cagttcgtcg tacaccgcgt   540
agctctatcg acccgcaggt taaaaacttc caggcaggtg acctgatccg tgcaattcag   600
gaaacccacg accgtggttt cgagttaccg ctgctgctgg actgcgacaa cctgctggct   660
gaaggtccgg gtttcaacgt tgttgttatc aaagacggtg ttgttcgttc tccgggtcgt   720
gctgctctgc cgggtatcac ccgtaaaacc gttctggaaa tcgctgaatc tctgggtcac   780
gaagctatcc tggctgacat caccccggct gaactgtacg acgctgacga agttctgggt   840
tgctcaaccg cgggtggtgt ttggccgttc gtttctgttg acggtaactc tatctctgac   900
ggtgttccgg gtccggttac ccagtctatc atccgtcgtt actgggaact gaacgttgaa   960
ccttcttctc tgctgacccc ggtacagtac                                    990
```

PROCESS FOR MAKING CGRP RECEPTOR ANTAGONISTS

REFERENCE TO SEQUENCE LISTING

The official copy of the Sequence Listing is submitted concurrently with the specification as an ASCII formatted text file via EFS-Web, with a file name of "23236USPSP-SEQLIST-09MAY2012", a creation date of May 9, 2012, and a size of 4,509 bytes. The Sequence Listing filed via EFS-Web is part of the Specification and is incorporated in its entirety by reference herein.

BACKGROUND OF THE INVENTION

This invention relates to a process for making piperidinone carboxamide indane and azainane derivatives, which are CGRP receptor antagonists useful for the treatment of migraine. This class of compounds is described in U.S. patent application Ser. No. 13/293,166 filed Nov. 10, 2011, Ser. No. 13/293,177 filed Nov. 10, 2011 and Ser. No. 13/293,186 filed Nov. 10, 2011, and PCT International Application Nos. PCT/US11/60081 filed Nov. 10, 2011 and PCT/US11/60083 filed Nov. 10, 2011.

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention describes a novel process for making piperidinone carboxamide indane and azainane derivatives, which are CGRP receptor antagonists, having less steps and improved yields as compared to previous synthetic methods for making these compounds.

SUMMARY OF THE INVENTION

The invention encompasses a novel process for making piperidinone carboxamide indane and azainane derivatives, which are CGRP receptor antagonists useful for the treatment of migraine.

BRIEF DESCRIPTION OF THE DRAWINGS

The invention is described in connection with the appended drawings in which.

DETAILED DESCRIPTION OF THE INVENTION

Figure 1:
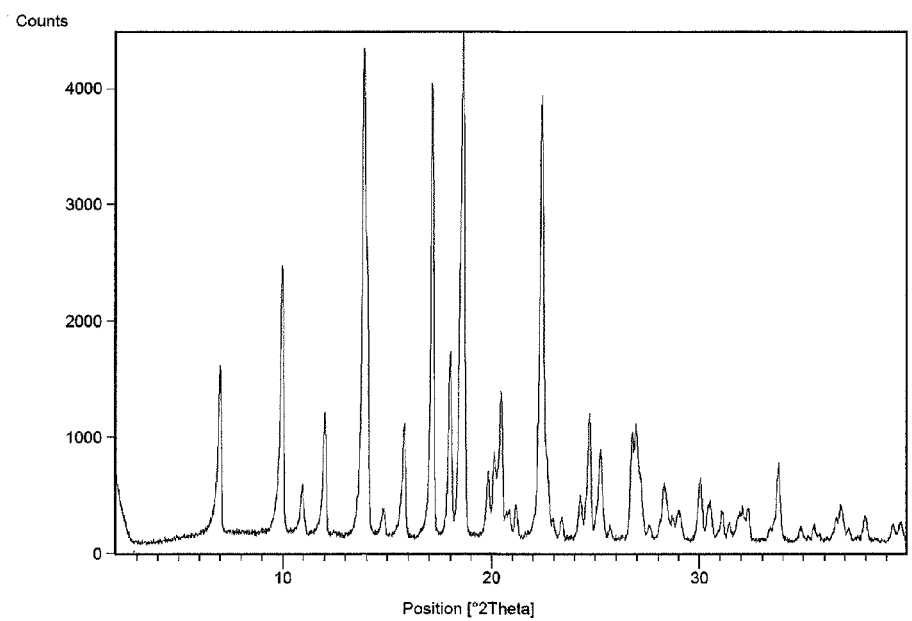
FIG. 1 is the X-ray powder diffraction (XRPD) pattern for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate.

The invention encompasses a process for making a compound of Formula I

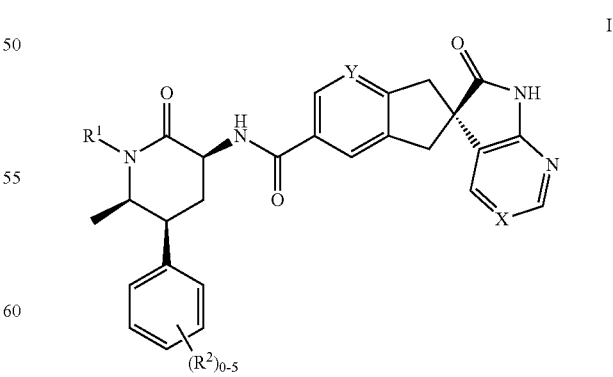

or a pharmaceutically acceptable salt thereof, wherein:

X is selected from —C($R^3$)═ or —N═, wherein $R^3$ is hydrogen, F or CN;

Y is CH or N;
R¹ is selected from the group consisting of: $C_{1-4}$alkyl, cyclopropylmethyl, cyclobutylmethyl and [1-(trifluoromethyl)cyclopropyl]methyl, each of which is optionally substituted with one or more substituents as allowed by valence independently selected from the group consisting of: F and hydroxy; and
R² is selected from hydrogen, methyl, F, Cl, or Br; comprising crystallizing the Formula A

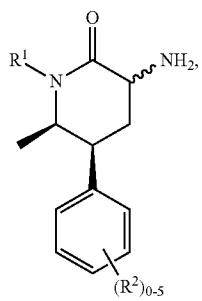

A in the presence of an arylaldehyde derivative and a first acid in a first organic solvent to yield the compound of Formula B

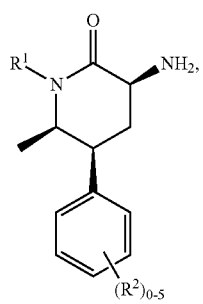

B optionally as a salt, and coupling the compound of Formula B with a compound of Formula C

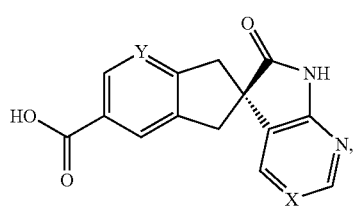

C or a salt thereof, under conditions for an amide bond formation between an acid and an amine to yield a compound of Formula I.

Conditions for an amide bond formation between an acid and amine include for example reacting the compounds of Formulas B (after salt break) and C with an amide coupling reagent and optionally an additive and an acid and/or a base in a non-reactive solvent. Amide coupling reagents include, for example, EDC, CDI, $SOCl_2$, $(COCl)_2$, DCC, T3P® (propane phosphonic acid anhydrie), DPPA, and the like. Additives include HOBT, HOAt, HATU, HOPO, and HOSu, pyridine, pyridine derivatives and the like. Appropriate bases include amines having formula $N(R)_3$, wherein each R is independently hydrogen, alkyl and aryl, inorganic bases, such as sodium hydroxide, lithium hydroxide, potassium hydroxide, sodium carbonate, sodium bicarbonate, potassium carbonate, potassium bicarbonate, lithium carbonate, lithium carbonate, cesium carbonate, potassium phosphate, and the like. Conditions for an amide bond formation between an acid and amine also include utilizing acyl halides via mixed carbonic anhydride intermediates. Examples include pivaloyl chloride, alkyl chloroformate plus a base. Further examples of peptide coupling reagents in organic synthesis are well known in the art and described for example in Han, et al., Tetrahedron 60 (2004) 2447-2467.

In an embodiment, the compound of Formula B is coupled with a compound of Formula C after salt break by reacting the reagents with an amide coupling reagent and, optionally an amide coupling reagent additive, in a non-reactive solvent to yield a compound of Formula I. In another embodiment, the coupling reagent is selected from EDC, HATU, T3P®, CDI, the amide coupling reagent additive is HOBT or HOPO and the non-reactive solvent is an organic/aqueous mixture selected from DCM/water, iPAC/water, acetonitrile/water, acetone/water, iPA/water, EtOH/water, MeOH/water, acetone/water and THF/water.

In another embodiment of the invention, a salt of a compound of Formula C is coupled to the compound of Formula B. Salts encompassed within the invention include sodium hydroxide, potassium hydroxide, lithium hydroxide, and corresponding carbonate and bicarbonate.

In another embodiment of the invention, the arylaldehyde derivative is selected from 2-hydroxybenzaldehyde, substituted 2-hydroxybenzaldehyde, such as 2-hydroxy-5-nitrobenzaldehyde and 2-hydroxy-3,5-dichlorobenzaldehyde.

"First organic solvent" means any organic solvent appropriate for the reaction such as THF, Me-THF, MTBE and the like. The term "first acid" means for example HCl, $MeSO_3H$, $H_2SO_4$, p-toluenesulfonic acid and the like. Selection of the appropriate solvent and acid is well within the skill of one having ordinary skill in the art.

Another embodiment of the invention encompasses the process described above further comprising making the compound of Formula A by reacting a compound of Formula D

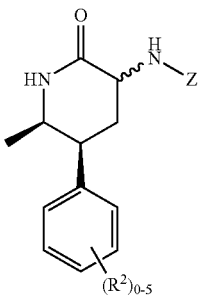

D wherein Z is an amine protecting group, with an electrophilic alkylating agent that delivers a cationic R¹, such as R¹—OS$(O)_2CF_3$ or R¹—OS$(O)_2$F, in the presence of base and optionally an additive in a second organic solvent to yield a compound of Formula E

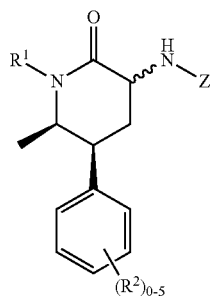

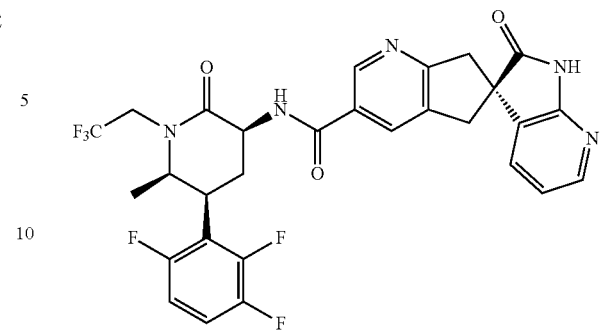

and having the following chemical name: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate.

X-ray powder diffraction studies are widely used to characterize molecular structures, crystallinity, and polymorphism. The X-ray powder diffraction patterns disclosed herein were generated on a Philips Analytical X'Pert PRO X-ray Diffraction System with PW3040/60 console. A PW3373/00 ceramic Cu LEF X-ray tube K-Alpha radiation was used as the source.

FIG. 1 shows the X-ray powder diffraction pattern for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate. The monohydrate form is characterized by diffraction peaks corresponding to d-spacings as detailed in Table 1.

and deprotecting the compound of Formula E to yield a compound of Formula A.

Appropriate amine protecting groups that can be used in the present invention include for example, Boc, Cbz, =C(Ph)$_2$, =CHPh, and the like. Bases that may be used in the present invention include alkali metal bases, preferably lithium base, such as lithium tert-butoxide, lithium tert-pentoxide. Optional additives are, for example, aprotic polar solvents, such as DMPU, DMAc and DMF. The term second organic solvent includes THF, Me-THF, MTBE, and the like. The terms also include mixtures of solvents.

Deprotection can be carried out under acidic conditions, for example using a second acid including but not limited to HCl, MeSO$_3$H, H$_2$SO$_4$, p-toluenesulfonic acid and the like, hydrogenation conditions or basic conditions as appropriate.

In another embodiment of the invention, Z is t-butyl-O—C(O)—, the electrophilic alkylating agent is $R^1$—OS(O)$_2$CF$_3$ or $R^1$—OS(O)$_2$F, deprotection is effected by reacting the compound of Formula E with an acid, the lithium base is selected from LiOBu$^t$ and LiOPent$^t$, the additive is an aprotic polar solvent, and the second organic solvent is selected from THF, Me-THF and MTBE. In another embodiment of the invention, the second acid is selected from HCl, MeSO$_3$H, H$_2$SO$_4$, p-toluenesulfonic acid and benzenesulfonic acid.

The compound of Formula D described in the process above may be made by reacting a compound of Formula F

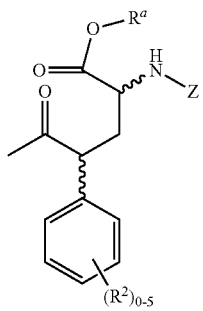

wherein R$^a$ is C$_{1-6}$ alkyl, with a transaminase enzyme having the amino acid sequence of SEQ ID NO: 1 and the nucleotide sequence of SEQ ID NO: 2 in an aqueous solvent mixture to yield a compound of Formula D. Under optimized conditions, the compound of Formula F is reacted with the transaminase enzyme of SEQ ID NO: 1 at a pH in the range of pH 10 to pH 10.7 and an elevated temperature in the range of 45° C. to 60° C. In another embodiment, the reaction is run at a pH of about 10.5 and a temperature of about 55° C.

Another embodiment of the invention encompasses crystalline monohydrate free base of the compound having the structure

TABLE 1

| Pos. [° Two Theta.] | d-spacing [Å] | Rel. Int. [%] |
| --- | --- | --- |
| 6.99 | 12.65 | 35 |
| 9.98 | 8.87 | 54 |
| 10.95 | 8.08 | 11 |
| 12.03 | 7.36 | 26 |
| 13.91 | 6.37 | 97 |
| 14.85 | 5.96 | 8 |
| 15.82 | 5.60 | 23 |
| 17.16 | 5.17 | 90 |
| 18.02 | 4.92 | 38 |
| 18.65 | 4.76 | 100 |
| 19.83 | 4.48 | 14 |
| 20.12 | 4.41 | 18 |
| 20.47 | 4.34 | 30 |
| 21.20 | 4.19 | 8 |
| 22.44 | 3.96 | 87 |
| 24.27 | 3.67 | 10 |
| 24.72 | 3.60 | 26 |
| 25.25 | 3.53 | 18 |
| 26.76 | 3.33 | 22 |
| 26.93 | 3.31 | 23 |
| 27.60 | 3.23 | 4 |
| 28.31 | 3.15 | 12 |
| 29.02 | 3.08 | 7 |
| 30.05 | 2.97 | 13 |
| 30.50 | 2.93 | 8 |
| 31.11 | 2.88 | 6 |
| 31.42 | 2.85 | 4 |
| 31.98 | 2.80 | 6 |
| 32.31 | 2.77 | 7 |
| 33.78 | 2.65 | 16 |
| 34.88 | 2.57 | 3 |

DSC data disclosed herein were acquired using TA Instruments DSC 2910 or equivalent instrumentation. A sample with a weight between 2 and 8 mg was weighed into a pan and the pan was crimped and a pinhole placed in the lid. This pan was placed in the sample position in the calorimeter cell. An empty pan was placed in the reference position. The calorimeter cell was closed and a flow of nitrogen is passed through the cell. The heating program was set to heat the sample at a heating rate of 10° C./min to a temperature of approximately 300° C. When the run was completed, the data were analyzed using the DSC analysis program in the system software. The observed endotherms were integrated between baseline temperature points that are above and below the temperature range over which the endotherm is observed. The data reported are the onset temperature, peak temperature and enthalpy.

Figure 2:
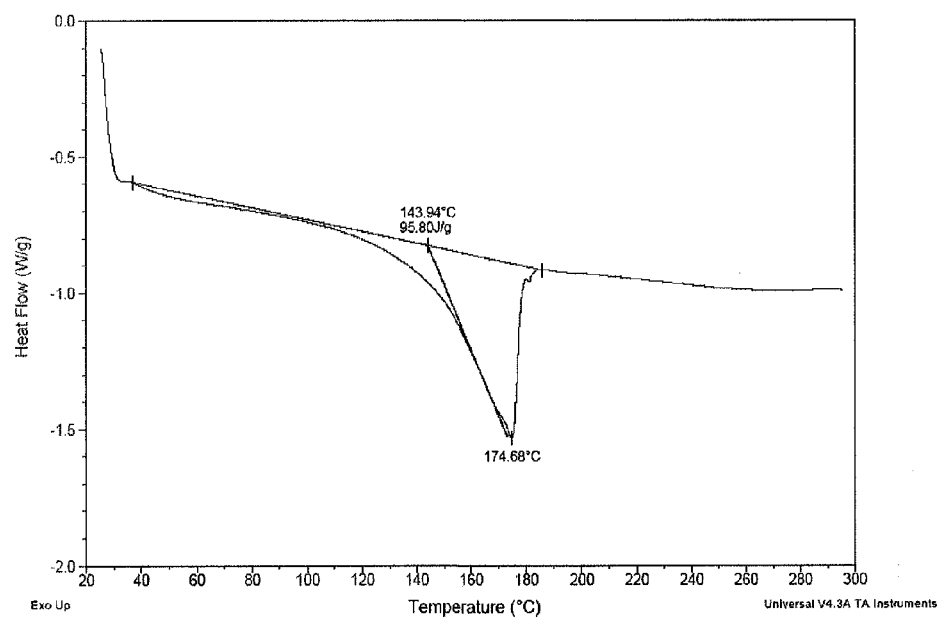
FIG. 2 is the differential scanning calorimetry (DSC) thermogram for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate.

FIG. 2 shows the DSC thermogram for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate. A broad endotherm with $T_{onset}$=143.9 C, $T_{peak}$=174.7 C, and $\Delta H$=95.8 J/g is observed which is attributable to a dehydration event.

An embodiment of the invention encompasses crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate having a DSC extrapolated onset melting temperature of about 144° C. and a DSC peak melting temperature of about 175° C. Another embodiment of the invention encompasses crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate having d-spacings determined by x-ray powder diffraction, Cu K alpha, of about 12.7, 8.9, 8.1, 7.4, 6.4, 5.2, 4.9, 4.8 and 4.0 angstroms.

Figure 3:
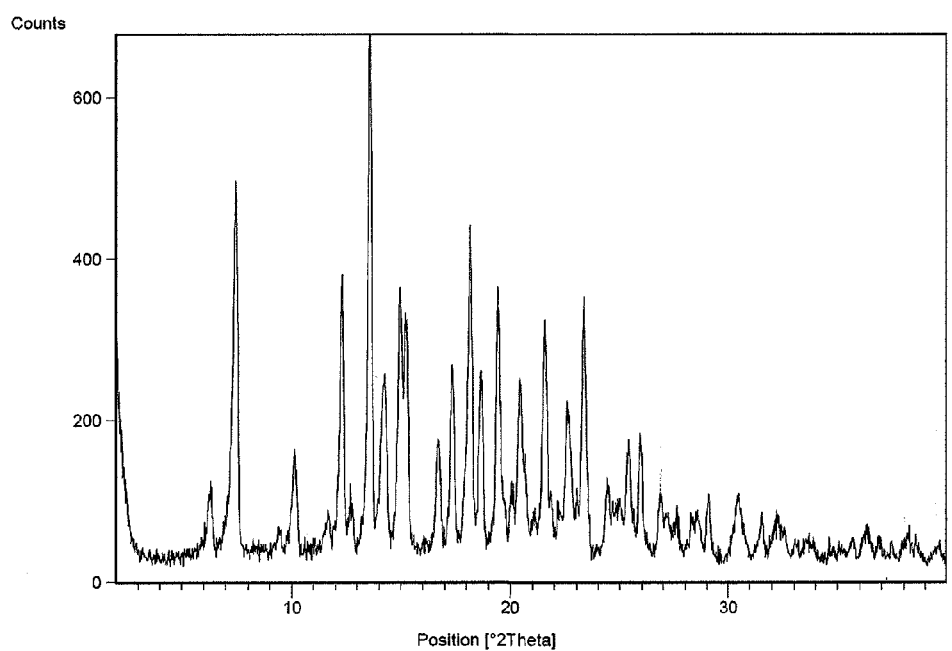
FIG. 3 is the XRPD pattern for (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide trihydrate.

FIG. 3 shows the X-ray powder diffraction pattern of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide trihydrate, The trihydrate form is characterized by diffraction peaks corresponding to d-spacings as detailed in Table 2.

TABLE 2

| Pos. [° Two Theta.] | d-spacing [Å] | Rel. Int. [%] |
|---|---|---|
| 6.27 | 14.09 | 11 |
| 7.43 | 11.90 | 72 |
| 9.44 | 9.37 | 4 |
| 10.12 | 8.74 | 21 |
| 11.66 | 7.59 | 9 |
| 12.31 | 7.19 | 52 |
| 12.74 | 6.95 | 7 |
| 13.60 | 6.51 | 100 |
| 14.25 | 6.22 | 34 |
| 14.98 | 5.91 | 49 |
| 15.25 | 5.81 | 45 |
| 16.71 | 5.30 | 22 |
| 17.36 | 5.11 | 37 |
| 18.18 | 4.88 | 63 |
| 18.67 | 4.75 | 36 |
| 19.43 | 4.57 | 52 |
| 20.08 | 4.42 | 13 |
| 20.47 | 4.34 | 33 |
| 21.58 | 4.12 | 43 |
| 22.65 | 3.93 | 28 |
| 23.36 | 3.81 | 50 |
| 24.45 | 3.64 | 12 |
| 25.40 | 3.51 | 23 |
| 25.94 | 3.43 | 24 |

TABLE 2-continued

| Pos. [° Two Theta.] | d-spacing [Å] | Rel. Int. [%] |
|---|---|---|
| 26.90 | 3.31 | 12 |
| 28.30 | 3.15 | 12 |
| 28.53 | 3.13 | 13 |
| 29.09 | 3.07 | 17 |

Figure 4:
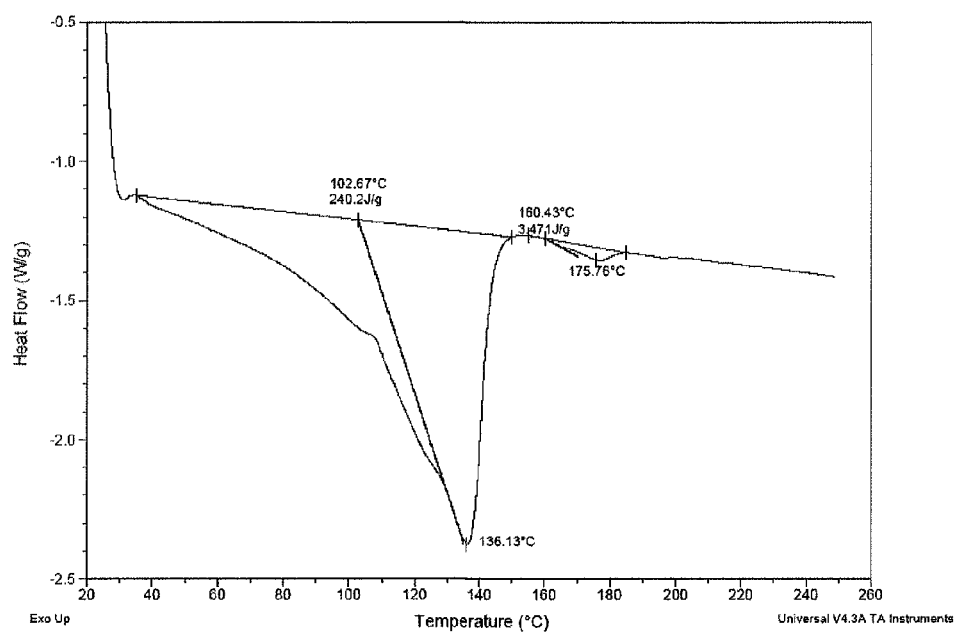
FIG. 4 is the DSC thermogram for (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3-pyrrolo[2,3-b]pyridine]-3-carboxamide trihydrate.

FIG. 4 shows the DSC thermogram for crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide trihydrate. A broad endotherm with extrapolated onset ($T_{onset}$)=102.7° C., $T_{peak}$=136.1° C., and $\Delta H$=240.2 J/g was observed that was consistent with a dehydration event. A small endotherm with extrapolated onset ($T_{onset}$)=160.4° C., $T_{peak}$=175.8° C., and $\Delta H$=3.47 J/g was observed that was consistent with a melt/collapse of a dehydrated form.

Another embodiment of the invention encompasses crystalline monohydrate free base of the compound having the structure

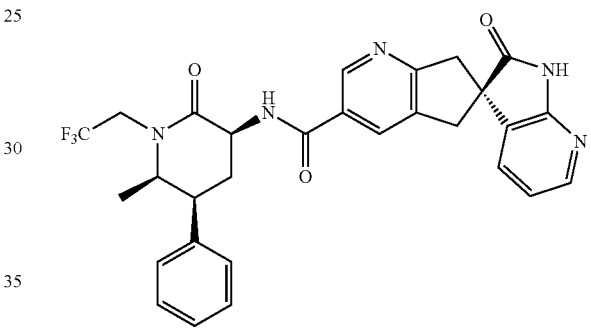

Figure 5:
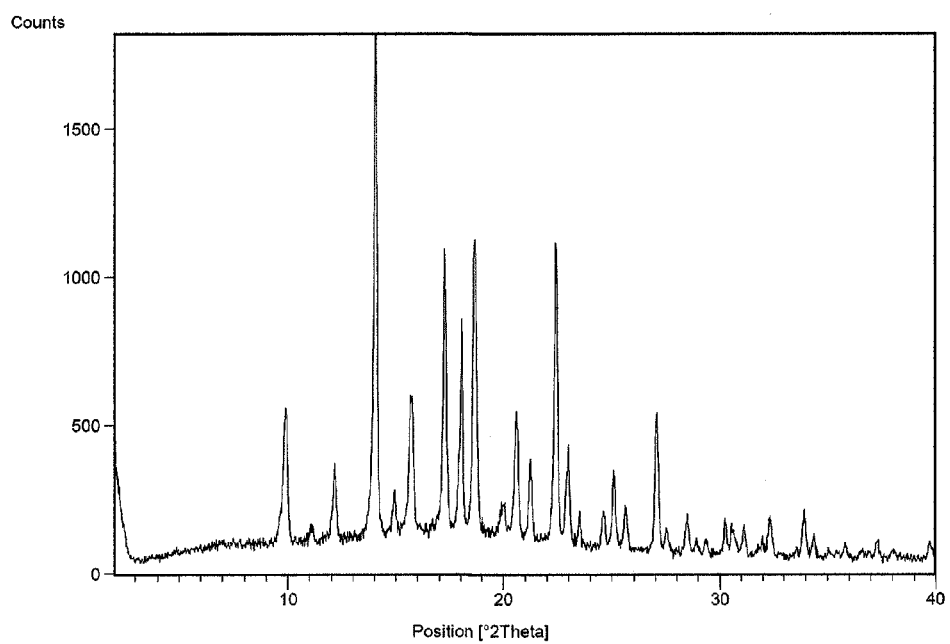
FIG. 5 is the XRPD of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3-pyrrolo[2,3-b]pyridine]-3-carboxamide monohydrate.

FIG. 5 shows the X-ray powder diffraction pattern of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide monohydrate. The monohydrate form is characterized by diffraction peaks corresponding to d-spacings as detailed in Table 3.

TABLE 3

| Pos. [° Two Theta.] | d-spacing [Å] | Rel. Int. [%] |
|---|---|---|
| 9.90 | 8.94 | 29 |
| 11.10 | 7.97 | 6 |
| 12.16 | 7.28 | 17 |
| 14.06 | 6.30 | 100 |
| 14.94 | 5.93 | 12 |
| 15.72 | 5.64 | 30 |
| 17.27 | 5.14 | 59 |
| 18.06 | 4.91 | 45 |
| 18.67 | 4.75 | 62 |
| 19.95 | 4.45 | 9 |
| 20.60 | 4.31 | 28 |
| 21.24 | 4.18 | 19 |
| 22.42 | 3.97 | 60 |
| 22.98 | 3.87 | 21 |
| 23.50 | 3.79 | 9 |
| 24.60 | 3.62 | 9 |
| 25.08 | 3.55 | 17 |
| 25.61 | 3.48 | 10 |
| 27.05 | 3.30 | 27 |
| 27.53 | 3.24 | 6 |
| 28.48 | 3.13 | 7 |

TABLE 3-continued

| Pos. [° Two Theta.] | d-spacing [Å] | Rel. Int. [%] |
| --- | --- | --- |
| 28.91 | 3.09 | 3 |
| 29.36 | 3.04 | 3 |
| 30.27 | 2.95 | 7 |
| 30.63 | 2.92 | 5 |
| 31.12 | 2.87 | 6 |
| 32.34 | 2.77 | 8 |
| 33.92 | 2.64 | 9 |
| 34.38 | 2.61 | 5 |

Figure 6:
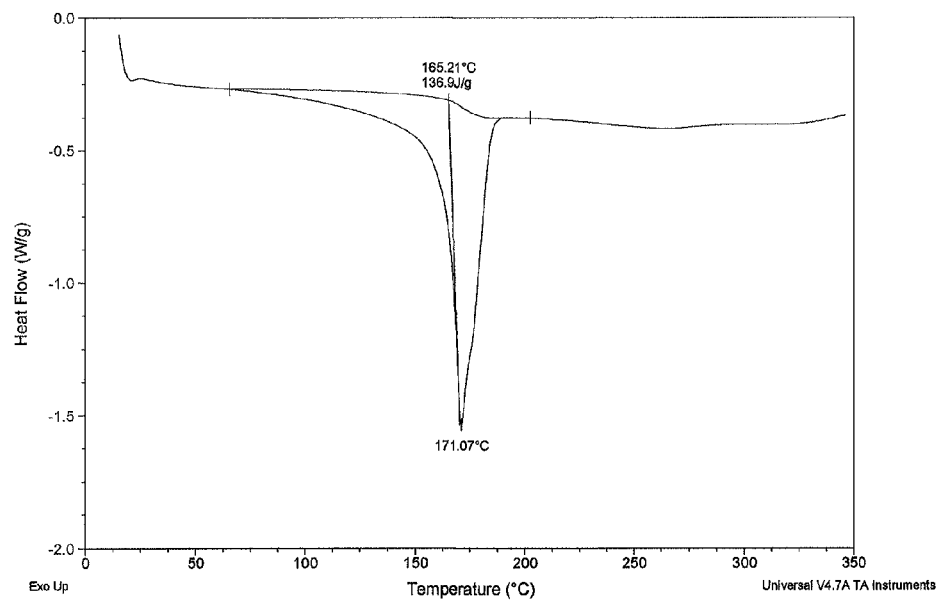
FIG. 6 is the DSC thermogram for crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide monohydrate.

FIG. 6 shows the DSC thermogram for crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide monohydrate. A melting endotherm coupled with dehydration was observed with an extrapolated onset ($T_{onset}$)=165.2° C., $T_{peak}$=171.1° C., and ΔH=136.9 J/g.

An embodiment of the invention encompasses crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide monohydrate having a DSC extrapolated onset melting/dehydration temperature of about 165° C. and a DSC peak melting temperature of about 171° C. Another embodiment of the invention encompasses crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide monohydrate having d-spacings determined by x-ray powder diffraction, Cu K alpha, of about 8.9, 8.0, 7.3, 6.3, 5.9, 5.6, 5.1, 4.9, 4.8, 4.5 and 4.3 angstroms.

Another embodiment of the invention encompasses crystalline trihydrate free base of the compound having the structure

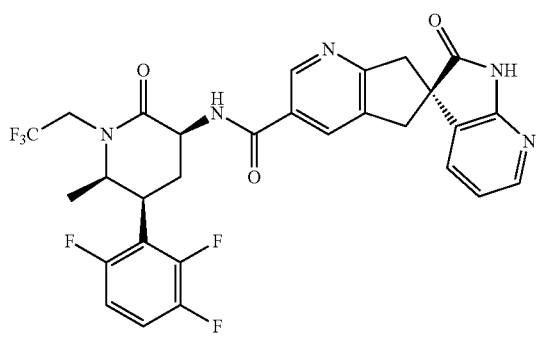 [SMILES: C[C@@H]1[C@H](c2c(F)ccc(F)c2F)C[C@H](NC(=O)c2cnc3c(c2)C[C@@]2(C3)C(=O)Nc3ncccc32)C(=O)N1CC(F)(F)F]

and having the following chemical name: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide trihydrate.

Figure 7:
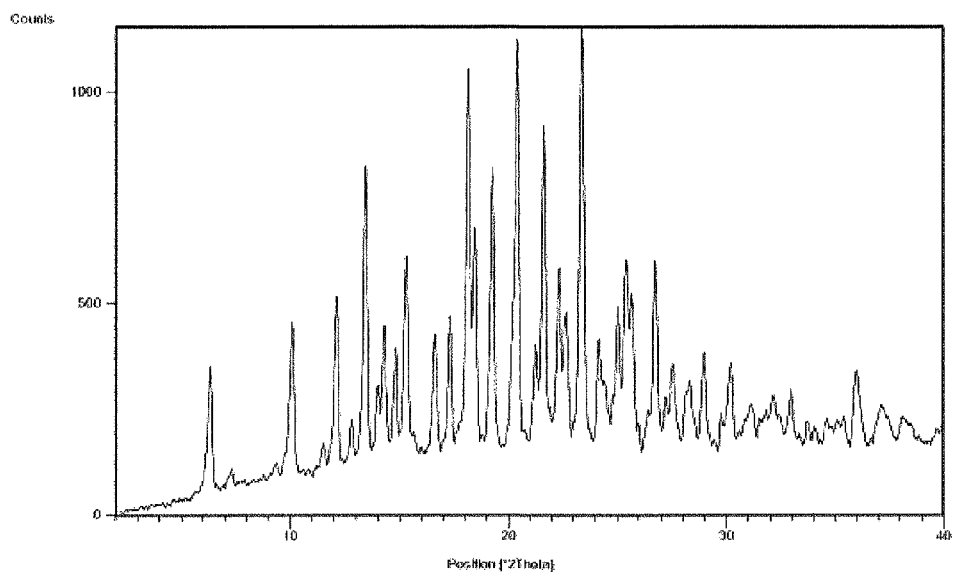
FIG. 7 is the X-ray powder diffraction (XRPD) pattern for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide trihydrate.

FIG. 7 shows the X-ray powder diffraction pattern for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide trihydrate. The trihydrate form is characterized by diffraction peaks corresponding to d-spacings as detailed in Table 4.

TABLE 4

| Pos. [° Two Theta.] | d-spacing [Å] | Rel. Int. [%] |
| --- | --- | --- |
| 6.34 | 13.95 | 30 |
| 7.32 | 12.07 | 5 |
| 9.36 | 9.45 | 5 |
| 10.10 | 8.76 | 38 |
| 11.52 | 7.68 | 8 |
| 12.11 | 7.31 | 42 |
| 12.81 | 6.91 | 12 |
| 13.44 | 6.59 | 70 |
| 14.00 | 6.33 | 19 |
| 14.29 | 6.20 | 33 |
| 14.79 | 5.99 | 27 |
| 15.29 | 5.79 | 49 |
| 15.63 | 5.67 | 8 |
| 16.59 | 5.34 | 31 |
| 17.27 | 5.13 | 34 |
| 18.13 | 4.89 | 91 |
| 18.43 | 4.81 | 54 |
| 19.25 | 4.61 | 68 |
| 20.41 | 4.35 | 96 |
| 21.26 | 4.18 | 26 |
| 21.64 | 4.11 | 77 |
| 22.34 | 3.98 | 43 |
| 22.65 | 3.93 | 33 |
| 23.39 | 3.80 | 100 |
| 24.18 | 3.68 | 27 |
| 24.44 | 3.64 | 17 |
| 24.90 | 3.58 | 16 |
| 25.04 | 3.56 | 35 |
| 25.44 | 3.50 | 46 |
| 25.67 | 3.47 | 38 |
| 26.74 | 3.33 | 46 |
| 27.22 | 3.28 | 14 |
| 27.52 | 3.24 | 22 |
| 28.31 | 3.15 | 18 |
| 28.96 | 3.08 | 25 |
| 29.76 | 3.00 | 11 |
| 30.19 | 2.96 | 22 |
| 31.10 | 2.88 | 12 |
| 32.15 | 2.78 | 14 |
| 32.41 | 2.76 | 9 |
| 32.96 | 2.72 | 16 |
| 33.71 | 2.66 | 9 |
| 34.04 | 2.63 | 8 |
| 35.98 | 2.50 | 20 |

Figure 8:
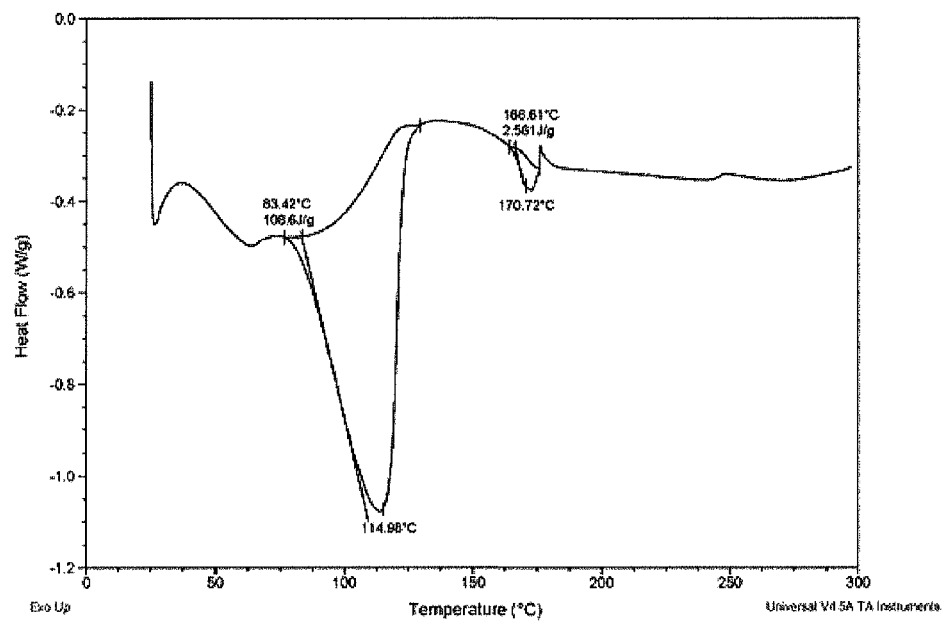
FIG. 8 is the differential scanning calorimetry (DSC) thermogram for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide trihydrate.

FIG. 8 shows the DSC thermogram for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide trihydrate. A broad endotherm with extrapolated onset ($T_{onset}$)=83.4° C., $T_{peak}$=115.0° C., and ΔH=108.6 J/g was observed that was consistent with a dehydration event. A small endotherm with extrapolated onset ($T_{onset}$)=166.6° C., $T_{peak}$=170.7° C., and ΔH=2.56 J/g was observed that was consistent with a melt/collapse of a dehydrated form.

Another embodiment of the invention encompasses crystalline methanol solvate free base of the compound having the structure

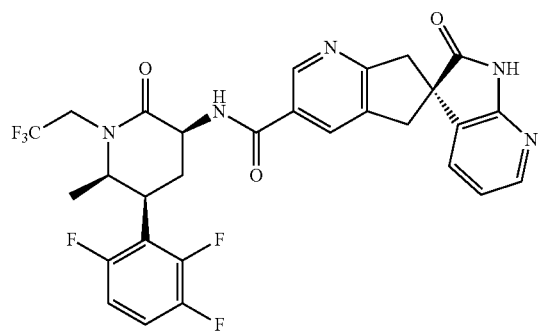 [SMILES: C[C@@H]1[C@H](c2c(F)ccc(F)c2F)C[C@H](NC(=O)c2cnc3c(c2)C[C@@]2(C3)C(=O)Nc3ncccc32)C(=O)N1CC(F)(F)F]

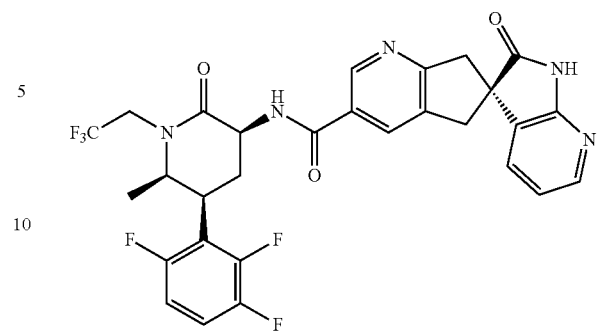

and having the following chemical name: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol solvate.

Figure 9:
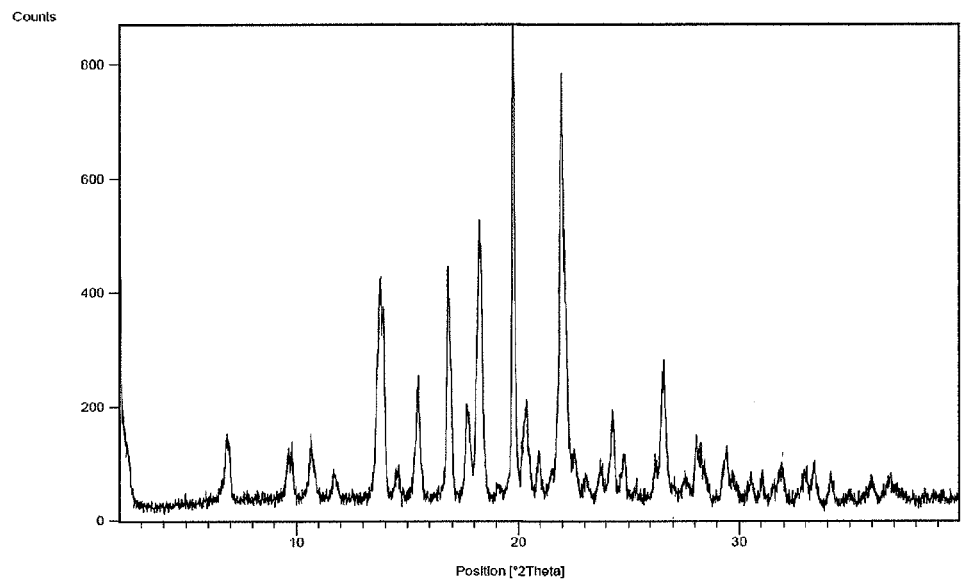
FIG. 9 is the X-ray powder diffraction (XRPD) pattern for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol solvate.

FIG. 9 shows the X-ray powder diffraction pattern for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol solvate. The methanol solvate form is characterized by diffraction peaks corresponding to d-spacings as detailed in Table 5.

TABLE 5

| Pos. [° Two Theta.] | d-spacing [Å] | Rel. Int. [%] |
| --- | --- | --- |
| 6.89 | 12.83 | 13 |
| 9.67 | 9.15 | 10 |
| 10.69 | 8.28 | 12 |
| 11.71 | 7.56 | 6 |
| 13.82 | 6.41 | 45 |
| 14.51 | 6.10 | 5 |
| 15.47 | 5.73 | 27 |
| 16.82 | 5.27 | 47 |
| 17.72 | 5.00 | 19 |
| 18.29 | 4.85 | 55 |
| 19.76 | 4.49 | 100 |
| 20.35 | 4.36 | 18 |
| 20.93 | 4.24 | 10 |
| 21.97 | 4.05 | 89 |
| 22.54 | 3.94 | 10 |
| 23.06 | 3.86 | 5 |
| 23.71 | 3.75 | 11 |
| 24.30 | 3.66 | 17 |
| 24.81 | 3.59 | 10 |
| 26.24 | 3.40 | 10 |
| 26.61 | 3.35 | 28 |
| 27.58 | 3.23 | 6 |
| 29.43 | 3.04 | 10 |
| 30.54 | 2.93 | 5 |
| 31.05 | 2.88 | 6 |

Another embodiment of the invention encompasses crystalline methanol-water mixed solvate free base of the compound having the structure and having the following chemical name: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol water solvate.

Figure 10:
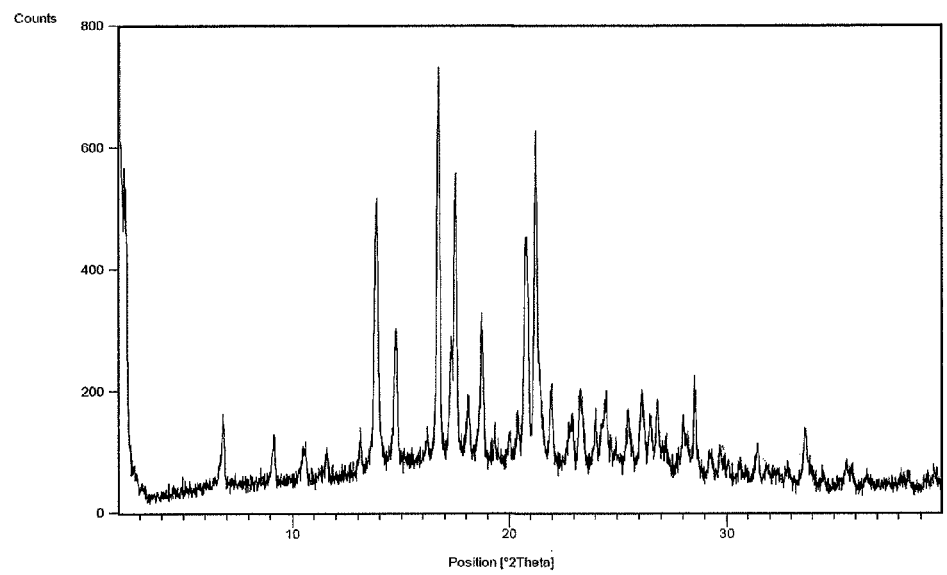
FIG. 10 is the X-ray powder diffraction (XRPD) pattern for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol water solvate.

FIG. 10 shows the X-ray powder diffraction pattern for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol-water solvate. The methanol-water mixed solvate form is characterized by diffraction peaks corresponding to d-spacings as detailed in Table 6.

TABLE 6

| Pos. [° Two Theta.] | d-spacing [Å] | Rel. Int. [%] |
| --- | --- | --- |
| 6.81 | 12.98 | 18 |
| 9.17 | 9.65 | 14 |
| 10.53 | 8.40 | 10 |
| 11.61 | 7.62 | 8 |
| 13.12 | 6.75 | 13 |
| 13.86 | 6.39 | 70 |
| 14.76 | 6.00 | 36 |
| 16.23 | 5.46 | 7 |
| 16.72 | 5.30 | 100 |
| 17.33 | 5.12 | 32 |
| 17.51 | 5.06 | 75 |
| 18.11 | 4.90 | 17 |
| 18.72 | 4.74 | 40 |
| 19.32 | 4.59 | 11 |
| 20.03 | 4.43 | 10 |
| 20.40 | 4.35 | 13 |
| 20.84 | 4.26 | 57 |
| 21.26 | 4.18 | 84 |
| 21.97 | 4.05 | 21 |
| 22.91 | 3.88 | 15 |
| 23.30 | 3.82 | 21 |
| 24.01 | 3.71 | 15 |
| 24.45 | 3.64 | 16 |
| 25.52 | 3.49 | 14 |
| 26.13 | 3.41 | 18 |
| 26.51 | 3.36 | 14 |
| 26.83 | 3.32 | 19 |
| 28.02 | 3.18 | 16 |
| 28.55 | 3.13 | 20 |
| 29.27 | 3.05 | 7 |

Another embodiment of the invention encompasses crystalline acetonitrile water solvate free base of the compound having the structure

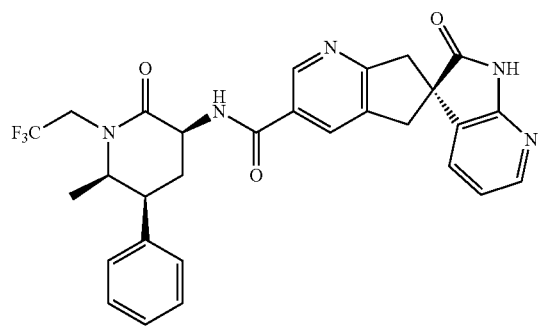 [SMILES: C[C@@H]1[C@H](c2ccccc2)C[C@H](NC(=O)c2cnc3c(c2)C[C@@]2(C3)C(=O)Nc3ncccc32)C(=O)N1CC(F)(F)F]

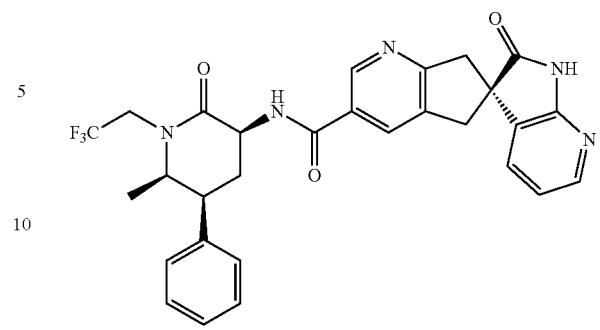

Figure 11:
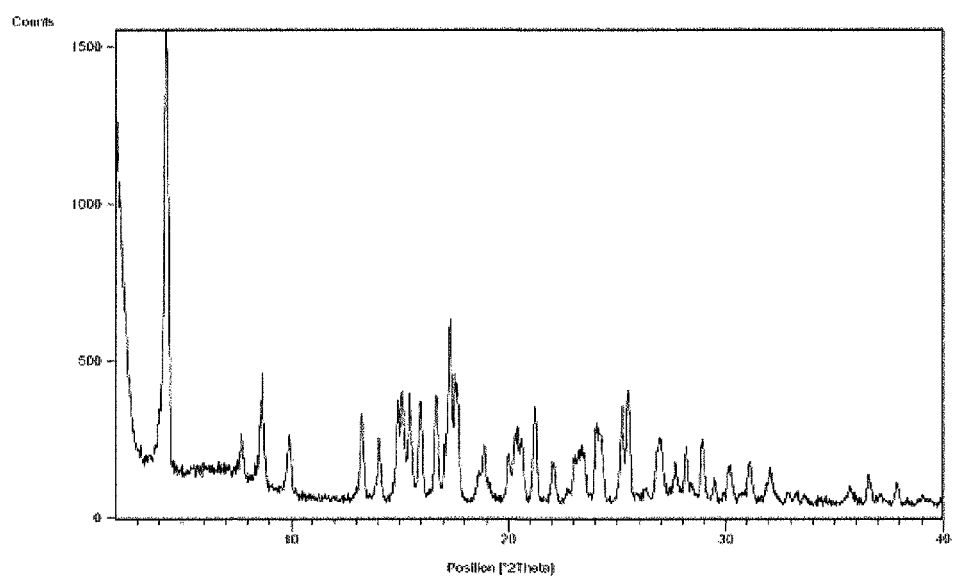
FIG. 11 is the XRPD of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide acetonitrile water solvate.

FIG. 11 shows the X-ray powder diffraction pattern of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide acetronitrile water solvate. The acetonitrile water solvate form is characterized by diffraction peaks corresponding to d-spacings as detailed in Table 7.

Figure 12:
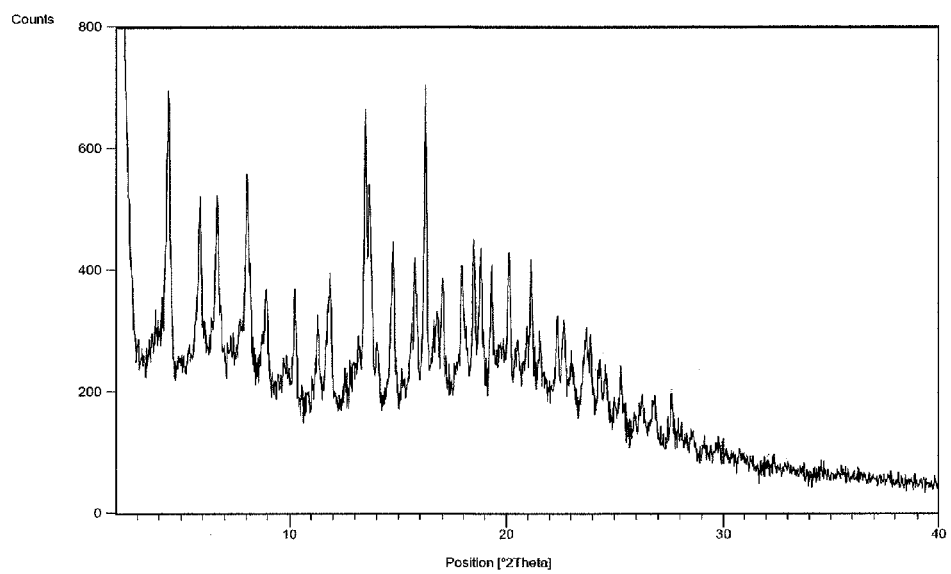
FIG. 12 is the XRPD of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide acetonitrile solvate.

FIG. 12 shows the X-ray powder diffraction pattern of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide acetronitrile solvate. The acetonitrile solvate form is characterized by diffraction peaks corresponding to d-spacings as detailed in Table 8.

TABLE 7

| Pos. [° Two Theta.] | d-spacing [Å] | Rel. Int. [%] |
|---|---|---|
| 4.30 | 20.53 | 100 |
| 7.72 | 11.45 | 11 |
| 8.66 | 10.21 | 26 |
| 9.92 | 8.92 | 14 |
| 13.26 | 6.68 | 19 |
| 14.06 | 6.30 | 14 |
| 14.95 | 5.93 | 20 |
| 15.12 | 5.86 | 24 |
| 15.48 | 5.72 | 23 |
| 15.96 | 5.55 | 21 |
| 16.71 | 5.31 | 23 |
| 17.33 | 5.12 | 40 |
| 17.56 | 5.05 | 26 |
| 18.89 | 4.70 | 13 |
| 20.02 | 4.44 | 11 |
| 20.32 | 4.37 | 15 |
| 20.43 | 4.35 | 17 |
| 20.61 | 4.31 | 14 |
| 21.23 | 4.19 | 21 |
| 22.06 | 4.03 | 10 |
| 23.19 | 3.84 | 12 |
| 24.10 | 3.69 | 15 |
| 25.21 | 3.53 | 21 |
| 25.50 | 3.49 | 24 |
| 26.97 | 3.31 | 14 |
| 27.69 | 3.22 | 7 |
| 28.15 | 3.17 | 11 |
| 28.92 | 3.09 | 13 |
| 29.47 | 3.03 | 5 |
| 30.18 | 2.96 | 8 |
| 31.11 | 2.88 | 9 |
| 32.06 | 2.79 | 7 |

TABLE 8

| Pos. [° Two Theta.] | d-spacing [Å] | Rel. Int. [%] |
|---|---|---|
| 4.42 | 19.99 | 94 |
| 5.87 | 15.05 | 62 |
| 6.67 | 13.25 | 67 |
| 8.05 | 10.98 | 75 |
| 8.94 | 9.89 | 42 |
| 10.26 | 8.62 | 44 |
| 11.32 | 7.82 | 35 |
| 11.89 | 7.45 | 43 |
| 13.50 | 6.56 | 94 |
| 13.68 | 6.47 | 73 |
| 14.03 | 6.31 | 26 |
| 14.77 | 6.00 | 56 |
| 15.79 | 5.61 | 50 |
| 16.26 | 5.45 | 100 |
| 17.04 | 5.20 | 44 |
| 17.94 | 4.95 | 46 |
| 18.50 | 4.80 | 53 |
| 18.83 | 4.71 | 50 |
| 19.33 | 4.59 | 40 |
| 20.15 | 4.41 | 48 |
| 21.17 | 4.20 | 45 |
| 22.37 | 3.97 | 34 |
| 22.67 | 3.92 | 34 |
| 23.70 | 3.75 | 33 |
| 24.33 | 3.66 | 25 |
| 24.59 | 3.62 | 22 |
| 25.29 | 3.52 | 22 |
| 26.27 | 3.39 | 17 |
| 26.81 | 3.33 | 18 |
| 27.62 | 3.23 | 21 |

Another embodiment of the invention encompasses crystalline acetonitrile solvate free base of the compound having the structure Another embodiment of the invention encompasses X-ray amorphous free base of the compound having the structure

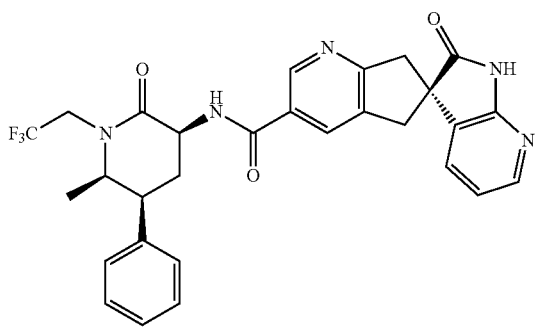 [SMILES: C[C@@H]1[C@H](c2ccccc2)C[C@H](NC(=O)c2cnc3c(c2)C[C@@]2(C3)C(=O)Nc3ncccc32)C(=O)N1CC(F)(F)F]

Figure 13:
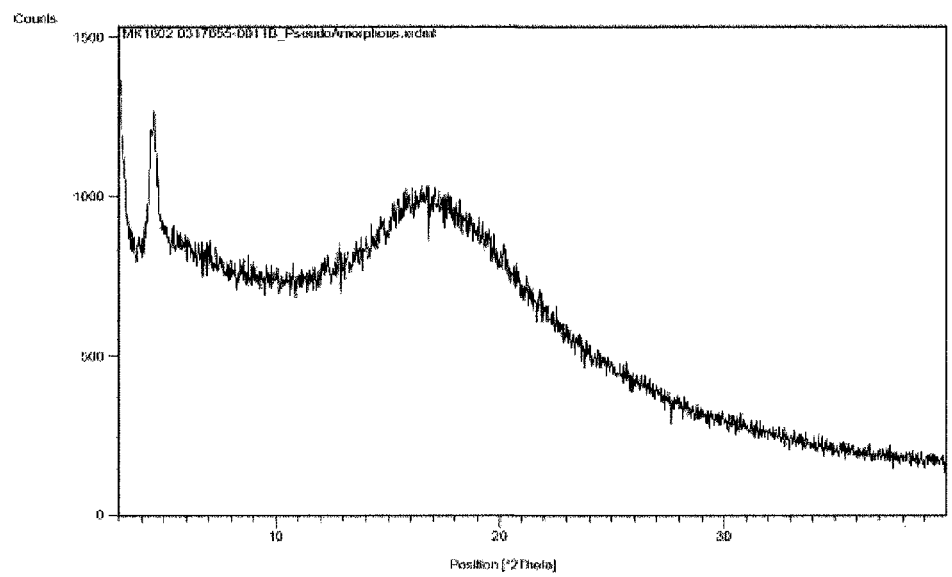
FIG. 13 is the XRPD of X-ray Amorphous (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide.

FIG. 13 shows the X-ray powder diffraction pattern of X-ray amorphous (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide which is generated via desolvation of an acetonitrile solvate. The X-ray amorphous pattern displays a broad diffuse halo with only a single low angle peak at approximately 5° two-theta.

Another embodiment of the invention encompasses crystalline acetonitrile solvate free base of the compound having the structure

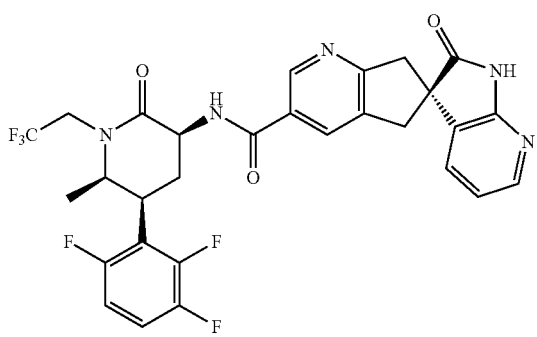 [SMILES: C[C@@H]1[C@H](c2c(F)ccc(F)c2F)C[C@H](NC(=O)c2cnc3c(c2)C[C@@]2(C3)C(=O)Nc3ncccc32)C(=O)N1CC(F)(F)F]

and having the following chemical name: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide acetonitrile solvate.

Figure 14:
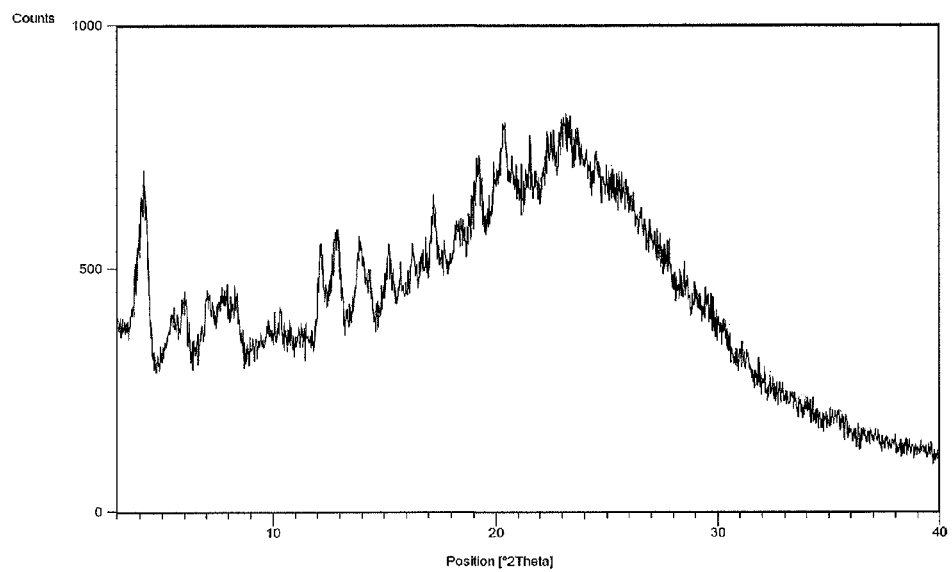
FIG. 14 is the X-ray powder diffraction (XRPD) pattern for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide acetonitrile solvate.

FIG. 14 shows the X-ray powder diffraction pattern for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide acetonitrile solvate. The acetonitrile solvate form is characterized by diffraction peaks corresponding to d-spacings as detailed in Table 9.

TABLE 9

| Pos. [° Two Theta.] | d-spacing [Å] | Rel. Int. [%] |
|---|---|---|
| 4.22 | 20.92 | 100 |
| 6.01 | 14.71 | 49 |
| 7.07 | 12.50 | 44 |
| 7.82 | 11.31 | 41 |
| 8.35 | 10.58 | 45 |
| 12.15 | 7.29 | 60 |
| 12.83 | 6.90 | 66 |
| 13.92 | 6.36 | 59 |
| 15.20 | 5.83 | 48 |
| 17.21 | 5.15 | 61 |

TABLE 9-continued

| Pos. [° Two Theta.] | d-spacing [Å] | Rel. Int. [%] |
|---|---|---|
| 19.23 | 4.62 | 59 |
| 20.38 | 4.36 | 72 |

Another embodiment of the invention encompasses crystalline L-tartaric Acid cocrystal of the compound having the structure

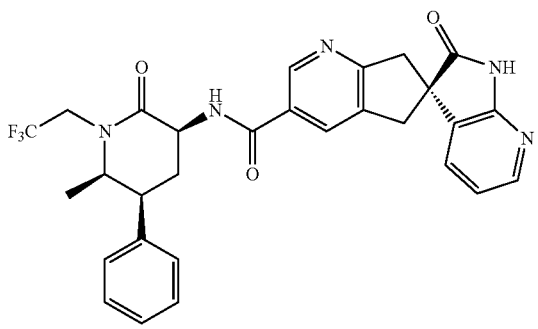 [SMILES: C[C@@H]1[C@H](c2ccccc2)C[C@H](NC(=O)c2cnc3c(c2)C[C@@]2(C3)C(=O)Nc3ncccc32)C(=O)N1CC(F)(F)F]

Figure 15:
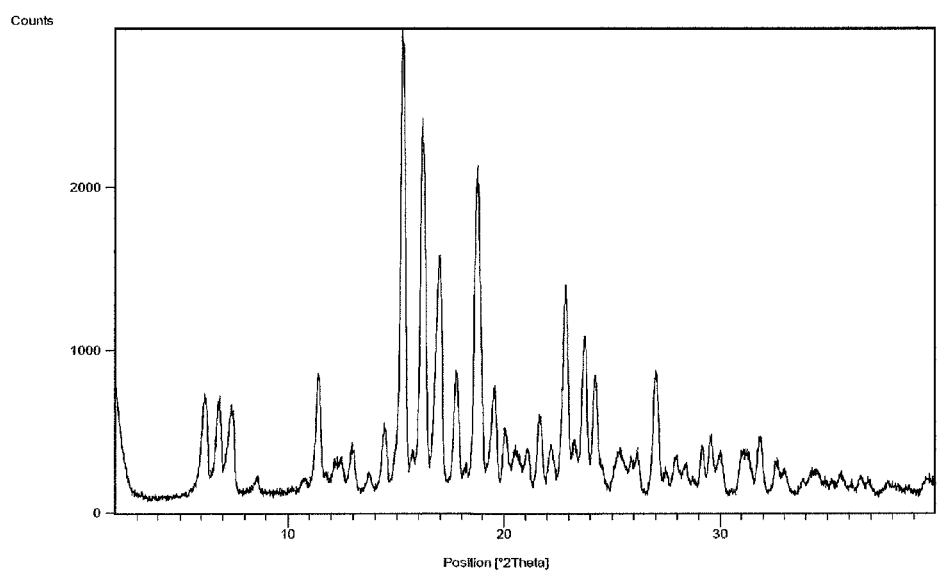
FIG. 15 is the XRPD of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal.

FIG. 15 shows the X-ray powder diffraction pattern of crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal. The L-tartaric acid cocrystal form is characterized by diffraction peaks corresponding to d-spacings as detailed in Table 10.

TABLE 10

| Pos. [° Two Theta.] | d-spacing [Å] | Rel. Int. [%] |
|---|---|---|
| 6.19 | 14.27 | 22 |
| 6.81 | 12.98 | 21 |
| 7.45 | 11.87 | 19 |
| 8.59 | 10.30 | 5 |
| 10.74 | 8.24 | 4 |
| 11.41 | 7.76 | 26 |
| 12.18 | 7.26 | 8 |
| 12.45 | 7.11 | 8 |
| 12.95 | 6.84 | 12 |
| 13.75 | 6.44 | 5 |
| 14.43 | 6.14 | 15 |
| 15.29 | 5.79 | 100 |
| 15.74 | 5.63 | 10 |
| 16.22 | 5.46 | 81 |
| 16.99 | 5.22 | 51 |
| 17.78 | 4.99 | 26 |
| 18.16 | 4.89 | 5 |
| 18.75 | 4.73 | 68 |
| 19.56 | 4.54 | 22 |
| 20.08 | 4.42 | 13 |
| 20.54 | 4.32 | 10 |
| 21.07 | 4.22 | 10 |
| 21.69 | 4.10 | 17 |
| 22.20 | 4.00 | 11 |
| 22.86 | 3.89 | 44 |
| 23.27 | 3.82 | 11 |
| 23.74 | 3.75 | 34 |
| 24.21 | 3.68 | 26 |
| 25.33 | 3.52 | 10 |
| 26.17 | 3.41 | 10 |
| 27.02 | 3.30 | 27 |
| 27.47 | 3.25 | 7 |
| 27.96 | 3.19 | 9 |
| 28.37 | 3.15 | 7 |
| 29.17 | 3.06 | 11 |
| 29.57 | 3.02 | 13 |
| 30.02 | 2.98 | 11 |

TABLE 10-continued

| Pos. [° Two Theta.] | d-spacing [Å] | Rel. Int. [%] |
|---|---|---|
| 31.18 | 2.87 | 10 |
| 31.86 | 2.81 | 14 |
| 32.61 | 2.75 | 7 |
| 32.96 | 2.72 | 6 |
| 33.86 | 2.65 | 4 |
| 35.61 | 2.52 | 6 |
| 36.54 | 2.46 | 5 |
| 36.92 | 2.43 | 4 |
| 39.32 | 2.29 | 2 |

Another embodiment of the invention encompasses crystalline L-tartaric acid cocrystal of the compound having the structure

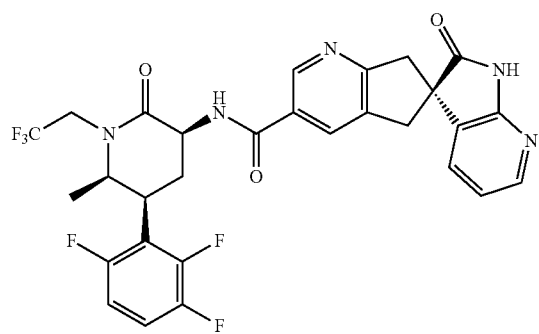 [SMILES: C[C@@H]1[C@H](c2c(F)ccc(F)c2F)C[C@H](NC(=O)c2cnc3c(c2)C[C@@]2(C3)C(=O)Nc3ncccc32)C(=O)N1CC(F)(F)F]

and having the following chemical name: (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal.

Figure 16:
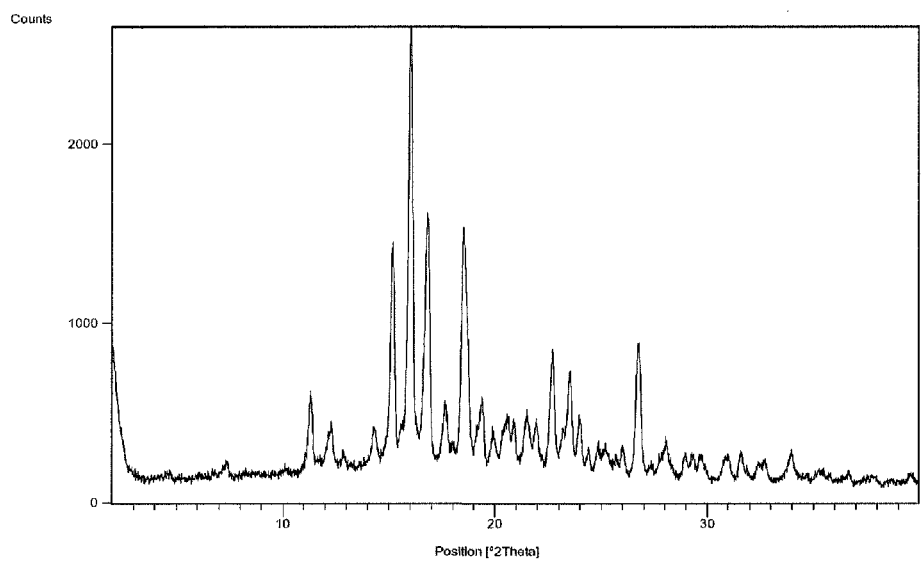
FIG. 16 is the X-ray powder diffraction (XRPD) pattern for (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal.

FIG. 16 shows the X-ray powder diffraction pattern for crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal. The L-tartaric cocrystal form is characterized by diffraction peaks corresponding to d-spacings as detailed in Table 11.

TABLE 11

| Pos. [° Two Theta.] | d-spacing [Å] | Rel. Int. [%] |
|---|---|---|
| 7.35 | 12.02 | 5 |
| 11.32 | 7.82 | 20 |
| 12.27 | 7.21 | 12 |
| 12.89 | 6.87 | 6 |
| 14.31 | 6.19 | 11 |
| 15.20 | 5.83 | 52 |
| 16.04 | 5.52 | 100 |
| 16.84 | 5.27 | 58 |
| 17.64 | 5.03 | 16 |
| 18.56 | 4.78 | 55 |
| 19.40 | 4.58 | 18 |
| 19.94 | 4.45 | 9 |
| 20.57 | 4.32 | 14 |
| 20.92 | 4.25 | 12 |
| 21.49 | 4.13 | 14 |
| 21.94 | 4.05 | 13 |
| 22.70 | 3.92 | 29 |
| 23.20 | 3.83 | 12 |
| 23.52 | 3.78 | 24 |
| 24.00 | 3.71 | 14 |
| 24.38 | 3.65 | 7 |
| 24.85 | 3.58 | 9 |

TABLE 11-continued

| Pos. [° Two Theta.] | d-spacing [Å] | Rel. Int. [%] |
|---|---|---|
| 25.19 | 3.53 | 9 |
| 25.69 | 3.47 | 5 |
| 25.99 | 3.43 | 8 |
| 26.74 | 3.33 | 31 |
| 28.08 | 3.18 | 10 |
| 28.98 | 3.08 | 8 |
| 29.33 | 3.04 | 7 |
| 29.68 | 3.01 | 7 |
| 30.93 | 2.89 | 6 |
| 31.62 | 2.83 | 8 |
| 32.40 | 2.76 | 6 |
| 32.72 | 2.74 | 6 |
| 33.96 | 2.64 | 9 |

Another embodiment of the invention encompasses a crystalline free base of the compound having the structure

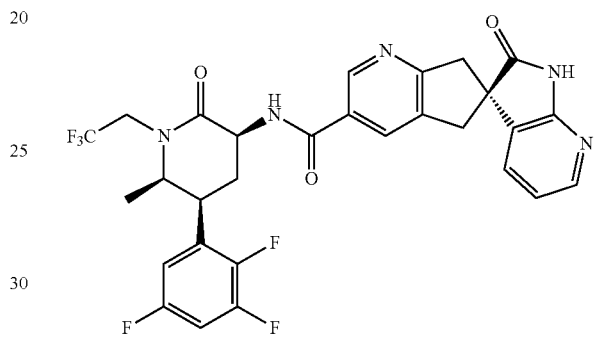

and having the following chemical name: (S)—N-((3S,5S,6R)-6-methyl-2-oxo-1-(2,2,2-trifluoroethyl)-5-(2,3,5-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide.

Figure 17:
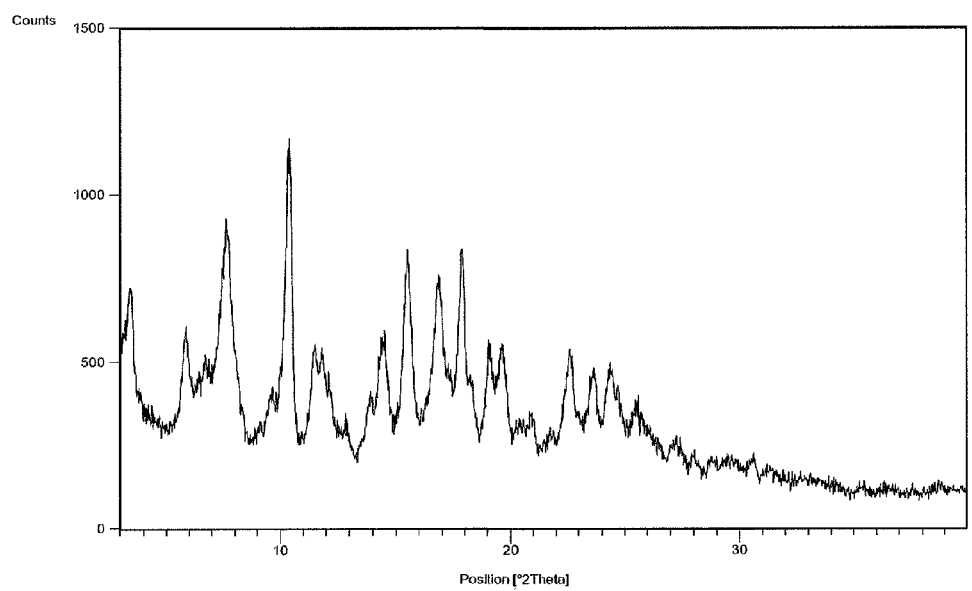
FIG. 17 is the X-ray powder diffraction (XRPD) pattern for a crystalline form of (S)—N-((3S,5S,6R)-6-methyl-2-oxo-1-(2,2,2-trifluoroethyl)-5-(2,3,5-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide.

FIG. 17 shows the X-ray powder diffraction pattern for crystalline (S)—N-((3S,5S,6R)-6-methyl-2-oxo-1-(2,2,2-trifluoroethyl)-5-(2,3,5-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide. The form is characterized by diffraction peaks corresponding to d-spacings as detailed in Table 12.

TABLE 12

| Pos. [° Two Theta.] | d-spacing [Å] | Rel. Int. [%] |
|---|---|---|
| 5.85 | 15.10 | 40 |
| 7.64 | 11.58 | 73 |
| 9.62 | 9.20 | 22 |
| 10.37 | 8.53 | 100 |
| 11.50 | 7.70 | 38 |
| 11.81 | 7.50 | 37 |
| 12.87 | 6.88 | 19 |
| 13.92 | 6.36 | 26 |
| 14.49 | 6.11 | 41 |
| 15.52 | 5.71 | 67 |
| 16.86 | 5.26 | 62 |
| 17.89 | 4.96 | 69 |
| 18.33 | 4.84 | 30 |
| 19.07 | 4.65 | 42 |
| 19.64 | 4.52 | 40 |
| 20.98 | 4.23 | 22 |
| 22.60 | 3.93 | 41 |
| 23.68 | 3.76 | 35 |
| 24.36 | 3.65 | 37 |
| 25.47 | 3.50 | 24 |

ABBREVIATIONS

The following abbreviations are used throughout the specification.
Bs=benzenesulfonyl
Boc=tert-butoxycarbonyl
BOM=benzyloxymethyl
BOP=(benzotriazole-1-yloxy)-tris(dimethylamino)phosphonium hexafluorophosphate
Cbz=benzyloxycarbonyl
CDI=1,1'-carbonyldiimidazole
CPME=cyclopentyl methyl ether
DBU=1,8-diazabicyclo[5.4.0]undec-7-ene
DCC=N,N-dicyclohexylcarbodiimide
DCM=dichloromethane
DCPE=1,3-bis(dicyclohexylphosphino)ethane
DCPP=1,3-bis(dicyclohexylphosphino)propane
DHP=3,4-dihydro-2H-pyran
DMAc=N,N-dimethylacetamide
DMF=N,N-dimethylformamide
DMPU=1,3-dimethyl-3,4,5,6-tetrahydro-2(1H)-pyrimidinone
DMSO=dimethyl sulfoxide
DPPA=diphenylphosphoryl azide
EDC=N-(3-dimethylaminopropyl)-N'-ethylcarbodiimide hydrochloride
HATU=O-(7-azabenzotriazol-1-yl)-N,N,N'N'-tetramethyluronium HCl
HCl=hydrochloric acid
HOAt=1-hydroxy-7-azabenzotriazole
HOPO=2-hydroxypyridine-N-oxide
HOBT=1-hydroxybenzotriazole
HOSu=N-hydroxysuccinimide
IPA or iPA=isopropyl alcohol
IPAc=isopropyl acetate
LCAP=liquid chromatography area percent
LiHMDS=lithium bis(trimethylsilyl)amide
Ms=methanesulfonyl
MOM=methoxymethyl
MTBE=methyl tert-butyl ether
NMP=N-methyl-2-pyrrolidone
Ph=phenyl
PTC=phase transfer catalyst
RBF=round bottom flask
RT=room temperature
SEM=2-(trimethylsilyl)ethoxymethyl
SFC=supercritical fluid chromatography
TBDMS=tert-butyldimethylsilyl
TEA=triethylamine
TES=triethylsilyl
THF=tetrahydrofuran
THP=tetrahydropyranyl
TIPS=triisopropylsilyl
TMS=trimethylsilyl
Ts=toluenesulfonyl Previous methods for synthesizing compounds of Formula I are shown in Schemes 1 to 15 described below.

Scheme 1 illustrates a route to 3-aminopiperidinone intermediates of type 1.5 which may be used to prepare compounds of the present invention. Aryl acetone 1.1 can be alkylated using the iodoalanine derivative 1.2 under basic conditions to provide keto ester 1.3. Reductive amination followed by cyclization and epimerization provides primarily cis-substituted lactam 1.4 as a racemic mixture. Chiral resolution using normal-phase liquid chromatography, for example, and removal of the Boc protecting group with HCl in EtOAc furnishes 3-aminopiperidinone 1.5 as a hydrochloride salt.

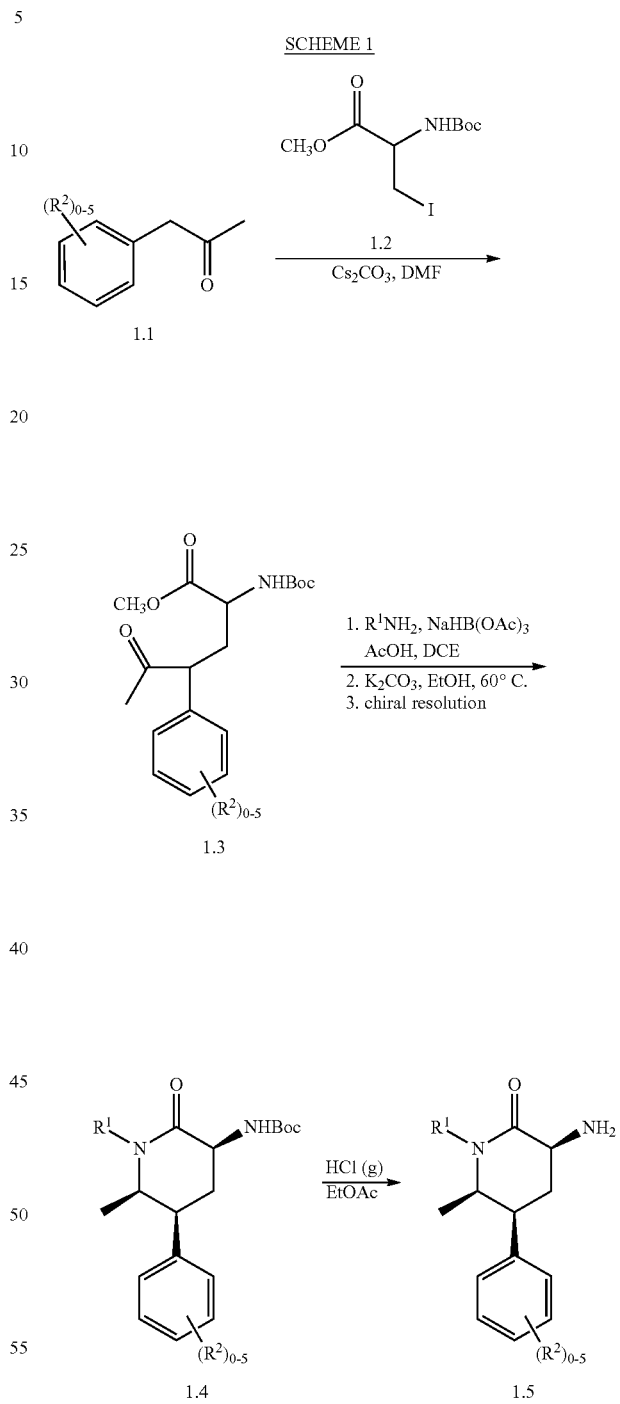

An alternative sequence to 3-aminopiperidinone intermediates of type 1.5 is shown in Scheme 2. Reductive amination of keto ester 1.3 with ammonia followed by epimerization provides 2.1 as a mostly cis-substituted racemic mixture. Chiral resolution of the enantiomers provides 2.2. N-Alkylation with LiHMDS as base, for example, and an alkyl halide or epoxide affords 1.4. Removal of the Boc protecting group with HCl then affords 1.5 as a hydrochloride salt.

SCHEME 2

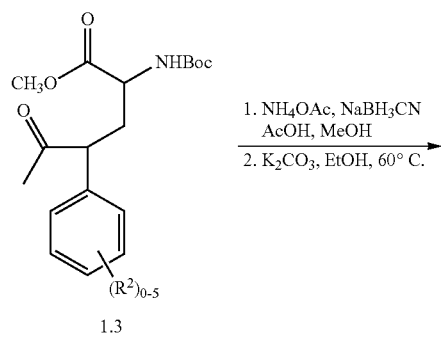

1.3

1. NH$_4$OAc, NaBH$_3$CN
   AcOH, MeOH
2. K$_2$CO$_3$, EtOH, 60° C.

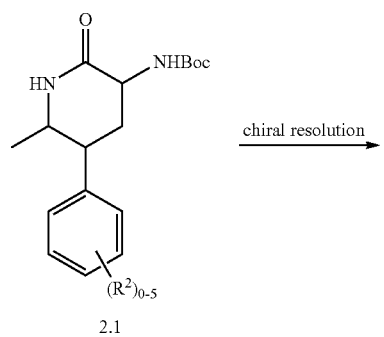

2.1 chiral resolution

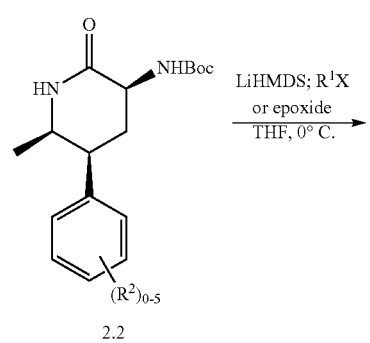

2.2

LiHMDS; R$^1$X
or epoxide
THF, 0° C.

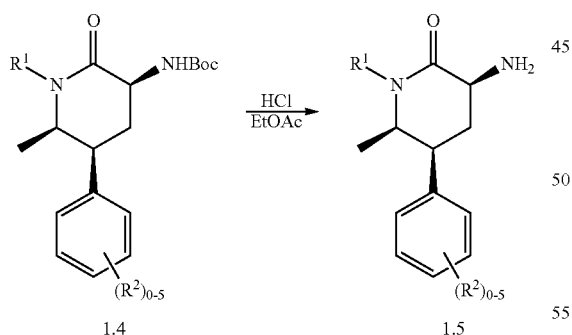

1.4    HCl / EtOAc    1.5

SCHEME 3

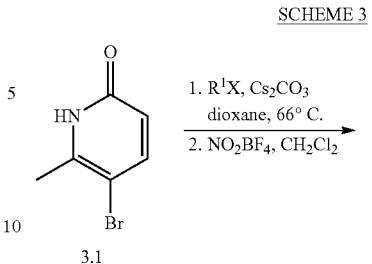

3.1

1. R$^1$X, Cs$_2$CO$_3$
   dioxane, 66° C.
2. NO$_2$BF$_4$, CH$_2$Cl$_2$

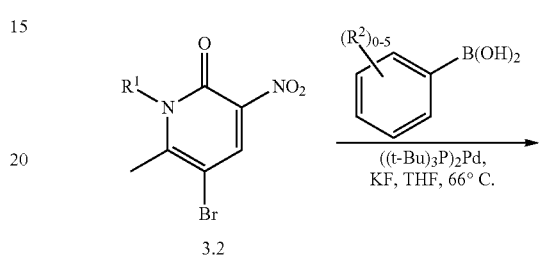

3.2

((t-Bu)$_3$P)$_2$Pd,
KF, THF, 66° C.

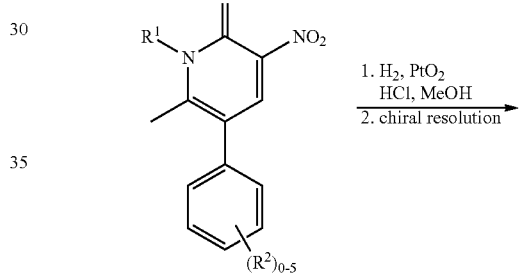

3.3

1. H$_2$, PtO$_2$
   HCl, MeOH
2. chiral resolution

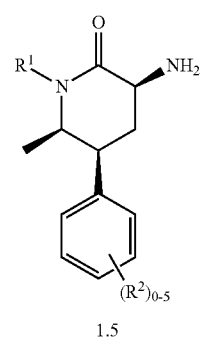

1.5

A third method to 3-aminopiperidinone intermediates of type 1.5 is shown in Scheme 3. N-Alkylation of 5-bromo-6-methylpyridin-2(1H)-one (3.1) using cesium carbonate as base and an alkyl halide followed by nitration provides 3.2. Palladium-catalyzed cross-coupling with an aryl boronic acid then affords 3.3. Hydrogenation using platinum oxide under acidic conditions and chiral resolution of the mostly cis-substituted racemic product mixture provides 1.5 as a single enantiomer.

A synthetic route to 3-aminopiperidinone intermediates of type 4.4 is shown in Scheme 4. Aryl acetonitrile 4.1 can be alkylated using the iodoalanine derivative 1.2 under basic conditions to provide cyano ester 4.2. Reductive cyclization using hydrogen and palladium hydroxide on carbon or Raney nickel, epimerization, and chiral resolution affords cis lactam 4.3 as a single enantiomer. N-Alkylation and removal of the Boc protecting group then provides 4.4 as a hydrochloride salt.

SCHEME 4

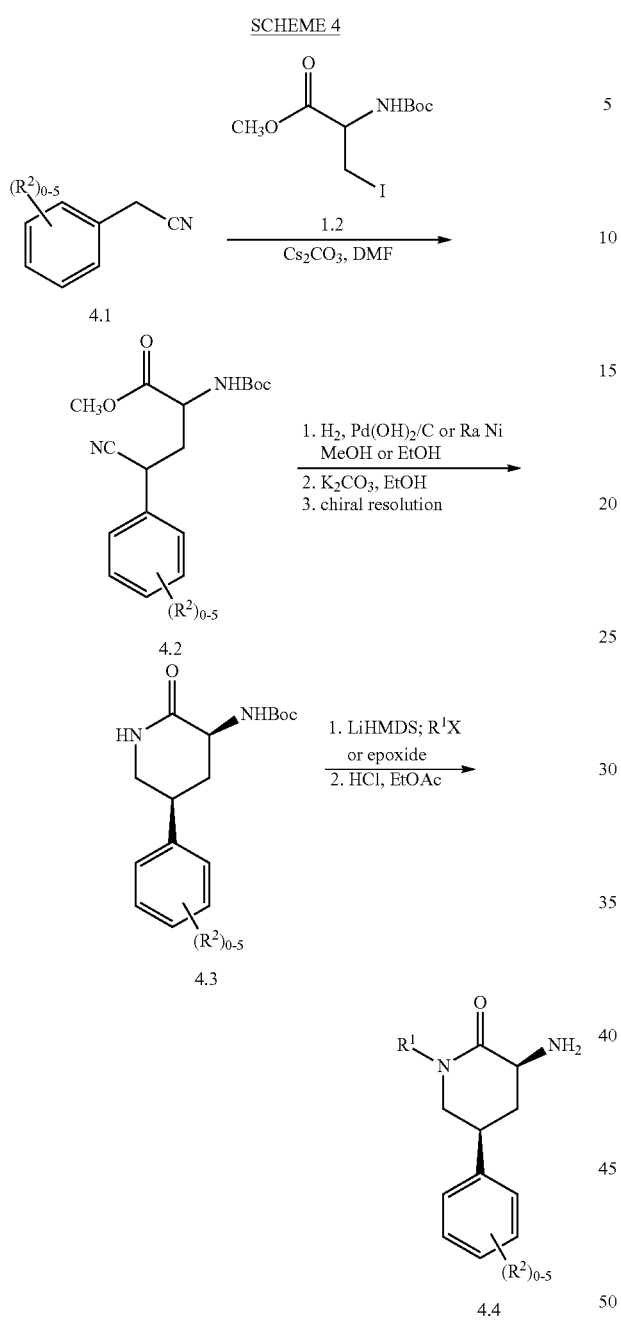

can be separated by chromatography. The desired cis diastereomer of azide 5.6 may be reduced by catalytic hydrogenation in the presence of di-tert-butyl dicarbonate to give the corresponding Boc-protected amine 5.7, and separation of the enantiomers using chiral HPLC or SFC leads to the (3S,5S)-isomer 5.8. Finally, standard deprotection affords the desired 3-aminopiperidinone intermediate 4.4 as a hydrochloride salt.

SCHEME 5

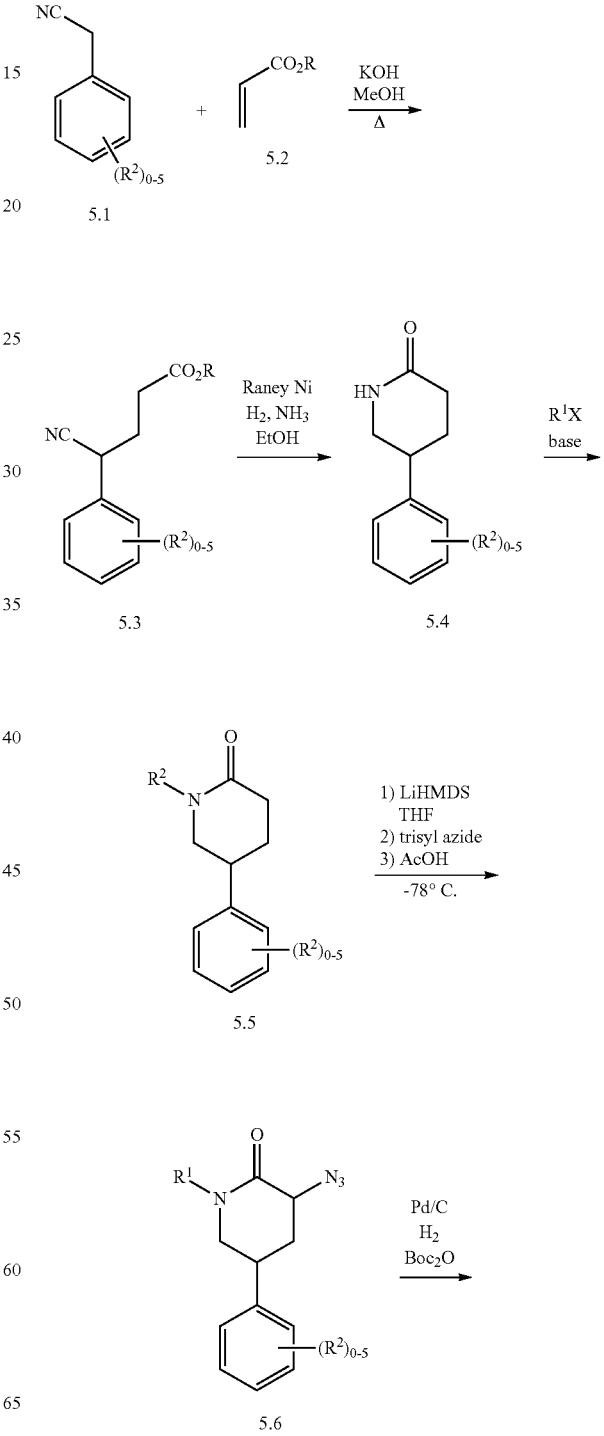

Scheme 5 illustrates an alternative route to 3-aminopiperidinone intermediates of type 4.4. The arylacetonitrile 5.1 may be condensed with acrylate 5.2 at elevated temperature to give the 4-cyanobutanoate ester 5.3. Hydrogenation of nitrile 5.3 using Raney nickel catalyst and an ethanolic solution of ammonia affords the corresponding amine product, which typically cyclizes in situ to provide piperidinone 5.4. N-Alkylation of lactam 5.4 may be accomplished by a variety of methods known to those skilled in the art of organic synthesis, the exact choice of conditions being influenced by the nature of the alkylating agent, $R^1X$. Electrophilic azidation of the resulting substituted lactam 5.5 can be accomplished using similar methodology to that described by Evans and coworkers (Evans et al. (1990) *J. Am. Chem. Soc.* 112, 4011-4030) to provide the azide 5.6 as a mixture of diastereoisomers, which

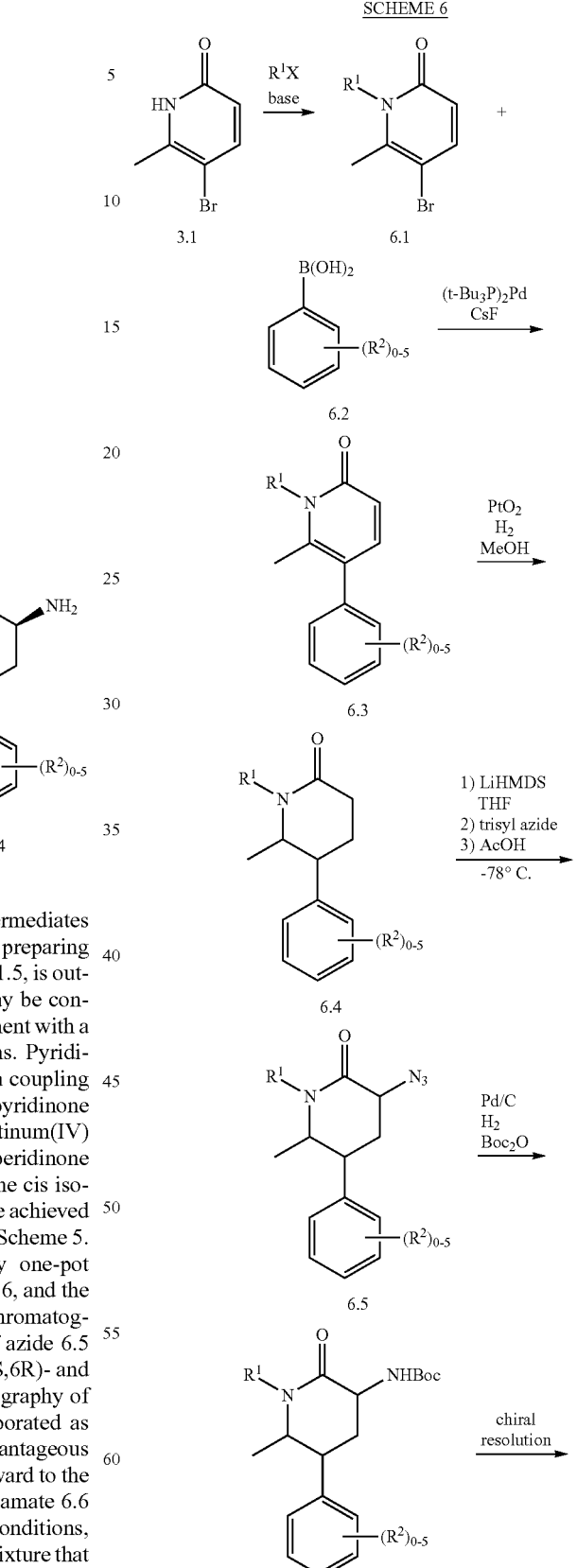

SCHEME 6

Another approach to 3-aminopiperidinone intermediates of interest, which is particularly useful for preparing 3-amino-6-methyl-5-arylpiperidin-2-ones such as 1.5, is outlined in Scheme 6. The pyridin-2(1H)-one 3.1 may be converted to the N-substituted pyridinone 6.1 by treatment with a suitable electrophile (R$^1$X) under basic conditions. Pyridinone 6.1 can then be subjected to Suzuki-Miyaura coupling with the boronic acid 6.2, and the resulting 5-arylpyridinone 6.3 may be hydrogenated using, for example, platinum(IV) oxide catalyst to afford the corresponding 5-arylpiperidinone 6.4, which is usually obtained as predominantly the cis isomer. Further elaboration of piperidinone 6.4 may be achieved using analogous methodology to that described in Scheme 5. Specifically, electrophilic azidation followed by one-pot reduction and Boc protection leads to carbamate 6.6, and the desired enantiomer may be obtained using chiral chromatography. In some cases, the desired diastereomer of azide 6.5 may be isolated as a racemic mixture of the (3S,5S,6R)- and (3R,5R,6S)-isomers following silica gel chromatography of the crude product, and this mixture may be elaborated as outlined in Scheme 6. In other cases, it may be advantageous to take a mixture of diastereomers of azide 6.5 forward to the corresponding carbamate 6.6. The mixture of carbamate 6.6 diastereomers may be epimerized under basic conditions, such as potassium carbonate in EtOH, to afford a mixture that is significantly enriched in the desired (3S,5S,6R)- and (3R, 5R,6S)-isomers, further purification may be employed to obtain the enantiomer of interest as outlined herein.

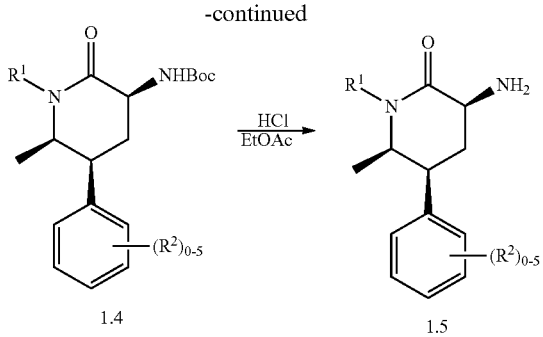

A synthetic route to the azaoxindole pyridine acid intermediate 7.4 is shown in Scheme 7. Diazotization of aminopyridine 7.1, whose preparation is described in WO 2008/020902, followed by treatment with potassium iodide in the presence of NaNO$_2$ provides iodide 7.2. Palladium-catalyzed carbonylation in methanol then affords ester 7.3, which may be saponified with sodium hydroxide to furnish 7.4.

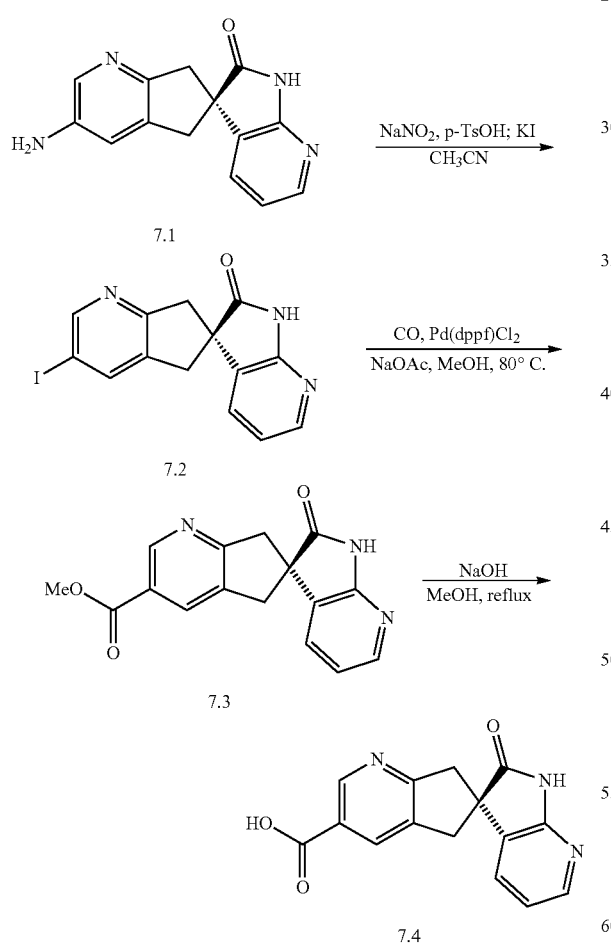

An alternative synthesis of the azaoxindole pyridine acid intermediate 7.4 is shown in Scheme 8. Esterification of diacid 8.1 followed by bromination provides 8.2. Reduction with sodium borohydride then furnishes diol 8.3. Alkylation of the protected azaoxindole 8.4 with the bis-mesylate produced from 8.3 affords the spirocycle 8.5. Palladium-catalyzed carbonylation in methanol followed by chiral resolution gives ester 8.6 as a single enantiomer. Removal of the SEM protecting group under acidic conditions and hydrolysis of the ester using sodium hydroxide then provides 7.4.

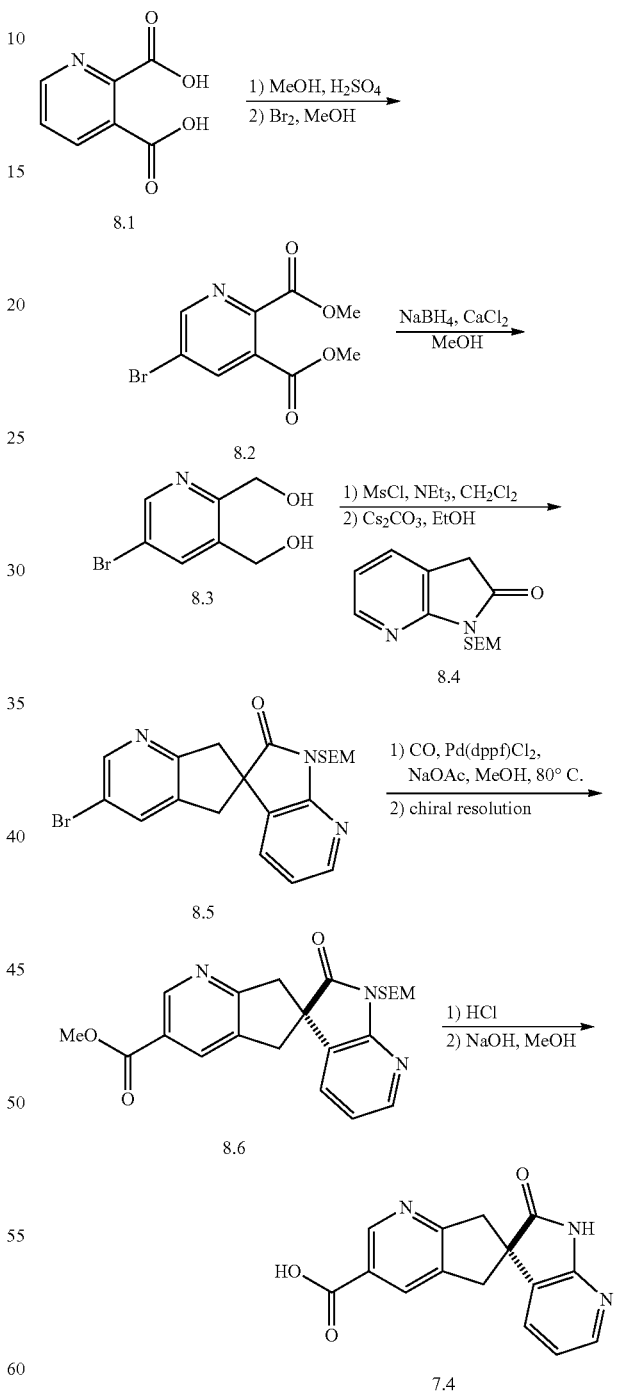

A synthetic route to diazaoxindole carboxylic acid intermediate 9.7 is shown in Scheme 9. Esterification of acid 9.1 is followed by vinylation under palladium catalysis to afford divinyl pyridine 9.2. Ozonolysis with a borohydride reductive workup then yields diol 9.3. After mesylation and treatment with sodium chloride, the resulting dichloro intermediate 9.4 can be alkylated with oxindole 9.5 under basic conditions to give spirocycle 9.6, following chiral resolution of the enantiomers. Dechlorination under buffered hydrogenation conditions and acidic deprotection affords acid 9.7.

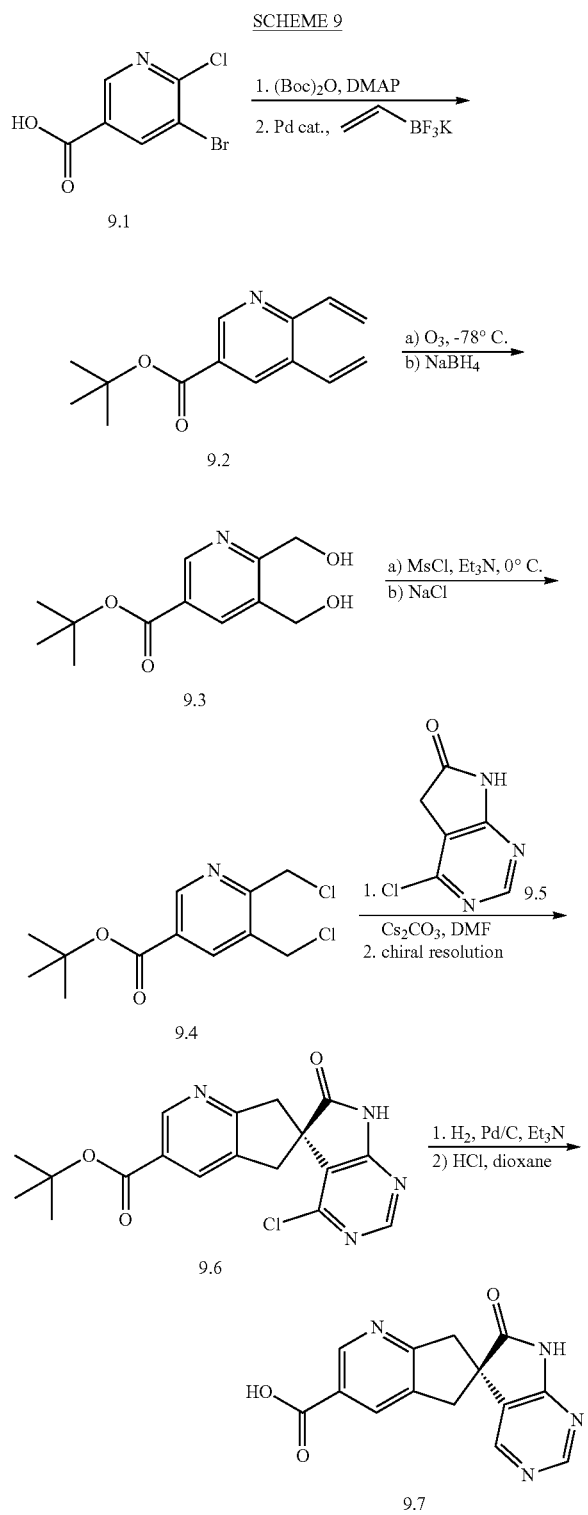

Useful derivatives of the intermediates described herein may be prepared using well-precedented methodology. One such example is illustrated in Scheme 10, in which the azaoxindole intermediate 7.4 is converted to the corresponding nitrile derivative 10.2, which may be used to prepare compounds of the present invention. Bromination of 7.4 with N-bromosuccinimide in boron trifluoride dihydrate provides the bromo derivative 10.1, which may be converted to the desired nitrile 10.2 using zinc cyanide and a palladium catalyst as shown.

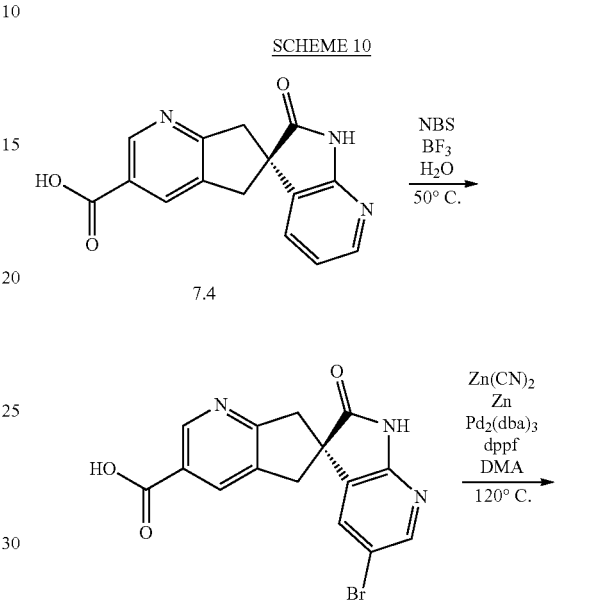

A synthetic route to the azaoxindole indane acid intermediate 11.17 is shown in Scheme 11. Esterification of diacid 11.1 followed by hydrogenation using palladium on carbon as a catalyst provides aniline 11.2. Dibenzylation under basic conditions with heat affords 11.3, and reduction of the diester with LiAlH$_4$ furnishes diol 11.4. Chlorination with thionyl chloride provides benzyl chloride 11.5. Palladium-catalyzed amination of bromide 11.6 with tert-butylamine gives 11.7. Sequential treatment with n-hexyllithium and methyl chloroformate (2x) affords azaoxindole ester 11.8. Alkylation with the benzylchloride 11.5 under basic conditions in the presence of the cinchonidine-derived catalyst 11.12 (prepared via the alkylation of cinchonidine 11.10 with benzyl bromide 11.11) affords spirocycle 11.13. Deprotection of the azaoxindole using methanesulfonic acid with heat and debenzylation under standard hydrogenation conditions provides aniline 11.14. Diazotization followed by treatment with potassium iodide provides iodide 11.15. Palladium-catalyzed carbonylation in methanol then affords ester 11.16, which may be saponified with sodium hydroxide to furnish 11.17.

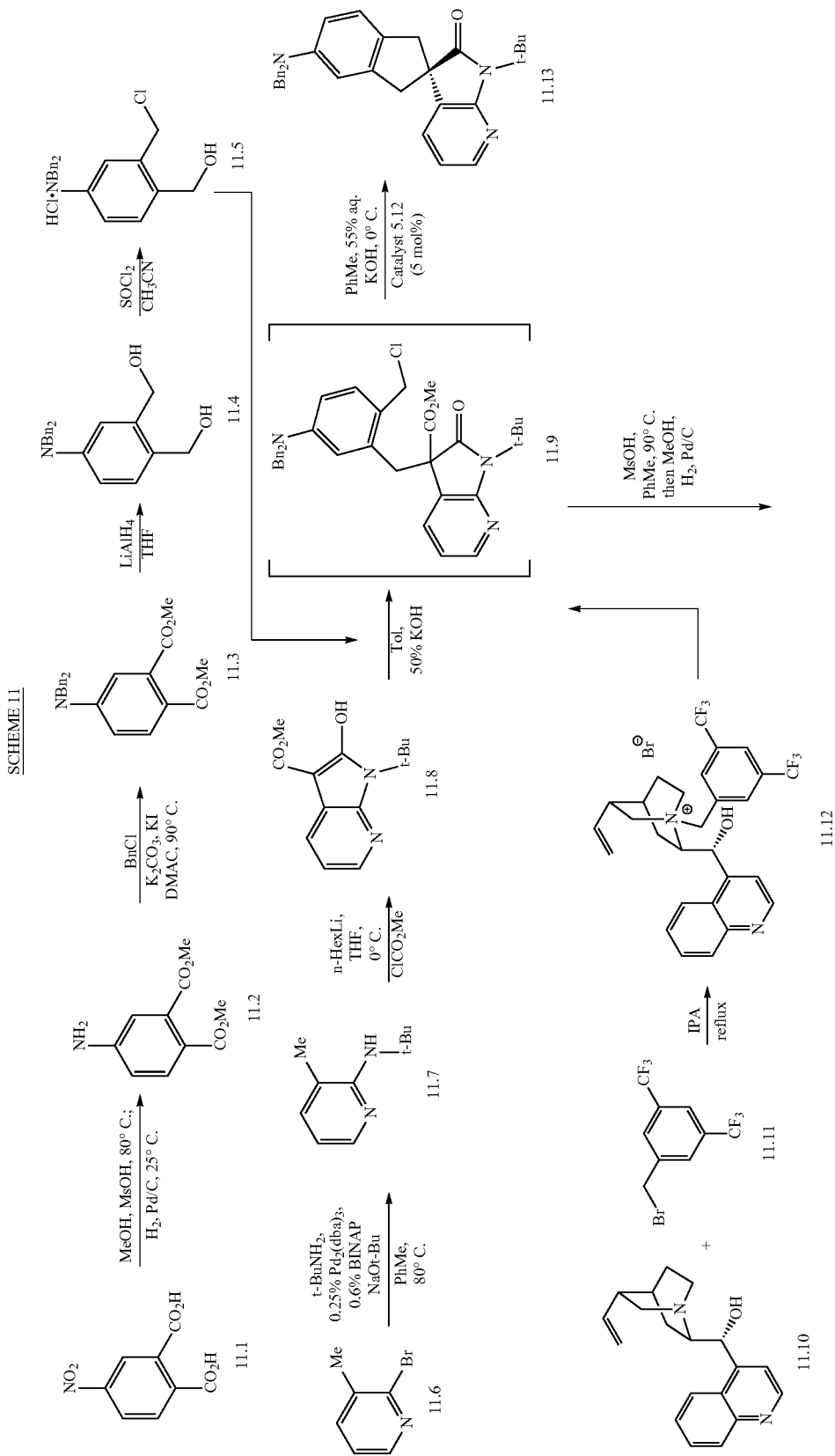

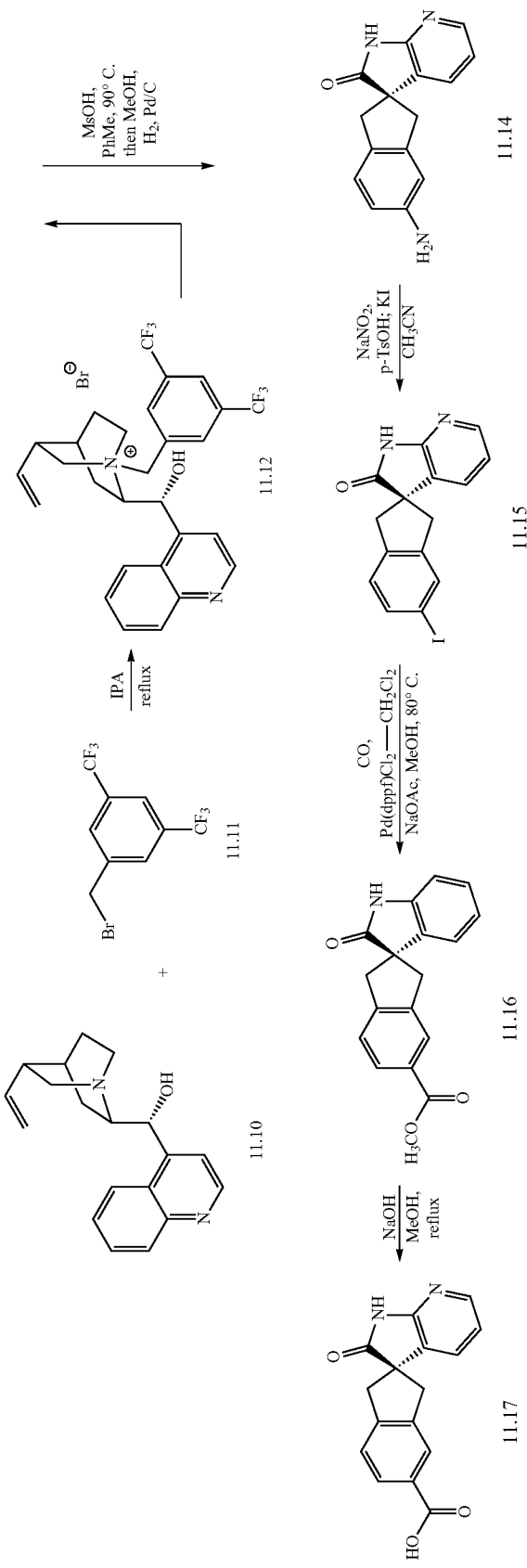

An alternative synthesis of the azaoxindole pyridine acid intermediate 11.17 is shown in Scheme 12. Alkylation of the azaoxindole ester 11.8 with dibenzyl bromide 12.1 followed by chiral resolution of the enantiomers provides ester 12.2. Sequential deprotection of the azaoxindole using methanesulfonic acid with heat and hydrolysis of the ester provides 11.17.

SCHEME 12

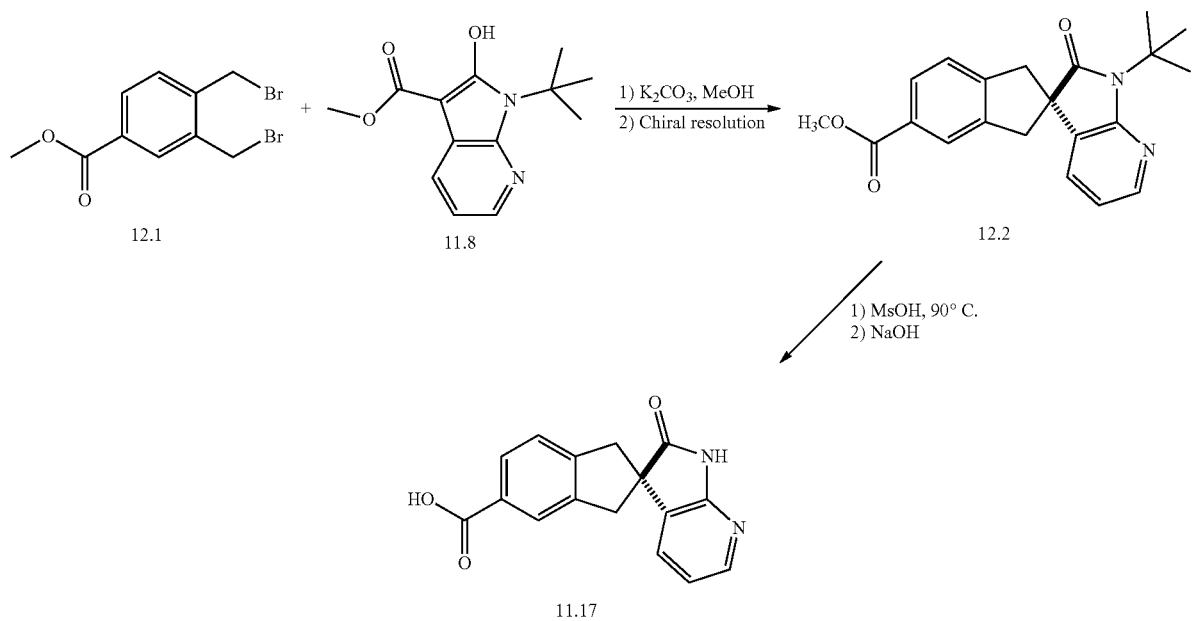

A synthetic route to the diazaoxindole carboxylic acid intermediate 13.4 is shown in Scheme 13. Alkylation of dibromide 12.1 with oxindole 9.5 under basic conditions and subsequent chiral resolution affords spirocycle 13.2. Dechlorination under buffered hydrogenation conditions and ester hydrolysis then affords acid 13.4.

SCHEME 13

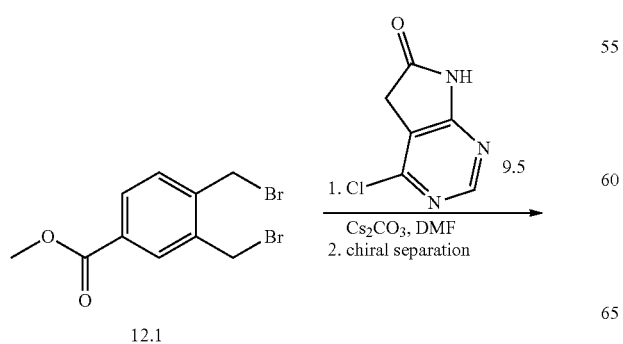

-continued

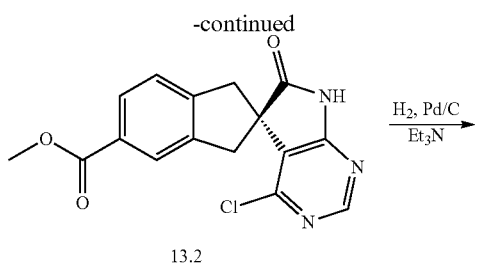

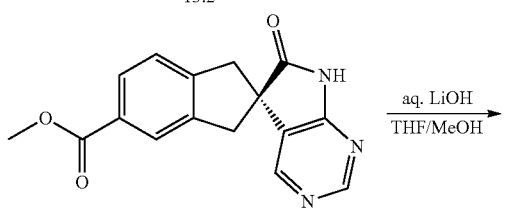

Useful derivatives of the intermediates described herein may be prepared using well-precedented methodology. One such example is illustrated in Scheme 14, in which the aza-oxindole intermediate 11.17 is converted to the corresponding nitrile derivative 14.2, which may be used to prepare compounds of the present invention. Treatment of 11.17 with bromine in acetic acid provides the bromo derivative 14.1, which may be converted to the desired nitrile 14.2 using zinc cyanide and a palladium catalyst as shown.

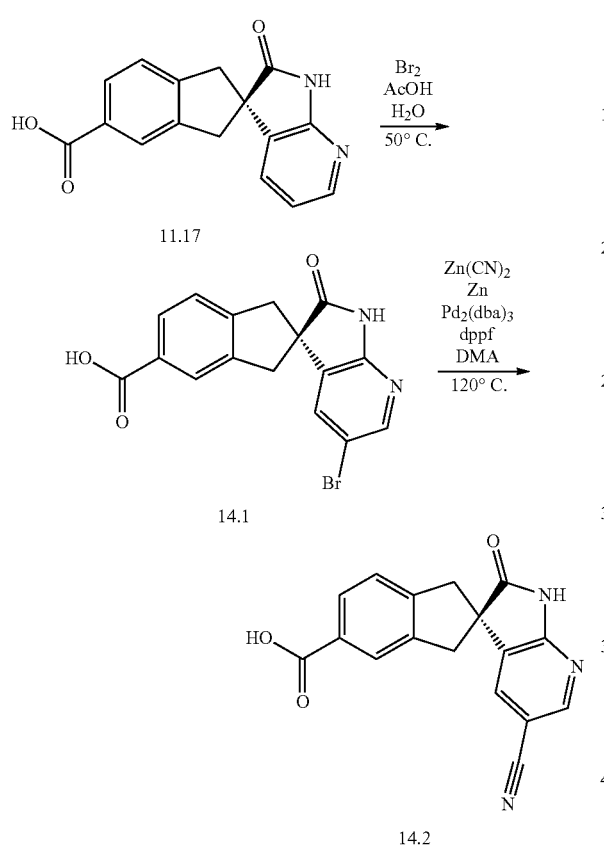

SCHEME 14

11.17

14.1

14.2

Scheme 15 illustrates conditions that can be used for the coupling of 3-aminopiperidinone intermediates, such as 15.1, and carboxylic acid intermediate 15.2, to produce, in this instance, amides 15.3. These standard coupling conditions are representative of the methods used to prepare the compounds of the present invention.

SCHEME 15

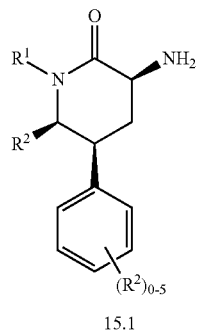

15.1

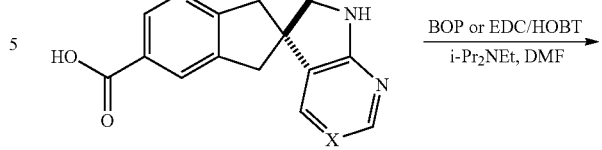

15.2

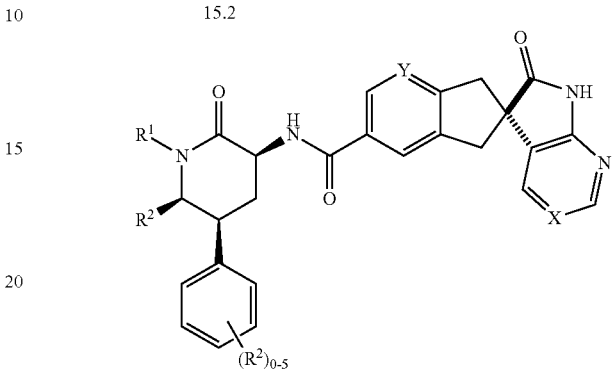

15.3

The previous methods for synthesizing the lactam intermediate suffered from one or more drawbacks: racemic mixture was separated by chiral-HPLC, separation of diasteromixture by crystallization and/or use of costly $PtO_2$. The process of the instant invention utilizes a transaminase induced dynamic kinetic resolution providing high diastereoselectivity at positions C5 and C6. N-mono-trifluoroethylation was discovered and developed. Cis and trans isomer at the alpha position of the amine was successfully controlled by crystallization in the presence of arylaldehyde derivatives. Overall, synthetic steps are shorter, practical and efficient and yield is dramatically improved.

Example 1

Isopropyl 2-(tert-butoxycarbonylamino)-3-(methylsulfonyloxy)propanoate (2)

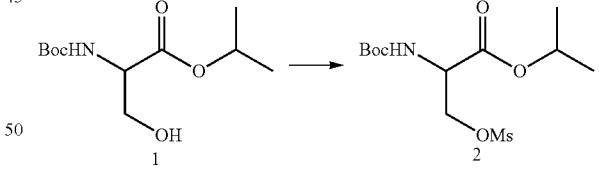

To a solution of N-tert-butyl-L-serine isopropyl ester 1 (12 g, 48.5 mmol)* and methanesulfonyl chloride (4.0 ml) in dichloromethane (100 mL), triethylamine (7.2 ml) was added slowly under an ice bath. The reaction mixture was stirred at room temperature for 1 h, then 1 N HCl (40 mL) was added with stirring. The organic layer was separated, washed with 1 N HCl (40 ml) and brine (40 ml), dried over $MgSO_4$, and concentrated in vacuo to give 2 (14.5 g, 91.9%) as a solid. $^1H$ NMR ($CDCl_3$, 500 MHz): δ 5.45 (s, broad, 1H), 5.13 (m, 1H), 4.62-4.47 (m, 3H), 3.04 (s, 3H), 1.48 (s, 9H), 1.31 (d, J=6.4 Hz, 6H); $^{13}C$ NMR ($CDCl_3$, 100 MHz): δ 168.0, 135.1, 80.6, 70.5, 69.1, 53.3, 37.4, 28.3, 21.7, 21.6; HRMS m/z calcd. for $C_{12}H_{23}NO_7S$ 348.1087 (M+Na). found 348.1097

* preparation of 1 was reported in *J. Med. Chem.*, 2010, 53, 6825-6837 6825

Isopropyl 2-(tert-butoxycarbonylamino)-3-iodopropanoate (3)

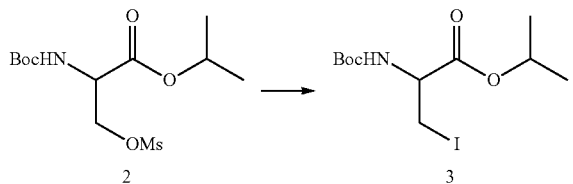 [SMILES: CC(C)OC(=O)C(COS(C)(=O)=O)NC(=O)OC(C)(C)C ; CC(C)OC(=O)C(CI)NC(=O)OC(C)(C)C]

To a solution of 2 (392 g) in acetone (3.14 L), sodium iodide (542 g) was added. The reaction temperature went up to 29° C. from 17° C. The reaction mixture was maintained at room temperature over weekend. The mixture was filtrated and washed with MTBE. The filtrate and washings were combined and concentrated. The residue was treated with MTBE and water with a small amount of sodium thiosulfate. The organic layer was washed with water and concentrated to an oil. The oil was charged slowly into a mixture of water (2 L) and DMF (300 ml) with a small amount of seed at 5° C. The crystals were filtered and dried to give 3 (400 g, 93% yield).

Isopropyl 4-(4-bromophenyl)-2-(tert-butoxycarbonylamino)-5-oxohexanoate (5) and isopropyl 4-phenyl-2-(tert-butoxycarbonylamino)-5-oxohexanoate (6)

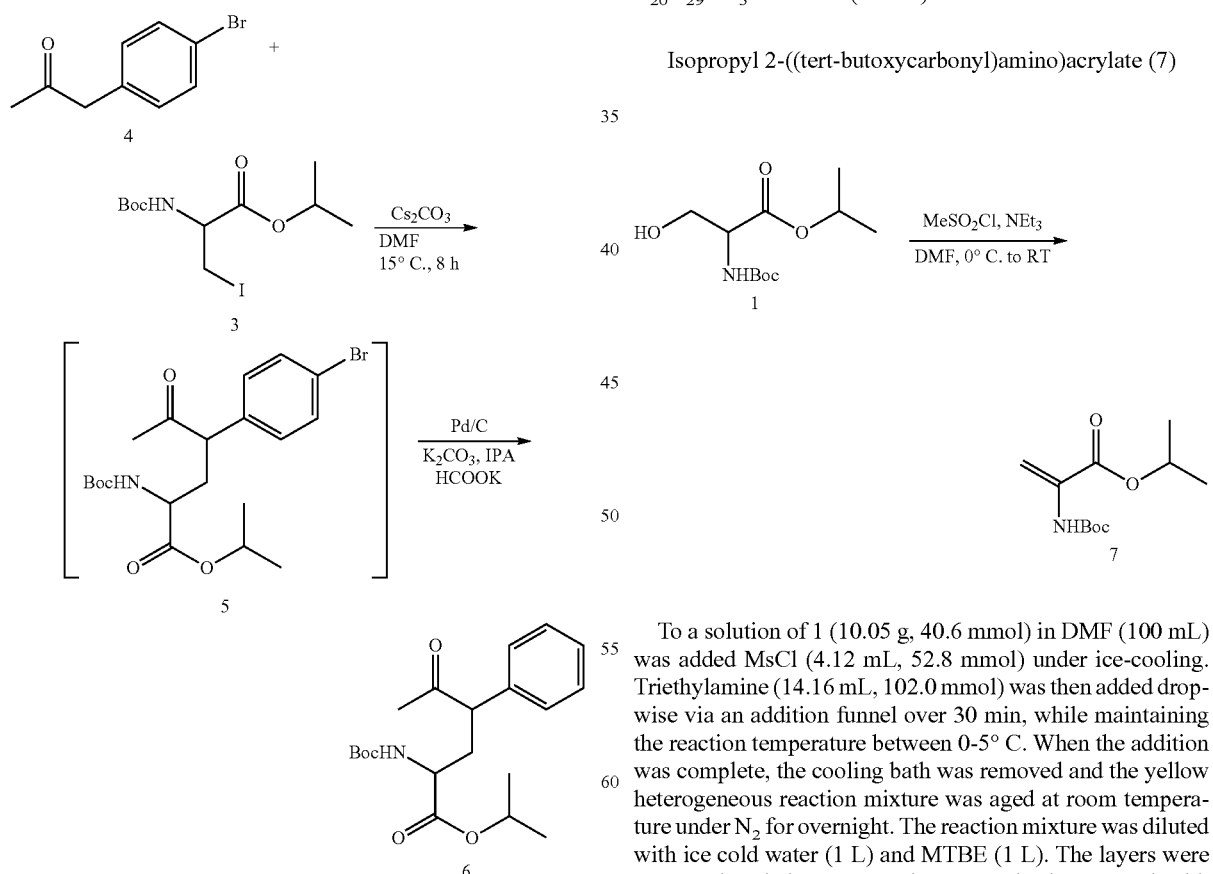

To a solution of 4 (51.7 g, 243 mmol) in DMF (850 ml) was added 3 (88 g, 246 mmol). The resulting solution was cooled to 5° C. and $Cs_2CO_3$ (240 g) was added in one portion. The suspension was warmed to 15° C. and stirred at this temperature for 2.5 h. Additional $Cs_2CO_3$ (25 g) was charged and the mixture was stirred for additional 8 h or until HPLC analysis indicated the conversion was greater than 95%. The batch was then slowly quenched into a mixture of 2N HCl (850 mL) and MTBE (900 mL) at 5-20° C. Organic layer was separated and aqueous layer extracted with MTBE (400 mL). Combined organic layers were washed with 5% $NaHCO_3$ solution (400 mL) twice. The resulting solution containing desired product 5 (90% LC purity) was concentrated under vacuum. The residue was dissolved in isopropanol (1 L). To the solution was added $K_2CO_3$ (25 g), potassium formate (34 g) and 10% Pd/C (20 g). The mixture was warmed up to 60° C. and stirred for 2 h. The mixture was filtered after cooling to room temperature. The HPLC analysis of the filtrate indicated that the solution contained 6 (54.7 g, 95 wt %, 62% yield). The crude product was used directly in the next step without further purification. The compound 6 is a mixture of two pair of diastereomers 6-1 and 6-2, partially separable by flash chromatography on silica gel with ethyl acetate and heptane as a eluant (1:10). 6-1: $^1H$ NMR ($CDCl_3$, 500 MHz): δ 7.35 (m, 2H), 7.30 (m, 1H), 7.20 (m, 2H), 5.17 (br, 1H), 4.95 (m, 1H), 4.76 (br, 1H), 3.73 (m, 1H), 2.70 (br, 1H), 2.07 (s, 1H), 1.45 (s, 9H), 1.29 (d, J=6.6 Hz, 3H), 1.28 (d, J=6.6 Hz, 3H); 6-2: $^1H$ NMR ($CDCl_3$, 500 MHz): δ 5.12 (m, 1H), 4.70 (m, 1H), 3.27 (m, 1H), 2.80 (m 1H), 2.34 (s, 3H), 1.50 (s, 9H), 1.26 (d, J=6.6 Hz, 3H), 1.25 (d, J=6.6 Hz, 3H); HRMS m/z: calcd. for 6-1: $C_{20}H_{29}NO_5$ 386.1938 (M+Na). found 386.1947.

Isopropyl 2-((tert-butoxycarbonyl)amino)acrylate (7)

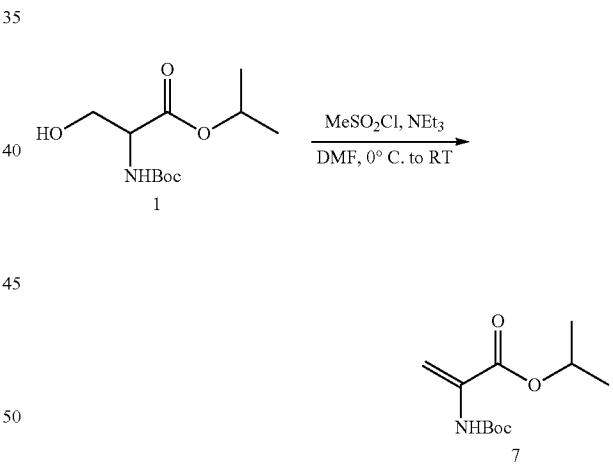

To a solution of 1 (10.05 g, 40.6 mmol) in DMF (100 mL) was added MsCl (4.12 mL, 52.8 mmol) under ice-cooling. Triethylamine (14.16 mL, 102.0 mmol) was then added dropwise via an addition funnel over 30 min, while maintaining the reaction temperature between 0-5° C. When the addition was complete, the cooling bath was removed and the yellow heterogeneous reaction mixture was aged at room temperature under $N_2$ for overnight. The reaction mixture was diluted with ice cold water (1 L) and MTBE (1 L). The layers were separated and the aqueous layer was back-extracted with MTBE (500 mL). The organic layers were combined and washed with 1M citric acid (750 mL), water (1 L) and then 10% aqueous NaCl (1 L). The organic solution contained 7

(8.652 g, 93% yield). Solvent was switched to DMSO at <40° C. and use solution directly in next step.

Isopropyl 4-phenyl-2-(tert-butoxycarbonylamino)-5-oxohexanoate (6)

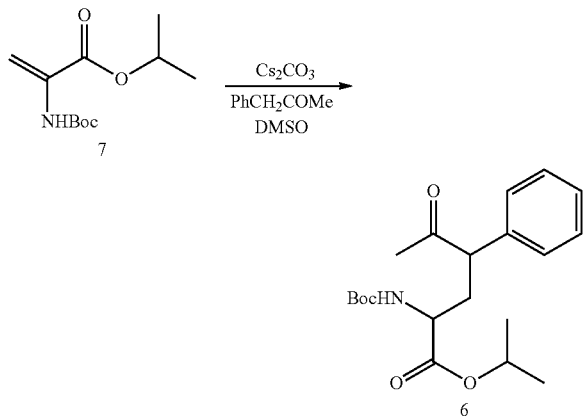

Compound 6 was prepared from 7 in DMSO in the presence of 0.5 equiv. Cs$_2$CO$_3$ with 1.05 equiv. of phenylacetone at room temperature in 79% yield.

tert-Butyl (5S,6R)-6-methyl-2-oxo-5-phenylpiperidin-3-ylcarbamate (8)

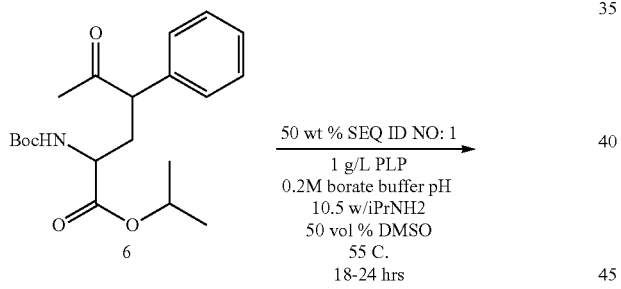

To a 5 L RBF with overhead stirring, a temperature control, a pH probe and a base addition line, was added sodiumtetraborate decahydrate (26.7 g) and DI water (1.4 L). After all solids were dissolved, isopropylamine (82.8 g) was added. The pH of the buffer was adjusted to pH 10.5 using 6 N HCl. The buffer was cooled to room temperature. Then, pyridoxal-5-phosphate (2.8 g) and SEQ ID NO: 1 (70 g) were added and slowly dissolved at room temperature.

An oil (197.9 g, containing 70.7 wt % keto ester 6 (140 g, 0.385 mol) were dissolved in DMSO (1.4 L). The solution was added to the flask over 5-10 min and the reaction was heated to 55° C. The pH was adjusted to 10.5 according to a handheld pH meter and controlled overnight with an automated pH controller using 8 M aqueous isopropylamine. The reaction was aged for 24 h.

After confirmation of >95 A % conversion by HPLC, the reaction was extracted by first adding a mixture of iPA:IPAc (3:4, 2.8 L) and stirring for 20 min. The phases were separated and the aqueous layer was back extracted with a mixture of iPA:IPAc (2:8, 2.8 L). The phases were separated, the organic layers were combined and washed with DI water (0.5 L). The HPLC based assay yield in the organic layer was 8 (114.6 g) with >60:1 dr at the positions C5 and C6. The ratio of stereoisomers at position C2 was ~1:1. The extract was concentrated and dissolved in CH$_2$Cl$_2$. The organic solution was washed with water then saturated aqueous NaCl, concentrated and crystallized from MTBE/n-hexane (2:3). The crystal was filtered at room temperature and washed with MTBE/n-hexane (2:3) and dried to afford a cis and trans mixture (~1:1.2) of the lactam 8 (99.6 g, 80.0%) as crystals.

cis: trans (~1:1.2) mixture but NMR integration was reported as 1:1 (for proton number counts) Mp 87-90.9° C.; $^1$H NMR (CDCl$_3$, 400 MHz): δ 7.40-7.20 (m, 8H, cis and trans), 7.16-7.12 (m, 2H, cis and trans); 6.56 (broad s, 1H, trans), 6.35 (broad s, 1H, cis), 5.57 (broad d, J=4.6 Hz, 1H, cis), 5.34 (broad d, J=5.7 Hz, 1H, trans), 4.33-4.15 (m, 2H, cis and trans), 3.93 (m, 1H, trans), 3.81 (m, 1H, cis), 3.41 (dt, J=11.8, 5.0 Hz, 1H, cis), 3.29 (dt, J=8.0, 4.4 Hz, 1H, trans), 2.74 (m, 1H, cis), 2.57 (m, 1H, trans), 2.23 (ddd, J=13.5, 8.0, 4.4 Hz, trans), 2.07 (q, J=11.8 Hz, 1H, cis), 1.46 (s, 9H, cis), 1.42 (s, 9H, trans), 1.05 (d, J=6.9 Hz, 3H, trans), 0.89 (d, J=6.9 Hz, 3H, cis); $^{13}$C NMR (CDCl$_3$, 100 MHz): δ 171.5$_2$ (cis), 171.4$_6$ (trans), 156.0$_4$ (cis or trans), 155.9$_3$ (cis or trans), 140.8 (cis), 139.9 (trans), 128.8 (trans), 128.7 (cis), 128.6 (trans), 128.1 (cis), 127.2$_5$ (trans), 127.1$_8$ (cis), 79.9$_8$ (trans), 79.9$_1$ (cis), 52.4 (trans), 51.8 (broad, cis), 51.7 (cis), 49.0 (broad, trans), 42.1 (trans), 41.9 (trans), 32.4 (broad, trans), 30.1 (cis), 28.5$_7$ (cis or trans), 28.5$_3$ (cis or trans), 18.3 (cis), 18.1 (broad, trans); HRMS m/z calcd. for C$_{17}$H$_{24}$N$_2$O$_3$ 327.1679 (M+Na). found 327.1696 tert-Butyl (5S,6R)-6-methyl-2-oxo-5-phenyl-1-(2,2,2-trifluoroethyl)piperidine-3-ylcarbamate (9) and tert-butyl (5S,6R)-6-methyl-2-oxo-5-phenyl-1-(2,2,2-trifluoroethyl)piperidine-3-yl(2,2,2-trifluoroethyl)carbamate (10)

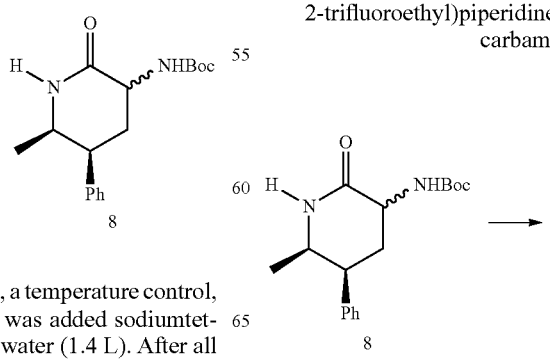

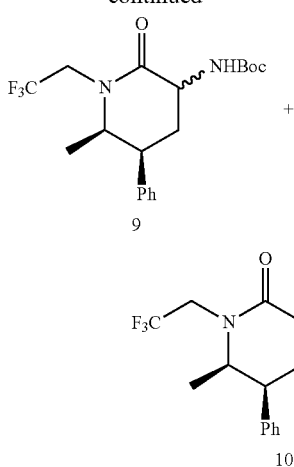

9

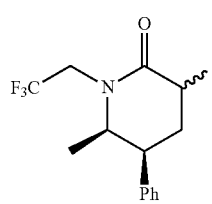

10

To the solution of 8 (480 g, 1.58 mol) in anhydrous THF (3.8 L) was added lithium tert-amoxide solution in heptane (512 mL, 3.1 M, 1.58 mol) over about 15 min while maintaining the reaction temperature between 15 and 20° C. The resulting solution was then cooled to a temperature between 0 and 2° C. 2,2,2-Trifluoroethyl trifluoromethanesulfonate (368 g, 1.58 mol) was added over 15 min while maintaining the reaction temperature between 0 and 3° C. The solution was agitated at 0° C. for 15 min. DMPU (300 ml) was charged to the mixture through an additional funnel over 30 min while maintaining the reaction temperature between 0 and 3° C. The resulting solution was agitated at 0° C. for 2.5 h. Another 2,2,2-trifluoroethyl trifluoromethanesulfonate (182 g, 0.79 mol) was added to the mixture over 10 min followed by another 3.1 M lithium tert-amoxide solution (104 mL) while maintaining the reaction temperature between 0 and 3° C. The batch was agitated for another 2.5 h at 0° C. The mixture was quenched into a mixture of heptane (4.8 L), water (3.4 L) and 2N HCl solution (280 mL) below 15° C. The phases were separated. The aqueous phase was extracted with heptane (4 L). The combined organic phase was washed with water (2 L). The solution was concentrated to a volume of about 1 L under vacuum between 25 and 50° C. The crude material was passed through a short silica gel plug with heptane/ethyl acetate. The resulting solution was concentrated under vacuum until distillation stopped at a temperature below 50° C., dissolved in IPAc (2 L) and used for the next processing step. The assay yield of 9 for both cis and trans isomers was 85% in the ratio of ~8 to 1.

Analytically pure cis and trans isomers of 9 were isolated by chromatography on silica gel with ethyl acetate and heptane as eluant. 9 (cis): $^1$H NMR (CDCl$_3$, 500 MHz): δ 7.30 (m, 5H), 5.75 (s, broad, 1H), 4.35 (m, 1H), 4.15 (m, 1H), 3.80 (m, 1H), 3.50 (m, 1H), 3.17 (m, 1H), 2.45 (m, 2H), 1.45 (s, 9H), 0.93 (d, J=6.7 Hz, 3H); $^{13}$C NMR (CDCl$_3$, 100 MHz): δ 170.3, 155.9, 140.0, 128.6, 127.6, 127.1, 124.6 (q, J=279 Hz), 79.7, 58.7, 52.2, 45.3 (q, J=33.7 Hz), 41.9, 28.3, 27.4, 13.4; HRMS: m/z calcd for C$_{19}$H$_{25}$F$_3$N$_2$O$_3$ 387.1890 (M+H). found: 387.1899. 9 (trans): $^1$H NMR (CDCl$_3$, 500 MHz): δ 7.40 (m, 2H), 7.30 (m, 3H), 5.55 (br, 1H), 4.53 (br, 1H), 4.45 (m, 1H), 3.78 (m 2H), 3.45 (m, 1H), 3.0 (m, 1H), 2.12 (m, 1H), 1.46 (s, 9H), 1.12 (d, J=7.0 Hz, 3H); $^{13}$C NMR (CDCl$_3$, 100 MHz): δ 170.2, 155.9, 139.6, 128.7, 127.9, 127.4, 124.3 (q, J=279 Hz), 80.0, 59.6, 49.1, 46.9 (q, J=34.0 Hz), 42.1, 28.3, 25.3, 13.4; HRMS: m/z calcd for C$_{19}$H$_{25}$F$_3$N$_2$O$_3$ 387.1890 (M+H). found 387.1901.

(3S,5S,6R)-6-Methyl-2-oxo-5-phenyl-1-(2,2,2-trifluoroethyl)piperidine-3-aminium 4-nitrobenzoate (11)

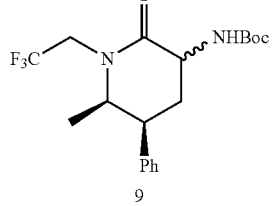

9

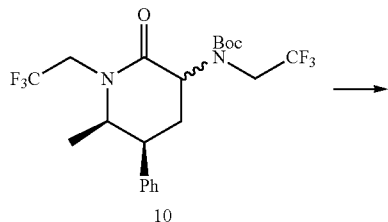

10

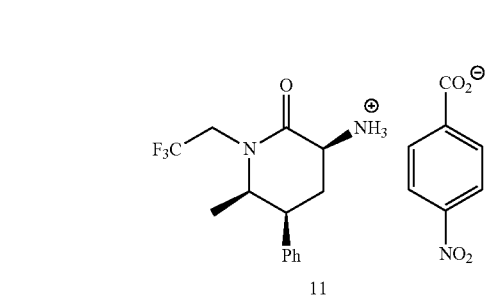

11

To a solution of the crude 9 obtained from above experiment (10 g assay, 25.9 mmol) in iPAC (8 ml) was added p-toluenesulfonic acid monohydrate (6.7 g, 35.2 mmol) and the mixture was stirred at 50-60° C. for 3 hr until the reaction was completed (>99%). The solution was cooled to 15-20° C., and washed with 10% aqueous K$_2$CO$_3$ followed by water. The aqueous layers were re-extracted with iPAc (5 ml). The organic layers were combined and heated to 55-60° C. 4-Nitrobenzoic acid (3.9 g, 23.2 mmol) was slowly added in 20 min. The mixture was slowly cooled to room temperature. 5-Nitro-2-hydroxylbenzaldehyde (50 mg) was added and the batch was agitated for at least 12 h. The mixture was filtrated and washed with MeCN to give 11 as crystals. Optionally, a slurry in MeCN was carried out for further purification of 11. The isolated yield was 90%. Mp 205-208° C.; $^1$H NMR (DMSO-d$_6$, 400 MHz): δ 8.21 (dd, J=9.0, 2.1 Hz, 2H), 8.08 (dd, J=9.0, 2.1 Hz, 2H), 7.37 (t, J=7.4 Hz, 2H), 7.28 (t, J=7.4 Hz, 1H), 7.24 (d, J=7.4 Hz, 2H), 4.65 (ddd, J=15.1, 9.7, 7.7 Hz, 1H), 3.72-3.98 (m, 3H), 3.57 (m, 1H), 2.46 (q, J=12.6 Hz, 1H), 2.25 (m, 1H), 0.90 (d, J=6.4 Hz, 3H); $^{19}$F NMR (DMSO-d$_6$, 376 MHz): δ −69 (s); $^{13}$C NMR (DMSO-d$_6$, 100 MHz): δ 168.7, 167.3, 148.3, 143.8, 140.1, 130.1, 128.6, 127.4, 127.0, 124.9 (q, J=280.9 Hz), 122.8, 58.7, 49.8, 44.5 (q, J=32.7 Hz), 40.6, 25.3, 13.2.

(5S,6R)-3-Amino-6-methyl-5-phenyl-1-(2,2,2-trifluoroethyl)piperidin-2-one (12)

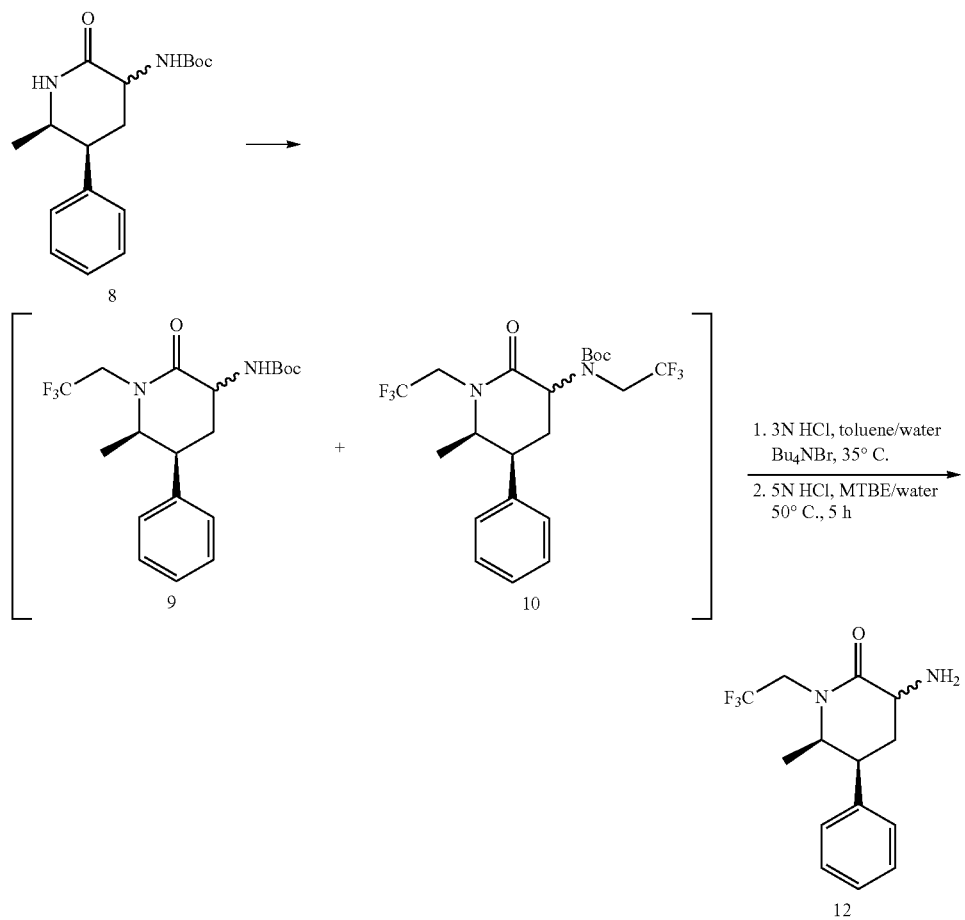

To a mixture of 8 (20.0 g, 65.7 mmol) and Na$_2$S$_2$O$_3$ (0.52 g, 3.3 mmol) in THF (200 mL) was added tert-BuOLi (6.8 g, 85 mmol) at 16° C. The mixture was stirred at 16° C. for 15 min followed by addition of trifluoroethyl trifluoromethansulfonate (20.6 g, 89 mmol) in one portion. The resulting mixture was stirred for 18 h at 16° C. The reaction mixture was then quenched by addition of toluene (70 mL) followed by 0.5N HCl solution (50 mL). The aqueous layer was separated and extracted with toluene (20 mL). The combined organic layer contained 87% of 9, 6% of 10 and 6% of 8 by HPLC and yield for the desired product 9 was 87%. The organic layer was then stirred with 3N HCl solution (80 ml) and tetrabutylammoniium bromide (0.8 g) for about 3 h until HPLC analysis indicated selective removal of the Boc group in the unreacted 8 was completed. The aqueous layer was removed. The organic layer containing 9 and 10 was then concentrated under vacuum at 60° C. to remove most of solvent. The residue was dissolved in MTBE (60 mL), and 5N HCl solution (65 mL) was added. The diphasic solution was agitated vigorously at 50° C. for about 5 h until the deprotection of 9 was completed while 10 was mainly intact. After addition of heptane (30 mL) to the mixture, the organic layer was separated at 45° C. The aqueous layer was diluted with water (60 mL) and resulting aqueous and washed with heptane (30 mL) at 45° C. The aqueous solution was then mixed with MTBE (100 mL) and basified with 10 N NaOH solution until the pH of the mixture was about 10. The organic layer was separated and the aqueous layer was back-extracted with MTBE (60 mL). The combined organic layers were washed with brine (60 mL). The resulting organic solution was suitable for next reaction. The solution was contained 12 (15.6 g, 83% from 8) with 97% LC purity as a mixture of two diastereomers (cis and trans) in 4 to 1 ratio.

(3S,5S,6R)-6-Methyl-2-oxo-5-phenyl-1-(2,2,2-trifluoroethyl)piperidin-3-aminium 4-methylbenzoate (13)

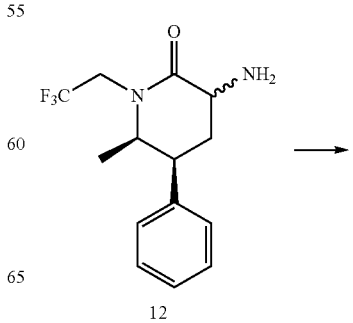

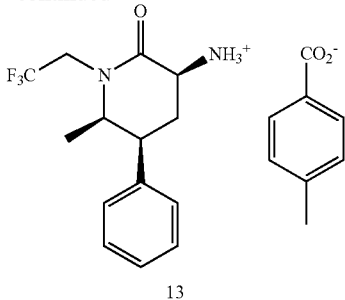

To a suspension of 4-methylbenzoic acid (6.8 g, 49.9 mmol) and 3,5-dichlorosalicylaldehyde (93 mg, 0.49 mmol) in MTBE (40 mL) was added a solution of 12 (13.9 g, 48.5 mmol) in MTBE (about 150 mL) over 1 h at 50° C. The resulting suspension was agitated for about 3 h at 50° C. The solids were collected by filtration after cooling to −5° C. over 1 h. The cake was washed with MTBE (50 mL). The solids were dried in a vacuum oven to give 13 (17.6 g, 86%) as crystals with 99.5% LC purity and 99.6% de. $^1$H NMR (DMSO-d$_6$, 400 MHz): δ 7.85 (d, J=8.1 Hz, 2H), 7.40 (m, 2H), 7.25 (m, 5H), 6.0 (br, 3H), 4.65 (m, 1H), 3.65-3.80 (m, 2H), 3.45-3.65 (m, 2H), 2.35 (s, 3H), 2.30 (m, 1H), 2.15 (m, 1H), 0.88 (d, J=6.5 Hz, 3H); $^{13}$C NMR (DMSO-d$_6$, 100 MHz): δ 172.4, 168.5, 142.1, 141.1, 130.9, 129.7, 129.2, 129.0, 128.0, 125.5 (q, J=279 Hz), 59.1, 51.6, 45.1 (q, J=32 Hz), 41.6, 28.0, 21.5, 13.9.

(S)—N-((3S,5S,6R)-6-Methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide trihydrate (15)

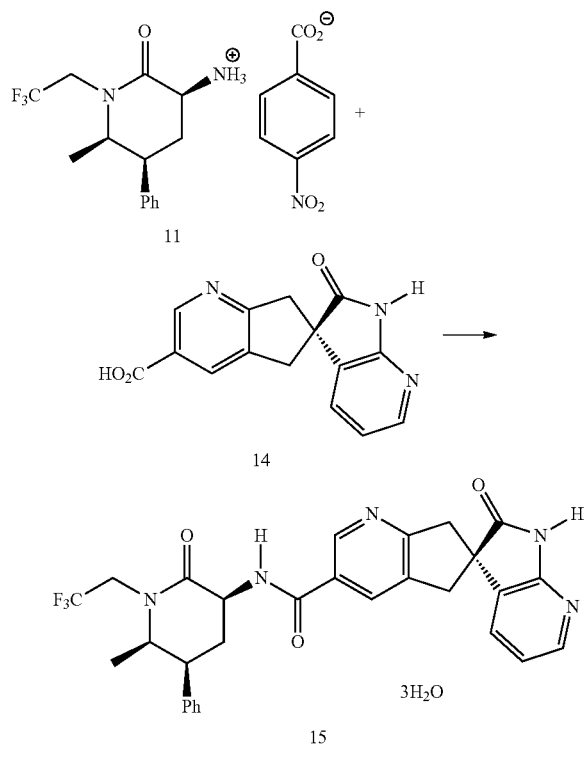

To a suspension of 11 (465 g, 96% wt, 0.99 mol) in iPAc (4.6 L) was added 5% aqueous K$_3$PO$_4$ (4.6 L). The mixture was stirred for 5 min. The organic layer was separated and washed with 5% aqueous K$_3$PO$_4$ (4.6 L) twice and concentrated in vacuo and dissolved in acetonitrile (1.8 L).

To another flask was added 14 (303 g, 91.4 wt %), acetonitrile (1.8 L) and water (1.8 L) followed by 10 N NaOH (99 mL). The resulting solution was stirred for 5 min at room temperature and the chiral amine solution made above was charged to the mixture and the container was rinsed with acetonitrile (900 mL). HOBT hydrate (164 g) was charged followed by EDC hydrochloride (283 g). The mixture was agitated at room temperature for 2.5 h. To the mixture was added iPAc (4.6 L) and organic layer was separated, washed with 5% aqueous NaHCO$_3$ (2.3 L) followed by a mixture of 15% aqueous citric acid (3.2 L) and saturated aqueous NaCl (1.2 L). The resulting organic layer was finally washed with 5% aqueous NaHCO$_3$ (2.3 L). The organic solution was concentrated below 50° C. and dissolved in methanol (2.3 L). The solution was slowly added to a mixture of water (6 L) and methanol (600 mL) with ~2 g of seed crystal. And the resulting suspension was stirred overnight at room temperature. Crystals were filtered, rinsed with water/methanol (4 L, 10:1), and dried under nitrogen flow at room temperature to provide 15 (576 g, 97% yield) as trihydrate.

$^1$H NMR (500 MHz, CDCl$_3$): δ 10.15 (br s, 1H), 8.91 (br s, 1H), 8.21 (d, J=6.0 Hz, 1H), 8.16 (dd, J=5.3, 1.5 Hz, 1H), 8.01 (br s, 1H), 7.39-7.33 (m, 2H), 7.31-7.25 (m, 1H), 7.22-7.20 (m, 2H), 7.17 (dd, J=7.4, 1.6 Hz, 1H), 6.88 (dd, J=7.4, 5.3 Hz, 1H), 4.94 (dq, J=9.3, 7.6 Hz, 1H), 4.45-4.37 (m, 1H), 3.94-3.87 (m, 1H), 3.72 (d, J=17.2 Hz, 1H), 3.63-3.56 (m, 2H), 3.38-3.26 (m, 1H), 3.24 (d, J=17.3 Hz, 1H), 3.13 (d, J=16.5 Hz, 1H), 2.78 (q, J=12.5 Hz, 1H), 2.62-2.56 (m, 1H), 1.11 (d, J=6.5 Hz, 3H); $^{13}$C NMR (126 MHz, CD$_3$CN): δ 181.42, 170.63, 166.73, 166.63, 156.90, 148.55, 148.08, 141.74, 135.77, 132.08, 131.09, 130.08, 129.66, 129.56, 128.78, 128.07, 126.25 (q, J=280.1 Hz), 119.41, 60.14, 53.07, 52.00, 46.41 (q, J=33.3 Hz), 45.18, 42.80, 41.72, 27.79, 13.46; HRMS m/z: calcd for C$_{29}$H$_{26}$F$_3$N$_5$O$_3$ 550.2061 (M+H). found 550.2059.

Alternative procedure for 15:

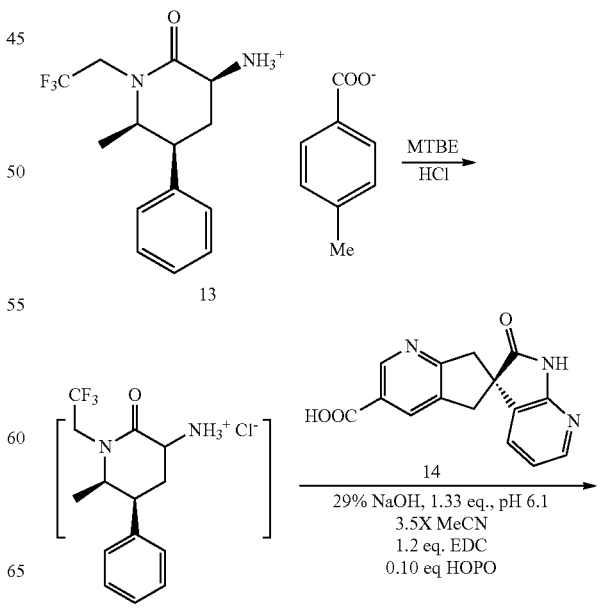

-continued

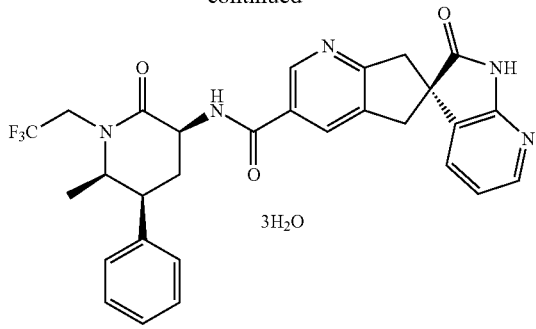

15

To a suspension of 13 (10 g, 98 wt %, 23.2 mmol) in MTBE (70 mL) was added 0.6 N HCl (42 mL). The organic layer was separated and extracted with another 0.6 N HCl (8 mL). The combined aqueous solution was washed with MTBE (10 mL×3). To the resulting aqueous solution was added acetonitrile (35 mL) and 14 (6.66 g, 99 wt %). To the resulting suspension was neutralized with 29% NaOH solution to pH 6. HOPO (0.26 g) was added followed by EDC hydrochloride (5.34 g). The mixture was stirred at room temperature for 6-12 h until the conversion was complete (>99%). Ethanol (30 ml) was added and the mixture was heated to 35° C. The resulting solution was added over 2 h to another three neck flask containing ethanol (10 mL), water (30 mL) and 15 seeds (0.4 g). Simultaneously, water (70 mL) was also added to the mixture. The suspension was then cooled to 5° C. over 30 min and filtered. The cake was washed with a mixture of ethanol/water (1:3, 40 mL). The cake was dried in a vacuum oven at 40° C. to give 15 trihydrate (13.7 g, 95%) as crystals.

Example 2

N-Methoxy-N-methyl-2-(2,3,6-trifluorophenyl)acetamide (17)

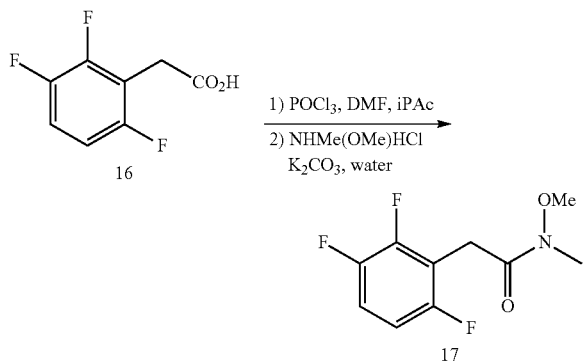

To a solution of DMF (58.1 mL, 750 mmol) in iPAc (951 mL) was added POCl₃ (55.9 mL, 600 mmol) under ice-cooling. After aged for 1 h under ice-bath, acid 16 (95 g, 500 mmol) was added under ice-cooling. The solution was stirred under ice-cooling for 30 min. The solution was added over 30 min into a solution of K₂CO₃ (254 g, 1.835 mol) and NHMe(OMe)HCl (73.2 g, 750 mmol) in water (951 mL) below 8° C. After aged for 30 min below 8° C., the organic layer was separated, washed with water (500 mL) twice and sat. NaCl aq (100 mL) once, and concentrated in vacuo to afford 17 as an oil (117.9 g, 97.7 wt %, 99% yield).

¹H NMR (CDCl₃, 400 MHz); δ 7.05 (m, 1H), 6.82 (m, 1H), 3.86 (s, 2H), 3.76 (s, 3H), 3.22 (s, 3H); ¹⁹F NMR (CDCl₃, 376.6 MHz); δ −120.4 (dd, J=15.1, 2.7 Hz), −137.9 (dd, J=20.8, 2.7 Hz), −143.5 (dd, J=20.8, 15.1 Hz); ¹³C NMR (CDCl₃, 100 MHz); δ 169.4, 156.9 (ddd, J=244, 6.2, 2.7 Hz), 149.3 (ddd, J=249, 14.4, 8.4 Hz), 147.1 (ddd, J=244, 13.1, 3.5 Hz), 115.5 (ddd, J=19.4, 9.9, 1.5 Hz), 133.4 (dd, J=22.3, 16.4 Hz), 110.2 (ddd, J=24.8, 6.7, 4.1 Hz), 32.4 (broad), 26.6 (m); HRMS m/z calcd for $C_{10}H_{10}F_3NO_2$ 234.0736 (M+H). found 234.0746

1-(2,3,6-Trifluorophenyl)propan-2-one (18)

A mixture of CeCl₃ (438 g, 1779 mmol) and THF (12 L) was heated at 40° C. for about 2 h then cooled to 5° C. Methylmagensium chloride in THF (3 M, 3.4 L) was charged at 5-9° C. and then it was warmed up to 16° C. and held for 1 h. The suspension was re-cooled to −10 to −15° C. A solution of 17 (1.19 kg) in THF (2.4 L) was charged into the suspension over 15 min. After confirmation of completion of the reaction, the reaction mixture was transferred to a cold solution of hydrochloric acid (2 N, 8.4 L) and MTBE (5 L) in 5-10° C. The aqueous phase was separated and the organic layer was washed with aqueous 5% K₂CO₃ (6 L) and then 10% aqueous NaCl (5 L). The organic layer was dried over Na₂SO₄, concentrated to give crude 18 (917 g, >99 wt %) in 95% yield. The crude 18 was used in the next step without further purification. Analytically pure 18 was obtained by silica gel column.

¹H NMR (CDCl₃, 400 MHz); δ 7.07 (m, 1H), 6.84 (m, 1H), 3.82 (s, 2H), 2.28 (s, 3H); ¹⁹F NMR (CDCl₃, 376.6 MHz); δ −120.3 (dd, J=15.3, 2.5 Hz), −137.8 (dd, J=21.2, 2.5 Hz), −143.0 (dd, J=20.2, 15.3 Hz); ¹³C NMR (CDCl₃, 100 MHz); δ 202.2, 156.5 (ddd, J=244, 6.3, 2.9 Hz), 148.9 (ddd, J=249, 14.4, 8.6 Hz), 147.0 (ddd, J=244, 13.1, 3.5 Hz), 115.7 (ddd, J=19.4, 10.5, 1.2 Hz), 112.8 (dd, J=22.7, 17.0 Hz), 110.3 (ddd, J=24.8, 6.7, 4.1 Hz), 37.2 (d, J=1.2 Hz), 29.3.

Isopropyl 2-((tert-butoxycarbonyl)amino)-5-oxo-4-(2,3,6-trifluorophenyl)hexanoate (19)

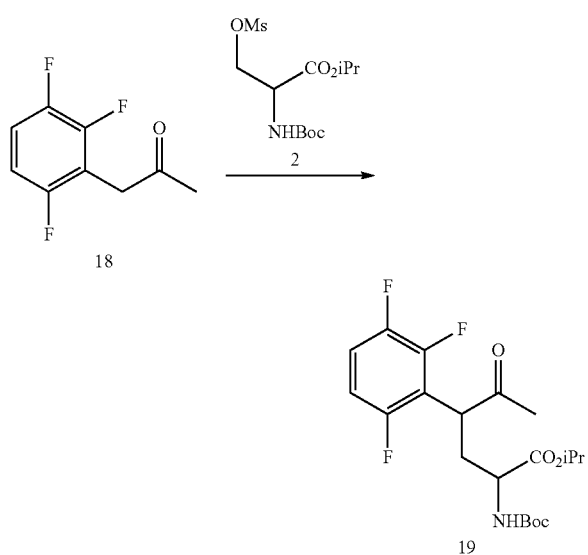

To a solution of 18 (195 g, 1.03 mol) in MTBE (1.8 L) was added zinc bromide (67 g, 0.30 mol) followed by 2 (390 g, 1.2 mol). tert-BuOLi (290 g, 3.6 mol) was then added in several portions while maintaining the reaction temperature below 40° C. The resulting mixture was stirred at 35° C. for 24 h and quenched into a mixture of 2 N HCl (5.6 L) and heptane (5 L) at 0° C. The organic layer was separated and washed with 5% aqueous NaHCO₃ (5 L) twice. The resulting organic solution was concentrated under vacuum. The residue was dissolved in heptane (2 L) and the solution was concentrated again under vacuum. The resulting oil was dissolved in DMSO (2.5 L) and the solution was used in the next step without further purification. HPLC analysis indicated that the solution contained the desired product 19 (290 g, 67% yield) as the major component along with 5% of starting material 18. The analytically pure product 19 as one pair of diastereomers was isolated by chromatography on silica gel with ethyl acetate and heptane mixture as an eluant. HRMS: m/z calcd for $C_{20}H_{26}F_3NO_5$ 418.1836 (M+H). found 418.1849.

tert-Butyl ((5S,6R)-6-methyl-2-oxo-5-(2,3,6-trifluorophenyl)piperidin-3-yl)carbamate (20)

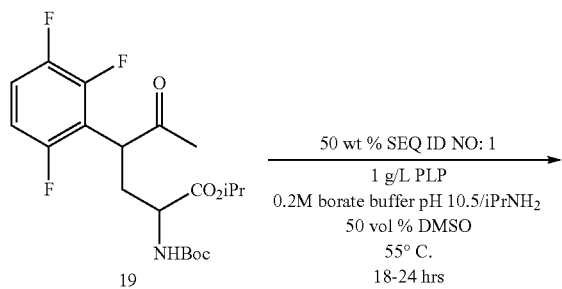

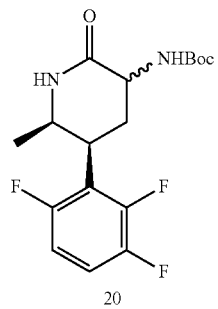

To a 0.5 L cylindrical Sixfors reactor with an overhead stirring, a temperature control, a pH probe and a base addition line, was added sodiumtetraborate decahydrate (3.12 g) and DI water (163 mL). After all solids were dissolved, isopropylamine (9.63 g) was added. The pH of the buffer was adjusted to pH 10.5 using 6 N HCl. The buffer was cooled to room temperature. Then, pyridoxal-5-phosphate (0.33 g) and SEQ ID NO: 1 (8.15 g) were added and slowly dissolved at room temperature.

Crude keto ester 19 (23.6 g, 69 wt %, 16.3 g assay, 39 mmol) was dissolved in DMSO (163 mL) and the solution was added to the reactor over 5-10 min. Then the reaction was heated to 55° C. The pH was adjusted to 10.5 according to a handheld pH meter and controlled overnight with an automated pH controller using 8 M aqueous isopropylamine. The reaction was aged for 27.5 hours.

After confirmation of >95 A % conversion by HPLC, the reaction was extracted by first adding a mixture of iPA: iPAc (3:4, 350 mL) and stirring for 20 min. The phases were separated and the aqueous layer was back extracted with a mixture of iPA: iPAc (2:8, 350 mL). The phases were separated. The organic layers were combined and washed with DI water (90 mL). The HPLC based assay yield in the organic layer was 20 (9.86 g, 70.5% assay yield) with >60:1 dr at the positions C5 and C6.

tert-Butyl ((3S,5S,6R)-6-methyl-2-oxo-5-(2,3,6-trifluorophenyl)piperidin-3-yl)carbamate (21)

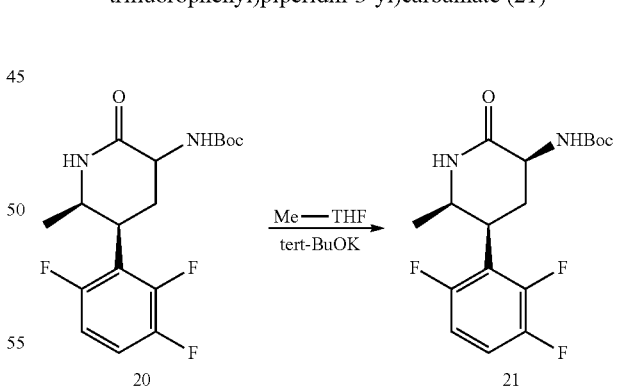

A solution of crude cis and trans mixture 20 in a mixture of iPAc and iPA (1.83 wt %, 9.9 kg; 181 g assay as a mixture) was concentrated in vacuo and dissolved in 2-Me-THF (3.6 L). To the solution was added tert-BuOK (66.6 g, 0.594 mol) at room temperature. The suspension was stirred at room temperature for 2 h. The mixture was poured into water (3.5 L) and the organic layer was separated, washed with 15 wt % of aqueous NaCl (3.5 L), dried over Na₂SO₄, and concentrated to dryness. The residue was suspended with iPAc (275 mL) and heptane (900 mL) at 60° C. The suspension was slowly cooled down to 1° C. The solid was filtered and rinsed with iPAc and heptane (1:3), dried to afford 21 (166 g, 93 wt %; 85%) as crystals. Mp 176-179° C.; $^1$H NMR (CDCl$_3$, 500 MHz): δ 7.06 (m, 1H), 6.84 (m, 1H), 5.83 (broad s, 1H), 5.58 (broad s, 1H), 4.22 (m, 1H), 3.88-3.79 (m, 2H), 2.77 (m, 1H), 2.25 (m, 1H), 1.46 (s, 9H), 1.08 (d, J=6.4 Hz, 3H); $^{19}$F NMR (CDCl$_3$, 376 MHz): δ −117 (d, J=14 Hz), −135 (d, J=20 Hz), −142 (dd, J=20, 14 Hz); $^{13}$C NMR (CDCl$_3$, 100 MHz): δ 171.1, 156.6 (ddd, J=245, 6.4, 2.8 Hz), 155.8, 149.3 (ddd, J=248, 14.4, 8.8 Hz), 147.4 (ddd, J=245, 14.2, 3.8 Hz), 118.0 (dd, J=19.3, 14.5 Hz), 115.9 (dd, J=19.2, 10.4 Hz), 111.0 (ddd, J=26.4, 6.0, 4.3 Hz), 79.8, 51.4, 49.5, 34.1, 29.3, 28.3, 18.0; HRMS: m/z calcd for C$_{17}$H$_{21}$F$_3$N$_2$O$_3$ 381.1396 (M+Na). found 381.1410.

tert-Butyl ((5S,6R)-6-methyl-2-oxo-1-(2,2,2-trifluoroethyl)-5-(2,3,6-trifluorophenyl)piperidin-3-yl)carbamate (22)

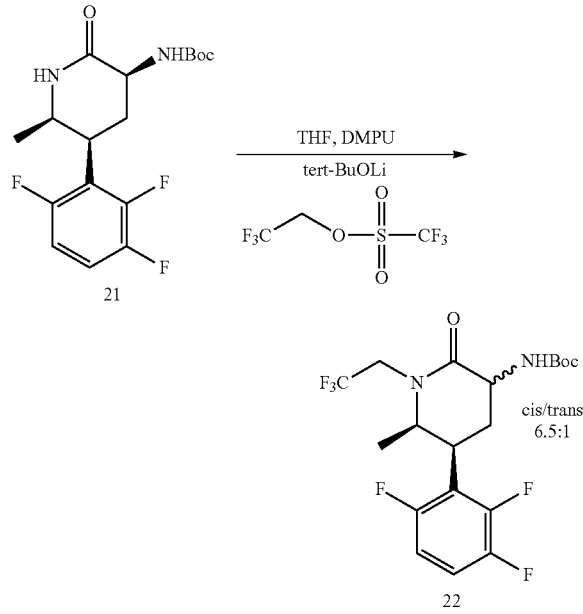

To a solution of 21 (10 g, 87% purity, 24.3 mmol) in THF (70 ml) was added tert-BuOLi (2.5 g, 31.2 mmol) at 5° C. in one portion. The solution was cooled to between 0 and 5° C. and trifluoroethyl trifluoromethanesulfonate (10.0 g, 43 mmol) was added in one portion. DMPU (7 mL) was added slowly over 15 min while maintaining the reaction temperature below 5° C. After the mixture was stirred at 0° C. for 3 h, additional tert-BuOLi (0.9 g, 11.2 mmol) was added. The mixture was aged for an additional 90 min. The mixture was quenched with 0.2 N HCl (70 ml), followed by addition of heptane (80 ml). The organic layer was separated and aqueous layer extracted with heptane (30 ml). The combined organic layers were washed with 15% aqueous citric acid (50 mL) and 5% aqueous NaHCO$_3$ (50 mL). The solution was concentrated under vacuum at 40° C. and the resulting oil was dissolved in iPAc (30 mL). The solution was used directly in the next step without further purification. The HPLC analysis indicated that the solution contained 22 (9.8 g, 92% as cis and trans mixture in a ratio of 6.5 to 1) along with 4% of starting material 21 and 8% of a N,N'-alkylated compound. Analytically pure 22 (cis isomer) was isolated by chromatography on silica gel with ethyl acetate and heptane as an eluant. $^1$H NMR (CDCl$_3$, 500 MHz): δ 7.15 (m, 1H), 6.85 (m, 1H), 5.45 (broad, s, 1H), 4.90 (m, H), 4.20 (m, 1H), 3.92 (m, 2H), 3.28 (m, 1H), 2.70 (m, 2H), 1.48 (s, 9H), 1.20 (d, J=5.9 Hz, 3H); $^{13}$C NMR (CDCl$_3$, 100 MHz): δ 170.2, 156.9 (ddd, J=245, 6.3, 2.7 Hz), 156.0, 149.6 (ddd, J=251, 14.8, 8.8 Hz), 147.6 (ddd, J=246, 13.9, 3.6 Hz), 124.5 (q, J=281 Hz), 117.6 (dd, J=19.2, 3.7 Hz), 116.4 (dd, J=19.1, 10.4 Hz), 111.4 (ddd, J=25.8, 6.4, 4.1 Hz), 56.6, 52.8, 45.3 (q, J=34.2 Hz), 35.2, 28.7, 28.3 (br t, J=4 Hz), 14.6; HRMS: m/z calcd for C$_{19}$H$_{22}$F$_6$N$_2$O$_3$ (M+H): 441.1607. found 441.1617.

(3S,5S,6R)-6-Methyl-2-oxo-1-(2,2,2-trifluoroethyl)-5-(2,3,6-trifluorophenyl)piperidin-3-aminium (S)-2-acetamido-3-phenylpropanoate (23)

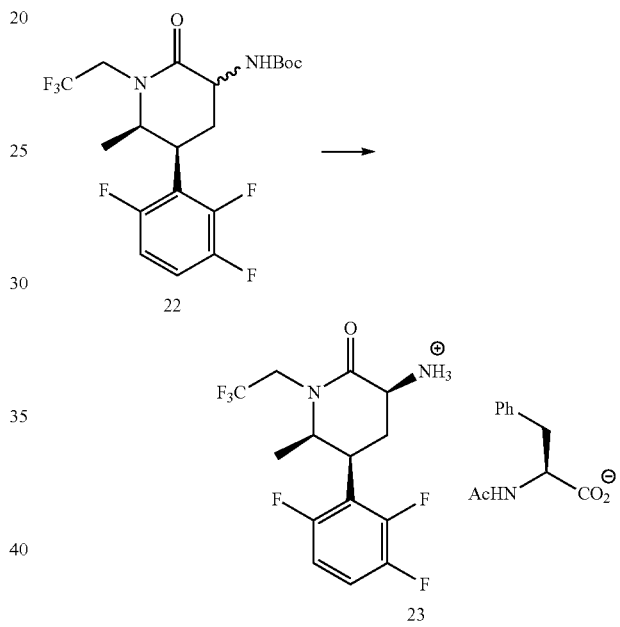

iPAc solution of 22 (529 g assayed, 1.2 mol), obtained from previous step, was diluted to 6 L with iPAc, p-toluenesulfonic acid monohydride (343 g, 1.8 mol) was added and the solution was heated to 55° C. After 4 h, the reaction completed (>99% conversion). Aqueous K$_2$CO$_3$ (530 g in 3 L of water) was charged into the solution after cooled to 15-25° C. The aqueous layer was separated and was back-extracted with iPAc (2 L). The iPAc solutions were combined and the total volume was adjusted to 10 L by adding iPAc. The solution was heated to 50-60° C. About 20 g of N-acetyl L-phenylalanine was added and the solution was agitated for 15 min or until solids precipitated out. The remaining N-acetyl L-phenylalanine (total 250 g, 1.2 mol) was charged slowly and 2-hydroxy-5-nitrobenzaldehyde (2 g) was charged. The suspension was agitated for 12 h at 20° C. and then cooled to 0° C. for 3 h. The suspension was filtrated, washed with iPAc three times and dried to give 23 (583 g, 89% yield) as crystals. Mp 188-190° C.; $^1$H NMR (DMSO-d$_6$, 400 MHz): δ 7.96 (d, J=8.0 Hz, 1H), 7.48 (m, 1H), 7.15-7.25 (m, 6H), 4.65 (ddd, J=19.4, 15.3, 9.6 Hz, 1H), 4.33 (ddd, J=8.7, 8.4, 4.9 Hz, 1H), 3.70-3.87 (m, 3H), 3.57 (dd, J=11.5, 6.6 Hz, 1H), 3.04 (dd, J=13.7, 4.9 Hz, 1H), 2.82 (dd, J=13.7, 8.9 Hz, 1H), 2.59 (m, 1H), 2.24 (m, 1H), 2.95 (s, 3H), 1.10 (d, J=6.4 Hz, 1H); $^{19}$F NMR (DMSO-d$_6$, 376 MHz): δ −69 (s), −118 (d, J=15 Hz), −137 (d, J=21 Hz), −142 (dd, J=21, 15 Hz); $^{13}$C NMR (DMSO-d$_6$, 100 MHz): δ 173.6, 171, 0.1, 168.7, 156.3 (ddd, J=243.5, 7.0, 3.1 Hz), 148.7 (ddd, J=249, 14.4, 9.1 Hz), 146.8 (ddd, J=245, 13.7, 3.1 Hz), 138.5, 129.2, 128.0, 126.1, 124.9 (q, J=280.9 Hz), 117.4.0 (dd, J=19.3, 13.8 Hz), 116.7 (dd, J=19.3, 10.6 Hz), 111.8 (ddd, J=26.0, 6.7, 3.6 Hz), 56.6, 54.3, 51.2, 44.3 (q, J=32.5 Hz), 37.2, 34.8, 26.9 (br t, J=4 Hz), 22.5, 14.1.

(3S,5S,6R)-6-methyl-2-oxo-1-(2,2,2-trifluoroethyl)-5-(2,3,6-trifluorophenyl)piperidin-3-aminium 2,2-diphenylacetate (25)

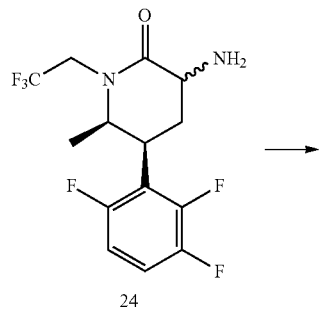

24

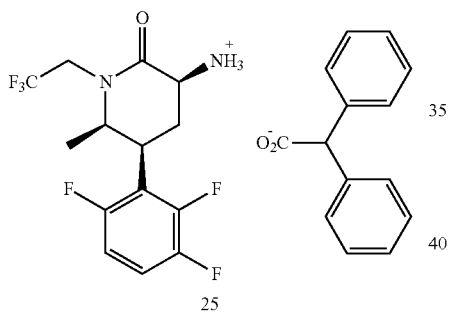

25

To a mixture of crude material containing (5S,6R)-3-amino-6-methyl-1-(2,2,2-trifluoroethyl)-5-(2,3,6-trifluorophenyl)piperidin-2-one (24, 2.00 g, 5.88 mmol), prepared according to the same method as the previous example, and 3,5-dichloro-2-hydroxybenzaldehyde (0.011 g, 0.059 mmol) in isopropyl acetate (15.0 ml) at 55-60° C. under nitrogen was slowly added a solution of diphenylacetic acid (1.26 g, 5.88 mmol) in THF (10.0 ml) over 2 h. Upon completion of acid addition, a thick salt suspension was agitated at 55-60° C. for another 18 h and then was allowed to cool to ambient temperature. The salt was filtered and washed with isopropyl acetate. After drying at 60° C. in a vacuum oven with nitrogen purge for 8 hours, 25 (2.97 g, 91.4%) was obtained as crystals. $^1$H NMR (500 MHz, DMSO-d$_6$): δ 7.48 (qd, J=9.4, 4.9 Hz, 1H), 7.32 (d, J=7.7 Hz, 4H), 7.25-7.26 (m, 4H), 7.19-7.17 (m, 3H), 6.79 (br, 3H), 4.95 (s, 1H), 4.67 (dq, J=15.3, 9.7 Hz, 1H), 3.81-3.79 (m, 3H), 3.62 (dd, J=11.6, 6.5 Hz, 1H), 2.66-2.62 (m, 1H), 2.25 (dd, J=12.9, 6.4 Hz, 1H), 1.11 (d, J=6.5 Hz, 3H); $^{13}$C NMR (100 MHz, DMSO-d$_6$): δ 174.4, 171.8, 156.9 (ddd, J=244, 7.0, 2.5 Hz), 149.1 (ddd, J=249, 14.4, 8.5 Hz), 147.2 (ddd, J=246, 13.9, 3.2 Hz), 141.4, 129.0, 128.5, 126.7, 125.5 (q, J=281 Hz), 118.0 (dd, J=19.8, 13.8 Hz), 117.1 (dd, J=19.2, 10.6 Hz), 112.3 (ddd, J=26.1, 6.7, 3.3 Hz), 58.5, 57.1, 51.7, 44.8 (q, J=32.7 Hz), 35.3, 27.5 (br t, J=4.6 Hz), 14.5.

(3S,5S,6R)-6-methyl-2-oxo-1-(2,2,2-trifluoroethyl)-5-(2,3,6-trifluorophenyl)piperidin-3-aminium 1H-indole-2-carboxylate (26)

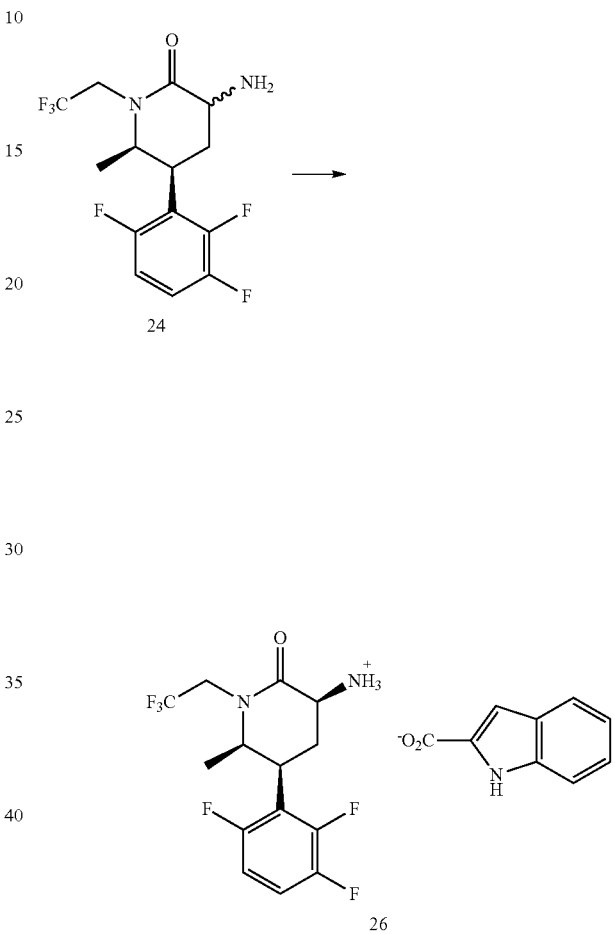

To a mixture of crude material containing 24 (2.00 g, 5.88 mmol) and 3,5-dichloro-2-hydroxybenzaldehyde (0.011 g, 0.059 mmol) in isopropyl acetate (15.0 ml) at 55-60° C. under nitrogen was slowly added a solution of 1H-indole-2-carboxylic acid (0.96 g, 5.88 mmol) in THF (10.0 ml) over 2 hours. Upon completion of acid addition, a thick salt suspension was agitated at 55-60° C. for another 18 h and then was allowed to cool to ambient temperature. The salt was filtered and washed with isopropyl acetate. After drying at 60° C. in a vacuum oven with nitrogen purge for 8 h, 26 (2.33 g, 79.0%) was isolated as crystals. $^1$H NMR (500 MHz, DMSO): δ 11.40 (s, 1H), 7.56 (d, J=8.0 Hz, 1H), 7.45 (br, 3H), 7.47 (ddd, J=14.8, 10.1, 8.3 Hz, 1H), 7.41-7.40 (m, 1H), 7.16-7.14 (m, 2H), 6.98-6.97 (m, 1H), 6.87 (s, 1H), 4.69 (dq, J=15.3, 9.6 Hz, 1H), 3.84-3.81 (m, 4H), 2.76-2.71 (m, 1H), 2.34 (dd, J=12.7, 6.3 Hz, 1H), 1.13 (d, J=6.5 Hz, 3H); $^{13}$C NMR (100 MHz, DMSO-d$_6$): δ 170.9, 164.8, 156.8 (ddd, J=244, 7.0, 2.5 Hz), 149.1 (ddd, J=249, 14.4, 8.5 Hz), 147.2 (ddd, J=246, 13.9, 3.2 Hz), 137.0, 133.5, 127.8, 125.4 (q, J=282 Hz), 123.3, 121.8, 119.7, 117.8 (dd, J=19.8, 13.8 Hz), 117.2 (dd, J=19.2, 10.6

Hz), 112.7, 112.3 (ddd, J=26.1, 6.7, 3.3 Hz), 105.1, 57.1, 51.3, 44.8 (q, J=32.7 Hz), 35.2, 26.9, 14.5.

N-((3S,5S,6R)-6-Methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate (28)

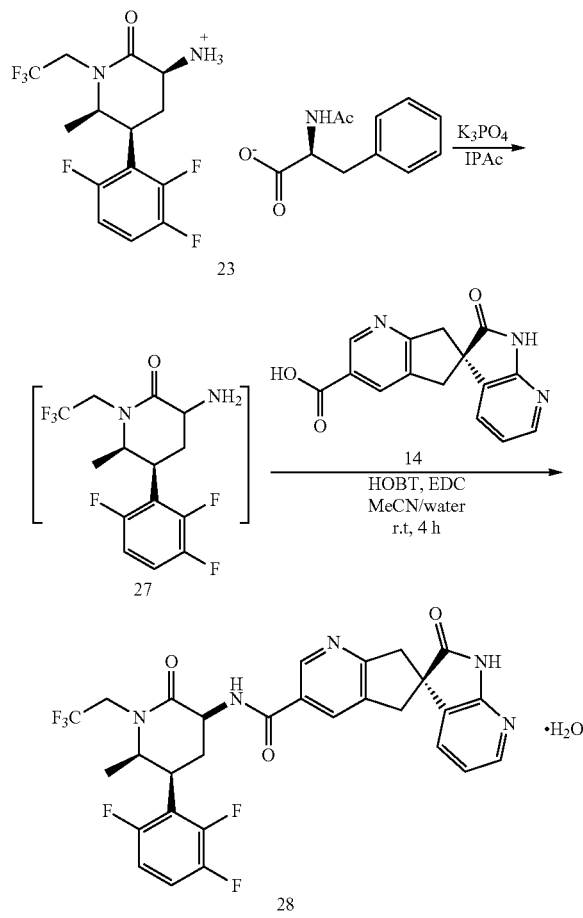

To a suspension of 23 (5.0 g, 9.1 mmol) in isopropyl acetate (50 mL) was added 5% aqueous $K_3PO_4$ (50 mL). The mixture was stirred for 5 min. The organic layer was separated and washed with aqueous $K_3PO_4$ (50 mL). Solvent removed under vacuum and resulting oil (27) was dissolved in acetonitrile (20 mL). To another flask was added 14 (2.57 g), acetonitrile (40 mL), water (20 mL) and NaOH solution (10N, 0.9 mL). The solution of 27 in acetonitrile was charged to the mixture followed by HOBT monohydrate (1.5 g) and EDC hydrochloride (2.6 g). The mixture was agitated at room temperature for 4 h and HPLC analysis indicated a complete conversion. The reaction mixture was stirred with isopropyl acetate (60 mL) and the aqueous layer was removed. The organic layer was washed with 5% aqueous $NaHCO_3$ (40 mL) followed by a mixture of 15% aqueous citric acid (40 mL) and saturated aqueous NaCl (10 mL). The resulting organic layer was finally washed with 5% aqueous $NaHCO_3$ (40 mL). The solvent was removed under vacuum and the residue was dissolved in methanol (20 mL). The methanol solution was slowly charged into a mixture of water (50 mL) and methanol (5 mL) over 30 min with good agitation, followed by addition of water (50 mL) over 30 min. The suspension was stirred over night at room temperature. The mixture was filtered and crystals were dried in a vacuum oven for 5 h at 50° C. to give 28 (5.4 g, 95%) as monohydrate. $^1$H NMR (500 MHz, $CD_3OD$): δ 8.88 (t, J=1.2 Hz, 1H), 8.15 (t, J=1.2 Hz, 1H), 8.09 (dd, J=5.3, 1.5 Hz, 1H), 7.36 (dd, J=7.4, 1.5 Hz, 1H), 7.28 (qd, J=9.3, 4.7 Hz, 1H), 7.01 (tdd, J=9.7, 3.6, 1.9 Hz, 1H), 6.96 (dd, J=7.4, 5.3 Hz, 1H), 4.80 (dq, J=15.2, 9.2 Hz, 1H), 4.56 (dd, J=11.7, 6.8 Hz, 1H), 4.03 (ddd, J=13.6, 4.2, 2.6 Hz, 1H), 3.97-3.90 (m, 1H), 3.68 (dq, J=15.3, 8.8 Hz, 1H), 3.59 (t, J=16.2 Hz, 2H), 3.35 (d, J=4.4 Hz, 1H), 3.32 (d, J=3.5 Hz, 1H), 3.21 (qt, J=12.7, 3.1 Hz, 1H), 2.38-2.32 (m, 1H), 1.34 (d, J=6.5 Hz, 3H); $^{13}$C NMR (126 MHz, $CD_3OD$): δ 182.79, 171.48, 168.03, 166.71, 159.37 (ddd, J=244.1, 6.5, 2.1 Hz), 157.43, 150.88 (ddd, J=249.4, 14.4, 8.7 Hz), 148.96 (ddd, J=243.8, 13.7, 3.1 Hz), 148.67, 148.15, 136.84, 133.43, 131.63, 130.83, 130.48, 126.41 (q, J=280.0 Hz), 119.85, 118.89 (dd, J=19.0, 13.5 Hz), 117.77 (dd, J=19.8, 10.8 Hz), 112.80 (ddd, J=26.5, 6.5, 4.2 Hz), 58.86, 53.67, 52.87, 46.56 (q, J=33.3 Hz), 45.18, 42.06, 36.95, 27.76 (t, J=4.8 Hz), 14.11.

Example 3

3-Hydroxy-3-(2,3,6-trifluorophenyl)butan-2-one (30)

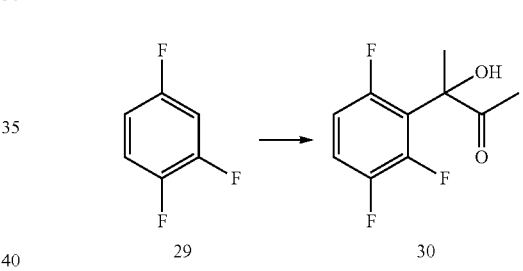

To a solution of 1,2,4-trifluorobenzene (29, 49.00 g, 371 mmol) and diisopropylamine (4.23 mL, 29.7 mmol) in THF (750 mL) at −70° C. was slowly added 2.5 M of n-BuLi (156.0 ml, 390 mmol) to maintain temperature between −45 to −40° C. The batch was agitated for 30 min. To another flask, a solution of 2,3-butadione (37.7 mL, 427 mmol) in THF (150 mL) was prepared and cooled to −70° C. The previously prepared lithium trifluorobenzene solution was transferred to the second flask between −70 to −45° C. The reaction was agitated for 1 hour at −55 to −45 and then quenched by adding AcOH (25.7 mL, 445 mmol) and then water (150 mL). After warmed to room temperature, the aqueous layer was separated. The aqueous solution was extracted with MTBE (200 mL×1) and the combined organic layers were washed with brine (100 mL×1). The organic layer was concentrated at 25-35° C. The residue was flashed with heptane (100 mL×1) and concentrated to dryness and give 30 (87.94 g, 90.2 wt %, 98% yield, and >99% HPLC purity) as an oil. $^1$H NMR ($CDCl_3$, 400 MHz): δ 7.16 (m, 1H), 6.86 (m, 1H), 6.88 (s, 1H), 4.59 (s, 1H), 2.22 (s, 3H), 1.84 (dd, J=4.0, 2.8 Hz, 3H); $^{19}$F NMR ($CDCl_3$, 376.6 MHz): δ −114.6 (dd, J=14.5, 1.4 Hz), −133.6 (d, J=19.9 Hz), −141.3 (dd, J=19.9, 14.5 Hz); $^{13}$C NMR ($CDCl_3$, 100 MHz): δ 207.4, 156.4 (ddd, J=247, 6.2, 2.9 Hz), 149.4 (ddd, J=253, 15.0, 9.0 Hz), 147.5 (ddd, J=245, 14.4, 3.3 Hz), 119.4 (dd, J=17.3, 11.7 Hz), 117.0 (ddd, J=19.3, 11.1, 1.4 Hz), 116.6 (ddd, J=26.6, 6.5, 4.1 Hz), 77.9, 25.0 (dd, J=6.5, 4.9 Hz), 23.3.

3-(2,3,6-Trifluorophenyl)but-3-en-2-one (31)

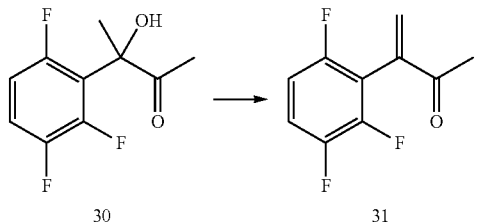

The hydroxy ketone 30 (7.69 g, 35.2 mmol) and 95% $H_2SO_4$ (26.2 mL, 492.8 mmol) were pumped at 2.3 and 9.2 mL/min respectively into the flow reactor. The temperature on mixing was controlled at 22-25° C. by placing the reactor in a water bath (21° C.). The effluent was quenched into a a mixture of cold water (106 g) and heptane/IPAc (1:1, 92 mL) in a jacketed reactor cooled at 0° C.; the internal temperature of the quench solution was ~7° C. during the reaction. The layers in the quench reactor were separated and the organic layer was washed with 10% $NaH_2PO_4/Na_2HPO_4$ (1:1, 50 mL). The pH of the final wash was 5-6. Solka flock (3.85 g, 50 wt %) was added to the organic solution. The resulting slurry was concentrated and solvent-switched to heptanes at 25-30° C. The mixture was filtered, rinsed with heptanes (50 mL×1). The combined filtrates were concentrated under vacuum to give 31 as an light yellow oil (6.86 g, 90 wt %, 87% yield), which solidified in a freezer. $^1$H NMR (CDCl$_3$, 400 MHz): δ 7.13 (m, 1H), 6.86 (m, 1H), 6.60 (s, 1H), 6.15 (s, 1H), 2.46 (s, 3H); $^{19}$F NMR (CDCl$_3$, 376.6 MHz): δ −117.7 (dd, J=15.0, 1.4 Hz), −135.4 (dd, J=21.4, 1.4 Hz), −42.7 (dd, J=21.4, 15.0 Hz); $^{13}$C NMR (CDCl$_3$, 100 MHz): δ 196.3, 155.3 (ddd, J=245, 5.1, 2.9 Hz), 147.9 (ddd, J=250, 14.5, 7.8 Hz), 147.0 (ddd, J=245, 13.4, 3.7 Hz), 137.5 (d, J=1.3 Hz), 131.7, 116.6 (ddd, J=19.9, 9.7, 1.2 Hz), 116.2 (dd, J=22.6, 16.5 Hz), 110.6 (ddd, J=24.8, 6.5, 4.1 Hz), 25.8.

Alternative synthesis of 3-(2,3,6-Trifluorophenyl)but-3-en-2-one (31)

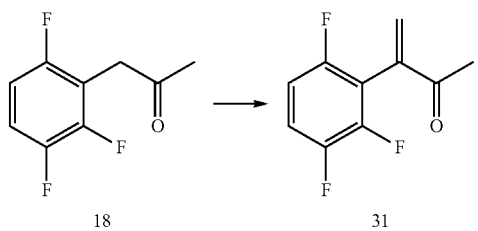

A solution of 18 (3.5 g, 18.6 mmol), acetic acid (0.34 ml, 5.58 mmol), piperidine (0.37 ml, 3.72 mmol), formaldehyde (6.0 g, 37% aqueous solution) in MeCN (20 mL) was heated over weekend. The conversion was about 60%. Reaction was heated to 70° C. overnight. The mixture was concentrated and extracted with MTBE and HCl (0.5N). The organic layer was washed with aqueous $K_2CO_3$ (0.5N) and water, in turns. The organic layer was concentrated. The product was isolated by chromatography column (hexane and EtOAc), yielding 31 (2.29 g, 61.5%).

Isopropyl 2-((diphenylmethylene)amino)-5-oxo-4-(2,3,6-trifluorophenyl)hexanoate (32)

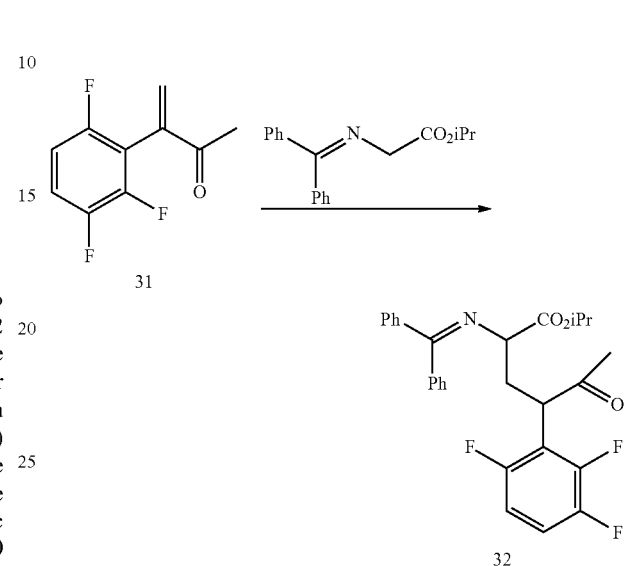

Diphenylidene isopropyl glycinate (2.0 g, 7.0 mmol) and 31 (1.4 g, 7.0 mmole) were dissolved in THF (10 ml). The solution was cooled to −10° C. tert-BuOLi (0.56 g, 7.0 mmole) was charged into the solution in several portions. The reaction was warmed up to room temperature slowly and stirred overnight. After quenched by addition of aqueous NH$_4$Cl, the solvents were removed by distillation under vacuum. The residue was subjected to silica chromatography column eluted by hexane and EtOAc yielding 32 (3.0 g, 89%) as an oil, which was directly used in the next step.

Isopropyl 2-((tert-butoxycarbonyl)amino)-5-oxo-4-(2,3,6-trifluorophenyl)hexanoate (19)

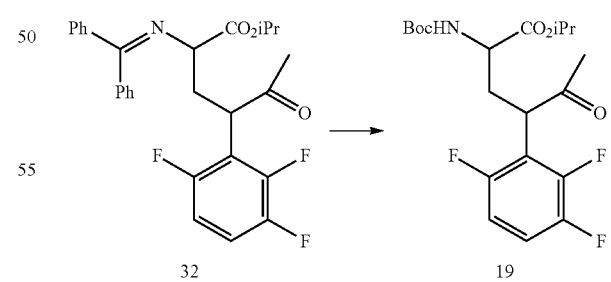

Compound 32 (100 mg, 0.21 mmol) was dissolved in THF (2 ml) and the solution was cooled to −10° C. Hydrochloric acid (2N, 1 ml) was added and stirred until all starting material disappeared by TLC. The pH of the reaction was adjusted (pH.>10) by addition of aqueous $K_2CO_3$. Boc$_2$O (68 mg, 0.31 mmole) was added into the mixture and stirred overnight. The reaction was completed checked by TLC and the product was identical to the one prepared from the iodo coupling route.

Isopropyl 2-((tert-butoxycarbonyl)amino)-5-oxo-4-(2,3,6-trifluorophenyl)hexanoate (19)

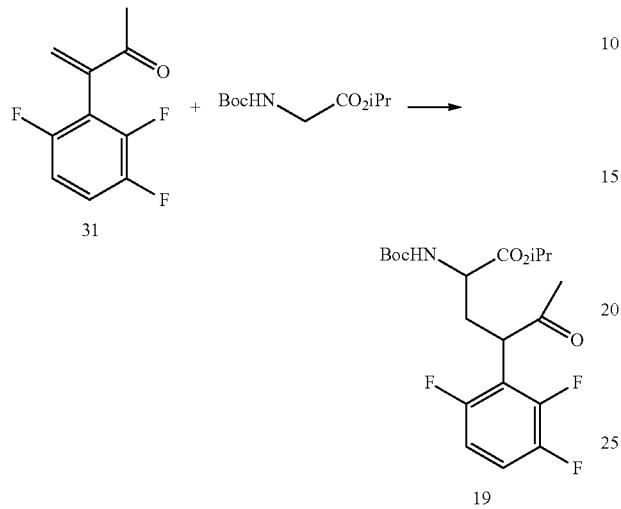

To a 100 mL round bottom was charged 2-methyl THF (43.7 mL) and diisopropyl amine (4.92 mL, 34.2 mmol) and the solution was cooled to −70° C. n-BuLi (13.08 mL, 32.7 mmol) was charged dropwise during which the temperature was controlled below −45° C. The mixture was stirred at −45° C. for 0.5 h. N-Boc-glycine ester (3.58 g) was added dropwise keeping temperature between −45 to −40° C. and aged at the same temperature for 1 h.

The solution of 31 (2.91 g, 14.5 mmol) in 2-methyl THF (2.9 mL) was then added dropwise in the same manner at −45 to −40° C. After a 0.5-1 h age, LC analysis showed nearly complete reaction. The reaction was quenched by addition of HOAc (3.83 mL) and the mixture was warmed to −10° C. and water (11.6 mL, 4 vol) was charged at <20° C. The phase was separated, and the organic layer was washed with 16% NaCl aqueous solution (11.6 mL). Assay desired product 19 as a mixture of diastereomers in the organic solution was 5.40 g (89% yield). The organic layer was concentrated to give crude product 19, which was directly used in the next step reaction. For characterization purposes, a small sample was purified by flash chromatography (silica gel, EtOAc/hexanes=1:10) to give two diastereomers 19A and 19B. 19A as a colorless oil, $^1$H NMR (CD$_3$CN, 400 MHz) δ: 7.29 (m, 1H), 7.02 (m, 1H), 5.58 (d, J=6.1 Hz, 1H), 4.91 (m, 1H), 4.19-4.05 (m, 2H), 2.79 (m, 1H), 2.05 (s, 3H), 1.84 (m, 1H), 1.41 (s, 9H), 1.23 (d, J=6.7 Hz, 3H), 1.22 (d, J=6.7 Hz, 3H); $^{13}$C NMR (CD$_3$CN, 100 MHz) δ: 204.7, 172.4, 158.6 (ddd, J=244, 6, 3 Hz), 156.3, 149.8 (ddd, J=248, 15, 9 Hz), 148.5 (ddd, J=242, 14, 3 Hz), 118.3 (dd, J=21, 16 Hz), 117.7 (ddd, J=19, 10, 2 Hz), 112.6 (ddd, J=26, 7, 4 Hz), 80.2, 70.0, 53.5, 46.0, 32.0, 28.5, 22.0, 21.9. 19B as colorless crystals, MP 91.5-92.0° C., $^1$H NMR (CD$_3$CN, 400 MHz) δ: 7.31 (m, 1H), 7.03 (m, 1H), 5.61 (d, J=8.2 Hz, 1H), 4.95 (m, 1H), 4.19 (dd, J=10.2, 5.1 Hz, 1H), 3.72 (m, 1H), 2.45-2.29 (m, 2H), 2.09 (s, 3H), 1.41 (s, 9H), 1.21 (d, J=6.3 Hz, 3H), 1.20 (d, J=6.3 Hz, 3H); $^{13}$C NMR (CD$_3$CN, 100 MHz) δ: 205.0, 172.8, 157.9 (ddd, J=244, 7, 3 Hz), 156.5, 150.3 (ddd, J=248, 149, 9 Hz), 148.5 (ddd, J=242, 13, 4 Hz), 117.9 (dd, J=19, 10 Hz), 115.9 (dd, J=21, 15 Hz), 111.5 (ddd, J=25, 8, 4 Hz), 80.1, 69.9, 52.9, 46.5, 31.1, 28.5, 22.0, 21.9.

Example 4

N-Methoxy-N-methyl-2-(o-tolyl)acetamide (34)

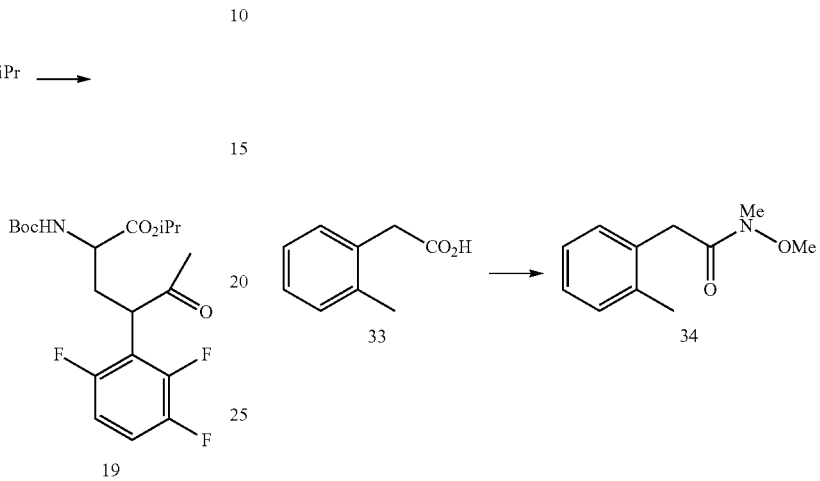

To a solution of NHMe(OMe).HCl (203 g, 2.1 mol) in THF (1 L), H$_2$O (400 mL) and TEA (263 g, 2.2 mol) was added 33 (200 g, 1.3 mol) and CDI (243 g, 1.5 mol) at 0-10° C. The reaction mixture was stirred at 0-10° C. for 5 h. After HPLC showed that the reaction was complete, the mixture was filtered through celite and the filtrate was partitioned with water and EtOAc. The organic solution was dried over Na$_2$SO$_4$ and concentrated. The crude residual was further purified by flash chromatography on silica gel (5-10% EtOAc/PE) to give 34 (200 g, 78% yield). $^1$H NMR (CDCl$_3$, 400 MHz): δ 7.17-7.13 (m, 4H), 3.75 (m, 2H), 3.66 (d, 3H), 3.11 (s, 3H), 2.20 (s, 3H), 1.63-1.55 (m, 1H); MS (ESI) m/e [M+H]$^+$: 194.1.

1-(o-Tolyl)propan-2-one (35)

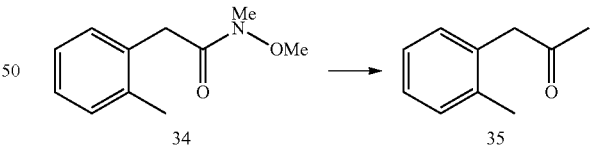

A solution of CeCl$_3$ (114.4 g, 0.45 mol) in THF (4 L) was degassed for 1 h and heated to 45-50° C. for 5 h. When the solution was cooled to −10~−5° C., MeMgCl (193.2 g, 2.6 mol) in THF was added and the mixture was stirred for 1 h at −10~−5° C. After amide 34 (256 g, 1.3 mol) was charged into the reaction mixture at −10~−5° C., the mixture was stirred for 5 h at 10-20° C. After the reaction was complete monitored by LCMS, the mixture was quenched by 1M HCl, and then partitioned with water and EtOAc. The organic phase was dried over Na$_2$SO$_4$ and concentrated. The crude residual was further purified by flash chromatography on silica gel (2-10% EtOAc/PE) to give 35 (157 g, 80% yield). $^1$H NMR (CDCl$_3$, 400 MHz): δ 7.1-6.91 (d, 4H), 3.55 (s, 3H), 2.25 (s, 3H), 2.05 (s, 3H); MS (ESI) m/e [M+H]$^+$: 149.05.

Isopropyl 2-((tert-butoxycarbonyl)amino)-5-oxo-4-(o-tolyl)hexanoate (36)

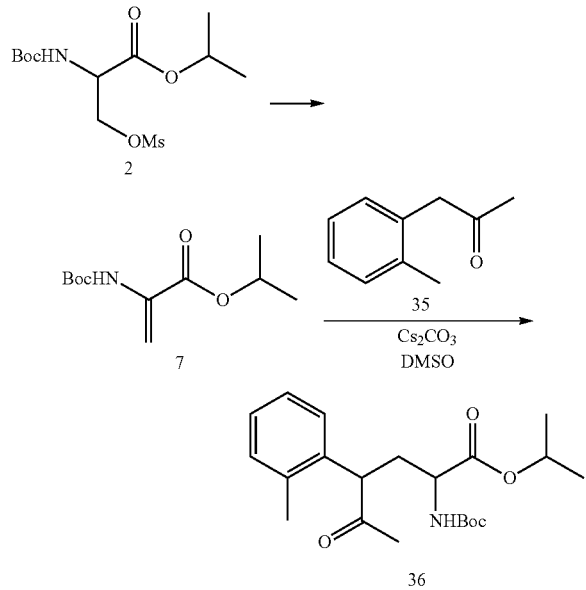

To a solution of 2 (181.2 g, 0.557 mol) in THF (1 L) was added TEA (84.6 g, 0.836 mol) in portions at 15-20° C. The mixture was stirred for 30 h. After the reaction was complete, the solution was concentrated to give crude 7. To a solution of 35 (82.5 g, 0.557 mol) and Cs$_2$CO$_3$ (91 g, 0.279 mol) in DMSO (1 L) was added slowly crude 7 in DMSO (500 mL) over 30 min at 15-20° C. The mixture was stirred for 1 h. After the reaction was complete, the mixture was partitioned with water and MTBE (5 L), and extracted with MTBE twice. The combined organic layer was dried over Na$_2$SO$_4$ and concentrated. The crude residual was further purified by flash chromatography on silica gel (5-10% EtOAc/PE) to give 36 (138 g, 65% yield).

$^1$H NMR (DMSO-d$_6$, 400 MHz): δ 7.14-7.09 (m, 3H), 7.10-6.91 (d, 1H), 4.93-4.89 (m, 1H), 4.05-3.98 (s, 3H), 2.39-2.37 (d, 3H), 1.98-1.92 (d, 3H), 1.20-1.19 (m, 9H), 1.18-1.15 (m, 6H); MS (ESI) m/e [M+H]$^+$: 364.2 tert-Butyl ((5S,6R)-6-methyl-2-oxo-5-(o-tolyl)piperidin-3-yl)carbamate (37)

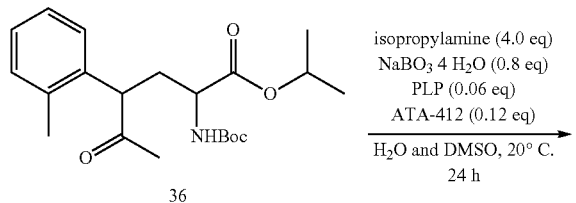

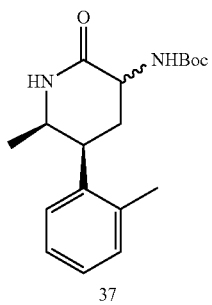

To a solution of NaBO$_3$.4H$_2$O (10 g, 0.026 mol) in H$_2$O (180 g) was charged isopropylamine (30 g, 0.25 mmol) dropwise at 20° C. After the mixture was stirred for 30 min, the pH was adjusted to 10.3-10.5 by 6M HCl. PLP (1 g, 6.4 mmol) and ATA-412 (25 g) was charged to the solution at 20° C. After the above mixture was stirred for 1 h, a solution of 36 (50 g, 4.7 mmoL) in DMSO (250 mL) was added slowly at 20° C. The solution was heated to 55° C. and stirred for 24 h. After the reaction was complete, the reaction was quenched by isopropyl alcohol (100 mL), and then partitioned with water and IPAc. The organic phase was dried over Na$_2$SO$_4$ and concentrated. The crude residual was further purified by flash chromatography on silica gel (5-20% EtOAc/PE) to give 37 (16.5 g, 40% yield). $^1$H (DMSO-d$_6$, 400 MHz): δ 7.83 (s, 1H), 7.18-7.13 (m, 4H), 4.06 (br, 1H), 3.67-3.51 (m, 2H), 2.30 (d, 3H), 1.99 (t, 1H), 1.36 (s, 9H), 0.82 (m, 3H); MS (ESI) m/e [M+H]$^+$: 319.2 tert-Butyl ((5S,6R)-6-methyl-2-oxo-5-(o-tolyl)-1-(2,2,2-trifluoroethyl)piperidin-3-yl)carbamate (38)

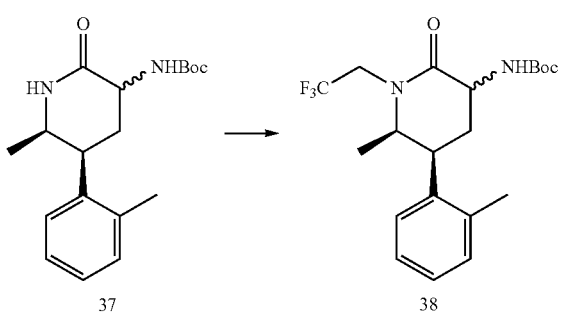 [SMILES: Cc1ccccc1[C@@H]1CC(NC(=O)OC(C)(C)C)C(=O)N[C@@H]1C ; Cc1ccccc1[C@@H]1CC(NC(=O)OC(C)(C)C)C(=O)N(CC(F)(F)F)[C@@H]1C]

To a solution of 37 (50 g, 0.164 mol) and DMPU (25 g, 0.2 mol) in THF (500 mL) was added tert-BuOLi (16.5 g, 0.2 mol) in portions at 20° C. for 0.5 h. After the mixture was degassed for 30 min at 20° C., CF$_3$CH$_2$OTf (45.8 g, 0.2 mol) was added at 20-25° C. The reaction was stirred for 24 h at 20-25° C. After the reaction was complete, the mixture was quenched by water, and then partitioned with water and EtOAc. The organic solution was dried over Na$_2$SO$_4$ and concentrated. The crude residual was further purified by flash chromatography on silica gel (2-10% EtOAc/PE) to give product 38 (50 g, 78% yield). $^1$H NMR (DMSO-d$_6$, 400 MHz): δ 7.18-7.13 (m, 4H), 4.17 (m, 1H), 4.11 (br, 1H), 3.67

(m, 3H), 2.66 (s, 1H), 2.33 (d, 3H), 1.83 (t, 1H), 1.41 (s, 9H), 0.96 (d, 3H); MS (ESI) m/e [M+H]+ 405.17.

(3S,5S,6R)-6-Methyl-2-oxo-5-(o-tolyl)-1-(2,2,2-trifluoroethyl)piperidin-3-aminium 4-methylbenzoate (39)

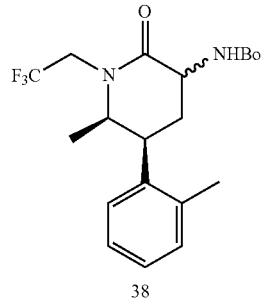

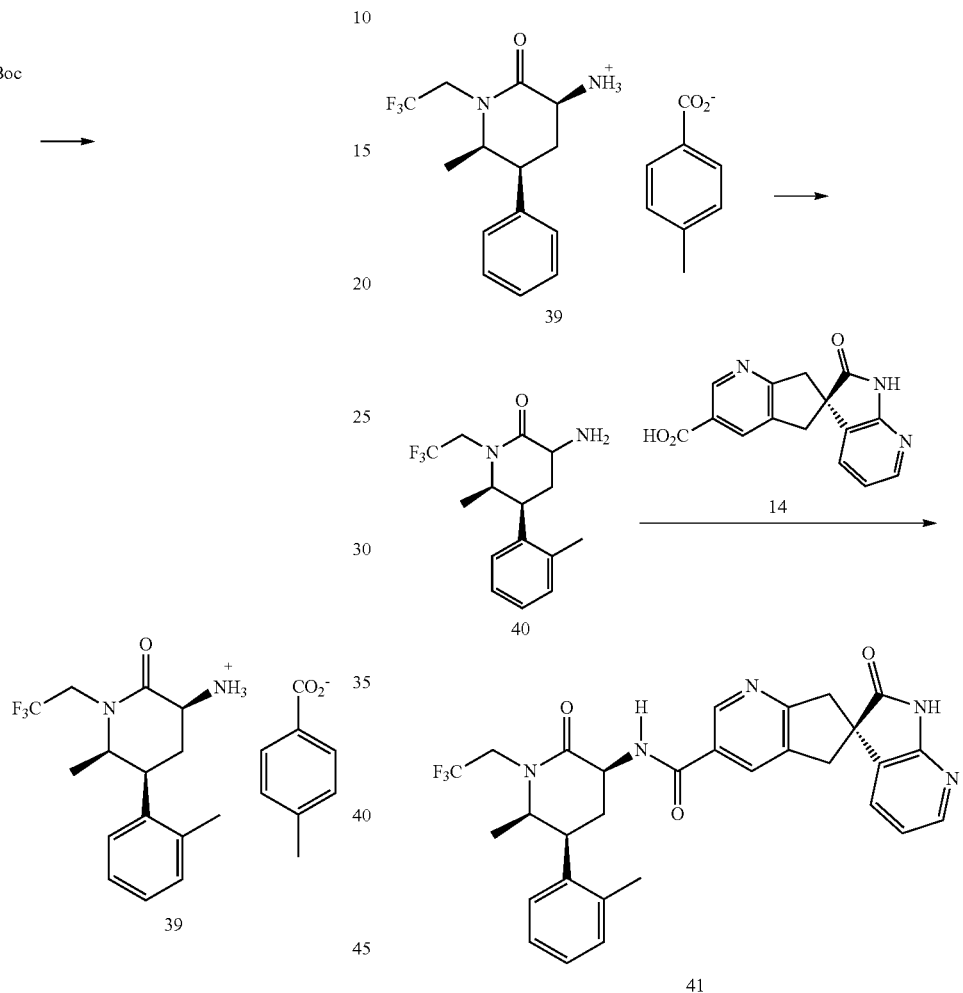

To a solution of 38 (2.0 g, 5.0 mol) in THF (10 mL) was added 6N HCl (10 mL, 59.9 mmol) dropwise. The reaction was aged at 20-25° C. for 5 h then concentrated to remove THF. The residue was diluted with MTBE and basified with K₂CO₃. A total of 3 mL of H₂O was added to dissolve all solids. The organic layer was separated, washed with brine, and solvent-switched to IPAC. To one-third of the organic layer was added 4-methylbenzoic acid (0.27 g, 2.00 mmol). The solution was heated to 50° C. and 2-hydroxy-5-nitrobenzaldehyde (0.0028 g, 0.017 mmol) was added. The reaction was aged at 20-25° C. for 16 h. The resulting slurry was chilled in an ice bath to 2° C. and filtered. The solids were washed with IPAC and dried to give product 39 (0.38 g, 52%) as crystals. ¹H NMR (500 MHz, DMSO-d₆): δ 7.82 (d, J=8.0 Hz, 2H), 7.26 (d, J=7.9 Hz, 2H), 7.18-7.19 (m, 3H), 7.12 (d, J=7.5 Hz, 1H), 4.67 (dq, J=15.2, 9.7 Hz, 1H), 3.72-3.74 (m, 2H), 3.61-3.63 (m, 1H), 3.55 (dd, J=11.3, 6.7 Hz, 1H), 2.40 (dd, J=25.2, 12.9 Hz, 1H), 2.35 (s, 3H), 2.32 (s, 3H), 2.02 (dd, J=12.6, 6.7 Hz, 1H), 0.91 (d, J=6.4 Hz; 3H); ¹³C NMR (100 MHz, DMSO-d₆): δ 172.7, 168.3, 142.4, 139.1, 136.1, 130.9, 130.5, 129.7, 129.3, 127.4, 127.2, 126.5, 125.6 (q, J=281 Hz), 56.2, 52.1, 45.0 (q, J=32.3 Hz), 38.5, 29.1, 21.5, 18.7, 14.2

(S)—N-((3S,5S,6R)-6-Methyl-2-oxo-5-(o-tolyl)-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide (41)

Salt 39 (0.25 g, 0.58 mmol) was partitioned between IPAC (2.5 mL) and 5 wt % aqueous solution of K₃PO₄ (2.5 mL), and washed twice with 5 wt % aqueous K₃PO₄. The organic layer was washed with brine, dried over Na₂SO₄ and concentrated to give a crude 40. Crude 40 was dissolved in MeCN (1.75 mL) and H₂O (1.0 mL). To this was added acid 14 (0.17 g, 0.53 mmol), HOBT (0.11 g, 0.70 mmol) and EDC.HCl (0.17 g, 0.87 mmol). The heterogeneous mixture was aged at 20-25° C. for 16 h. The homogeneous reaction was partitioned between IPAC and saturated aqueous NaHCO₃, and washed twice with saturated aqueous NaHCO₃. The organic layer was washed with 15 wt % aqueous citric acid solution, saturated aqueous NaHCO₃ and brine. The organic layer was dried over Na₂SO₄ and concentrated to give product 41 (0.29 g, 89% yield). ¹H NMR (400 MHz, CD₃OD): δ 8.88 (d, J=1.9 Hz, 1H), 8.15 (d, J=1.9 Hz, 1H), 8.08 (dd, J=5.3, 1.6 Hz, 1H), 7.35 (dd, J=7.4, 1.6 Hz, 1H), 7.15-7.18 (m, 4H), 6.95 (dd, J=7.4, 5.3 Hz, 1H), 4.59 (dd, J=11.5, 7.0 Hz, 1H), 3.89-3.92 (m, 1H), 3.81 (dt, J=13.4, 3.2 Hz, 1H), 3.61-3.63 (m, 4H), 3.31-3.32 (m, 2H), 2.93-2.95 (m, 1H), 2.40 (s, 3H), 2.14-2.17 (m, 1H); 1.14 (d, J=6.5 Hz, 3H); $^1$H NMR (500 MHz, CDCl$_3$): δ 8.91 (s, 1H), 8.56 (s, 1H), 8.17 (dd, J=5.0, 1.5 Hz, 1H), 8.05 (s, 1H), 7.30 (d, J=5.0 Hz, 1H), 7.20 (m, 3H), 7.12 (m, 2H), 6.89 (dd, J=7.5, 5.0 Hz, 1H), 5.00-4.94 (m, 1H), 4.55 (m, 1H), 3.93-3.90 (m, 1H), 3.81-3.76 (m, 2H), 3.68 (d, J=16.5 Hz, 1H), 3.31-3.23 (m, 2H), 3.17 (d, J=16.5 Hz, 1H), 2.75-2.67 (m, 2H), 2.41 (s, 3H), 1.11 (d, J=6.5 Hz, 3H); $^{13}$C NMR (100 MHz, CD$_3$OD): δ 182.8, 171.8, 168.0, 166.7, 157.5, 148.7, 148.2, 139.5, 137.5, 136.8, 133.4, 132.0, 131.6, 130.8, 130.6, 128.4, 128.3, 127.4, 126.6 (q, J=283 Hz), 119.9, 58.1, 53.7, 53.0, 46.7 (q, J=33.4 Hz), 45.2, 42.1, 40.2, 28.8, 19.0, 13.6; HRMS: m/z=564.2219 (M+1), calculated m/z=564.2234 for C$_{30}$H$_{28}$F$_3$N$_5$O$_3$.

Example 5

N-Methoxy-N-methyl-2-(2,3,5-trifluorophenyl)acetamide (43)

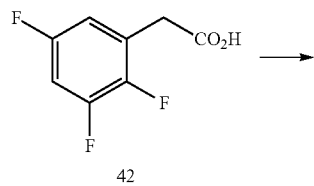

To a solution of NHMe(OMe).HCl (20.3 g, 0.21 mol) in THF (110 mL), H$_2$O (40 mL) and TEA (26.3 g, 0.22 mol) was added 2,3,5-trifluorophenylacetic acid (42, 24.7 g, 0.13 mol) and CDI (24.3 g, 0.15 mol) at 0-10° C. The reaction mixture was stirred at 0-10° C. for 5 h. After HPLC showed that the reaction was complete, the mixture was filtered through celite and the filtrate was partitioned with water and EtOAc. The organic solution was dried over Na$_2$SO$_4$ and concentrated. The crude residual was further purified by flash chromatography on silica gel (5-10% EtOAc/PE) to give 43 (24.0 g, 80% yield). $^1$H NMR (CDCl$_3$, 400 MHz): δ 6.76-6.72 (m, 2H), 3.72 (m, 2H), 3.66 (d, 3H), 3.15 (d, 3H); MS (ESI) m/e [M+H]$^+$: 234.07.

1-(2,3,5-Trifluorophenyl)propan-2-one (44)

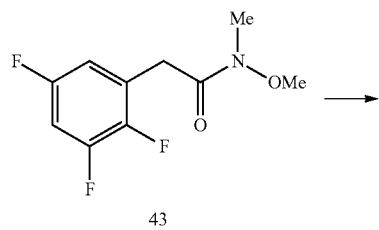

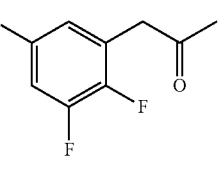

A solution of CeCl$_3$ (11.44 g, 0.045 mol) in THF (350 mL) was degassed for 1 h and heated to 45-50° C. for 5 h. When the solution was cooled to −10-5° C., MeMgCl (19.44 g, 0.26 mol) in THF was added and the mixture was stirred for 1 h at −10-5° C. After amide 43 (30.3 g, 0.13 mol) was charged into the reaction mixture at −10-5° C., the mixture was stirred for 5 h at 10-20° C. After the reaction was complete, the mixture was quenched by 1M HCl, and then partitioned with water and EtOAc. The organic phase was dried over Na$_2$SO$_4$ and concentrated. The crude residual was further purified by flash chromatography on silica gel (2-10% EtOAc/PE) to give 44 (20.8 g, 85% yield). $^1$H NMR (CDCl$_3$, 400 MHz): δ 6.91-6.78 (m, 1H), 6.69 (dd, 1H), 3.77 (d, 2H), 2.25 (s, 3H); MS (ESI) m/e [M+H]$^+$: 189.05.

Isopropyl 2-((tert-butoxycarbonyl)amino)-5-oxo-4-(2,3,5-trifluorophenyl)hexanoate (45)

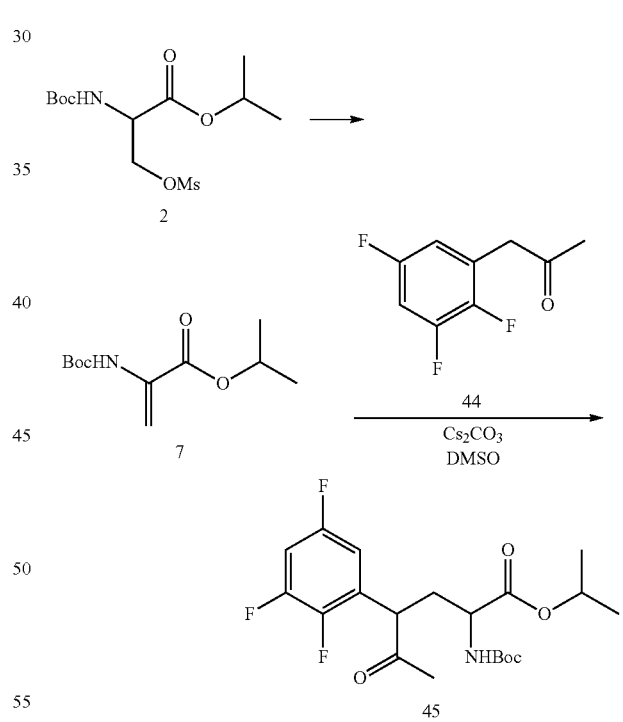

To a solution of 2 (10.98 g, 33.7 mmol) in THF (50 mL) was added TEA (4.8 g, 47.4 mmol) in portions at 15-20° C. The mixture was stirred for 30 h. After the reaction was complete, the solution was concentrated to give crude 7. To a solution of 44 (6.3 g, 33.7 mmol) and Cs$_2$CO$_3$ (5.0 g, 15.3 mmol) in DMSO (35 mL) was added slowly crude 7 in DMSO (35 mL) over 30 min at 15-20° C. The mixture was stirred for 1 h. After the reaction was complete, the mixture was partitioned with water and MTBE (50 mL) and extracted twice by MTBE. The combined organic layer was dried over Na$_2$SO$_4$ and concentrated. The crude residual was further purified by flash chromatography on silica gel (5-10% EtOAc/PE) to 45 (8.4 g, 60% yield). ¹H NMR (DMSO-d₆, 400 MHz): δ 6.77 (d, 1H), 6.59 (d, 1H), 5.11 (m, 1H), 4.93-4.89 (m, 1H), 4.12 (s, 2H), 2.66 (d, 1H), 2.05-2.01 (d, 3H), 1.38 (m, 9H), 1.18-1.15 (m, 6H); MS (ESI) m/e [M+H]⁺: 418.18.

tert-Butyl ((5S,6R)-6-methyl-2-oxo-5-(2,3,5-trifluorophenyl)piperidin-3-yl)carbamate (46)

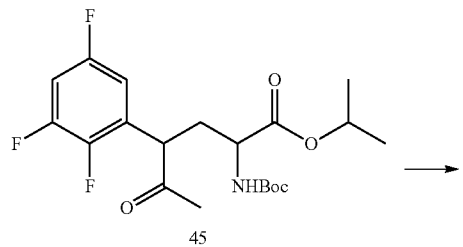

To a solution of NaBO₃.4H₂O (1.5 g, 3.9 mmol) in H₂O (18.2 g) was charged isopropylamine (1.16 g, 19.6 mmol) dropwise at 20° C. After the mixture was stirred for 30 min, the pH was adjusted to 10.2-10.3 by 6N HCl. PLP (0.042 g, 0.27 mmol) and ATA-412 (1.0 g) was charged to the solution at 20° C. After the above mixture was stirred for 1 h, a solution of 45 (2 g, 4.7 mmoL) in DMSO (10 mL) was added slowly at 20° C. The solution was heated to 55° C. and stirred for 24 h. After the reaction was complete, the reaction was quenched by isopropyl alcohol (10 mL), and then partitioned with water and IPAc. The organic solution was dried over Na₂SO₄ and concentrated. The crude residual was further purified by flash chromatography on silica gel (5-20% EtOAc/PE) to give 46 (1.45 g, 85% yield). ¹H NMR (DMSO-d₆, 400 MHz): δ 7.95-7.78 (m, 1H), 6.95 (m, 1H), 3.01 (t, 1H), 1.36 (s, 9H), 1.17-1.10 (br, 4H), 1.12 (m, 3H); MS (ESI) m/e [M+H]⁺: 359.15.

tert-Butyl ((5S,6R)-6-methyl-2-oxo-1-(2,2,2-trifluoroethyl)-5-(2,3,5-trifluorophenyl)piperidin-3-yl)carbamate (47)

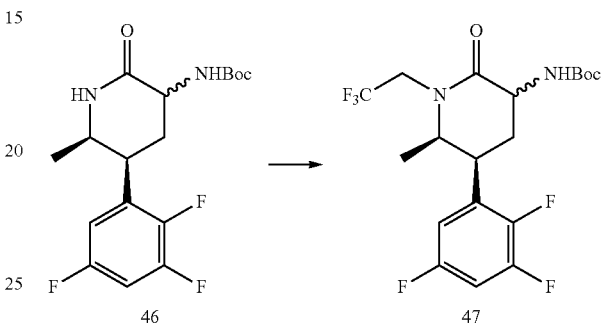

To a solution of 46 (50 g, 0.14 mol) and DMPU (7.2 g, 0.06 mol) in THF (500 mL) was added tert-BuOLi (8.6 g, 0.11 mol) in portions at 20° C. for 0.5 h. After the mixture was degassed for 30 min at 20° C., CF₃CH₂OTf (37.5 g, 0.14 mol) was added at 20-25° C. The solution was stirred for 24 h at 20-25° C. After the reaction was complete, the mixture was quenched by water, and then partitioned with water and EtOAc. The organic solution was dried over Na₂SO₄ and concentrated. The crude residual was further purified by flash chromatography on silica gel (2-10% EtOAc/PE) to give product 47 (50 g, 82% yield). ¹H (DMSO-d₆, 400 MHz): δ 7.52 (m, 1H), 7.22-6.91 (m, 1H), 4.65 (m, 1H), 3.85 (br, 1H), 3.38-3.37 (m, 2H), 1.40 (s, 9H), 0.90 (m, 3H); MS (ESI) m/e [M+H]⁺: 441.15.

(5S,6R)-3-Amino-6-methyl-1-(2,2,2-trifluoroethyl)-5-(2,3,5-trifluorophenyl)piperidin-2-one (48)

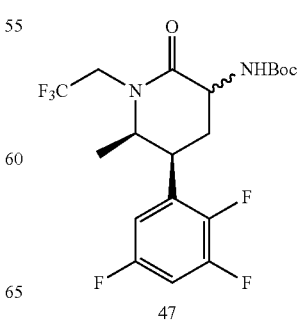

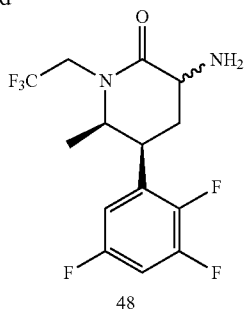

48

To a solution of 47 (2.0 g, 4.5 mmol) in IPAC (20 mL) was added p-toluenesulfonic acid monohydrate (1.3 g, 6.8 mmol). The mixture was aged at 55° C. for 4 h. After the reaction was complete, the slurry was cooled in an ice bath to 5° C. and a solution of potassium carbonate (1.9 g, 13.6 mmol) in H₂O (10 mL) was added. The aqueous layer (pH=10) was separated and the organic layer was washed with saturated aqueous NaHCO₃, water and brine, in turns, and dried over Na₂SO₄. Concentration afforded 48 (1.3 g, 86% yield) as a 4:1 mixture of diastereomers.

(3S,5S,6R)-3-Amino-6-methyl-1-(2,2,2-trifluoroethyl)-5-(2,3,5-trifluorophenyl)piperidin-2-one (S)-2-hydroxysuccinate (49)

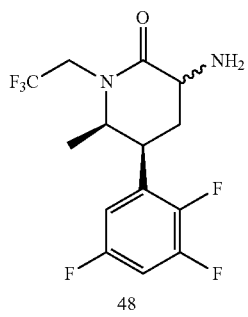

48

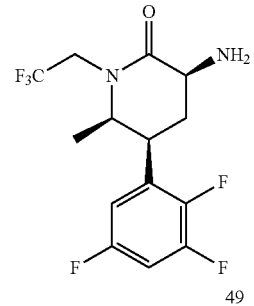

49

To a solution of 48 (0.24 g, 0.72 mmol) in THF (3.7 mL) was added L-(−)-malic acid (0.10 g, 0.75 mmol). The homogeneous reaction was heated to 58° C. and aged for 3 h. After the reaction was complete, the slurry was cooled to 20-25° C. and aged for 16 h. The solids were filtered, washed twice with ice-cold THF, and dried to give product 49 (0.25 g, 73% yield) as crystals. ¹H NMR (400 MHz, DMSO-d₆): δ 7.50-7.54 (m, 1H), 7.01-7.06 (m, 1H), 4.68 (dq, J=15.3, 9.6 Hz, 1H), 4.05 (dd, J=11.6, 6.7 Hz, 1H), 3.91-3.92 (m, 2H), 3.84-3.87 (m, 2H), 2.51 (m, 1H), 2.45 (m, 1H), 2.33 (dd, J=15.6, 4.4 Hz, 1H), 2.15 (dd, J=12.3, 6.7 Hz, 1H), 0.97 (d, J=6.4 Hz, 3H);

¹³C NMR (100 MHz, DSMO-d₆): δ 176.3, 172.0, 168.4, 157.4 (ddd, J=243, 11, 2 Hz), 150.0 (dt, J=248, 14 Hz), 144.7 (ddd, J=242, 13, 4 Hz), 130.4 (dd, J=13, 9 Hz), 124.8 (q, J=281 Hz), 110.9 (dt, J=26, 3 Hz), 105.1 (dd, J=28, 21 Hz), 66.1, 56.0, 49.6, 44.5 (q, J=33 Hz), 41.3, 35.1, 25.1, 13.8; ¹⁹F NMR (377 MHz, DMSO-d₆): δ −69.3, −114.6 (d, J=14.9 Hz), −134.7 (d, J=21.8 Hz), −148.8 (dd, J=21.8, 14.9 Hz).

(S)—N-((3S,5S,6R)-6-methyl-2-oxo-1-(2,2,2-trifluoroethyl)-5-(2,3,5-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide (51)

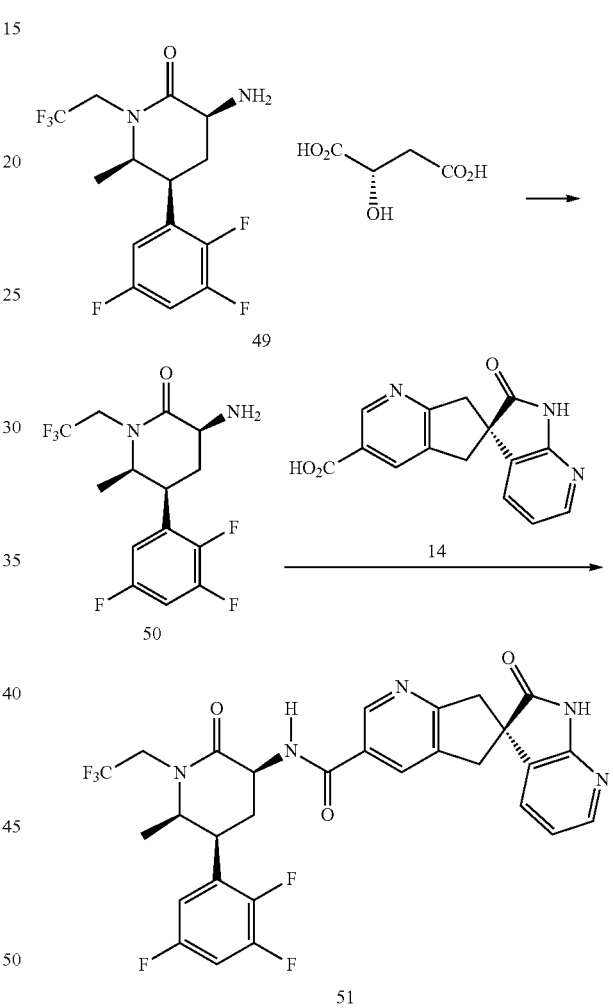

Salt 49 (0.60 g, 1.27 mmol) was partitioned in IPAC (6 mL) and a 5 wt % aqueous K₃PO₄ (6 mL), and washed twice with 5 wt % aqueous K₃PO₄. The organic layer was washed with brine, dried with Na₂SO₄ and concentrated to give crude 50. Crude 50 was then dissolved in MeCN (4.2 mL) and H₂O (2.4 mL). To this solution was added acid 14 (0.32 g, 1.12 mmol), HOBT (0.22 g, 1.42 mmol) and EDC.HCl (0.34 g, 1.77 mmol). The heterogeneous mixture was aged at 20-25° C. for 16 h. The reaction was partitioned between IPAC and saturated aqueous NaHCO₃, and washed twice with saturated aqueous NaHCO₃. The organic layer was then washed with 5 wt % aqueous citric acid, saturated aqueous NaHCO₃, and brine. The organic layer was dried over Na₂SO₄ and concentrated to give product 51. Compound 51 was crystallized from ethanol solution by addition of water. $^1$H NMR (500 MHz, CD$_3$OD): δ 9.15 (s, 1H), 8.82 (s, 1H), 8.22 (dd, J=6.1, 1.2 Hz, 1H), 8.13 (dd, J=7.3, 1.2 Hz, 1H), 7.37 (dd, J=7.3, 6.1 Hz, 1H), 7.16 (m, 1H), 6.94 (m, 1H), 4.79 (m, 1H), 4.67 (dd, J=11.5, 7.1 Hz, 1H), 4.06 (m, 1H), 4.01 (d, J=14.2 Hz, 1H), 3.90 (s, 2H), 3.79 (d, J=18.3 Hz, 1H), 3.73 (m, 1H), 3.69 (d, J=16.6 Hz, 1H), 2.89 (q, J=12.5 Hz, 1H), 2.28 (m, 1H), 1.20 (d, J=6.4 Hz, 3H); $^{13}$C NMR (400 MHz, CD$_3$OD): δ 182.8, 171.4, 168.1, 166.7, 159.6 (ddd, J=245, 10.5, 2.8 Hz), 157.5, 151.9 (dt, J=250, 14.2 Hz), 148.7, 148.2, 146.9 (ddd, J=243, 12.6, 3.9 Hz), 136.8, 133.4, 132.3 (dd, J=13.5, 8.5 Hz), 131.6, 130.8, 130.6, 126.4 (q, J=280 Hz), 119.8, 111.7 (bd, J=24.8 Hz), 105.7 (dd, J=28.1, 21.8 Hz), 69.2, 58.0, 53.7, 52.5, 46.7 (q, J=33.6 Hz), 45.2, 42.1, 37.5, 27.6, 13.7; $^{19}$F NMR (400 MHz, CD$_3$OD): δ −71.96, −116.67 (d, J=14.7 Hz), −136.41 (d, J=20.0 Hz), −150.47 (dd, J=19.5, 15.2 Hz); HRMS: m/z=604.1778 (M+1), calculated m/z=604.1778 for C$_{29}$H$_{24}$F$_6$N$_5$O$_3$.

Example 6

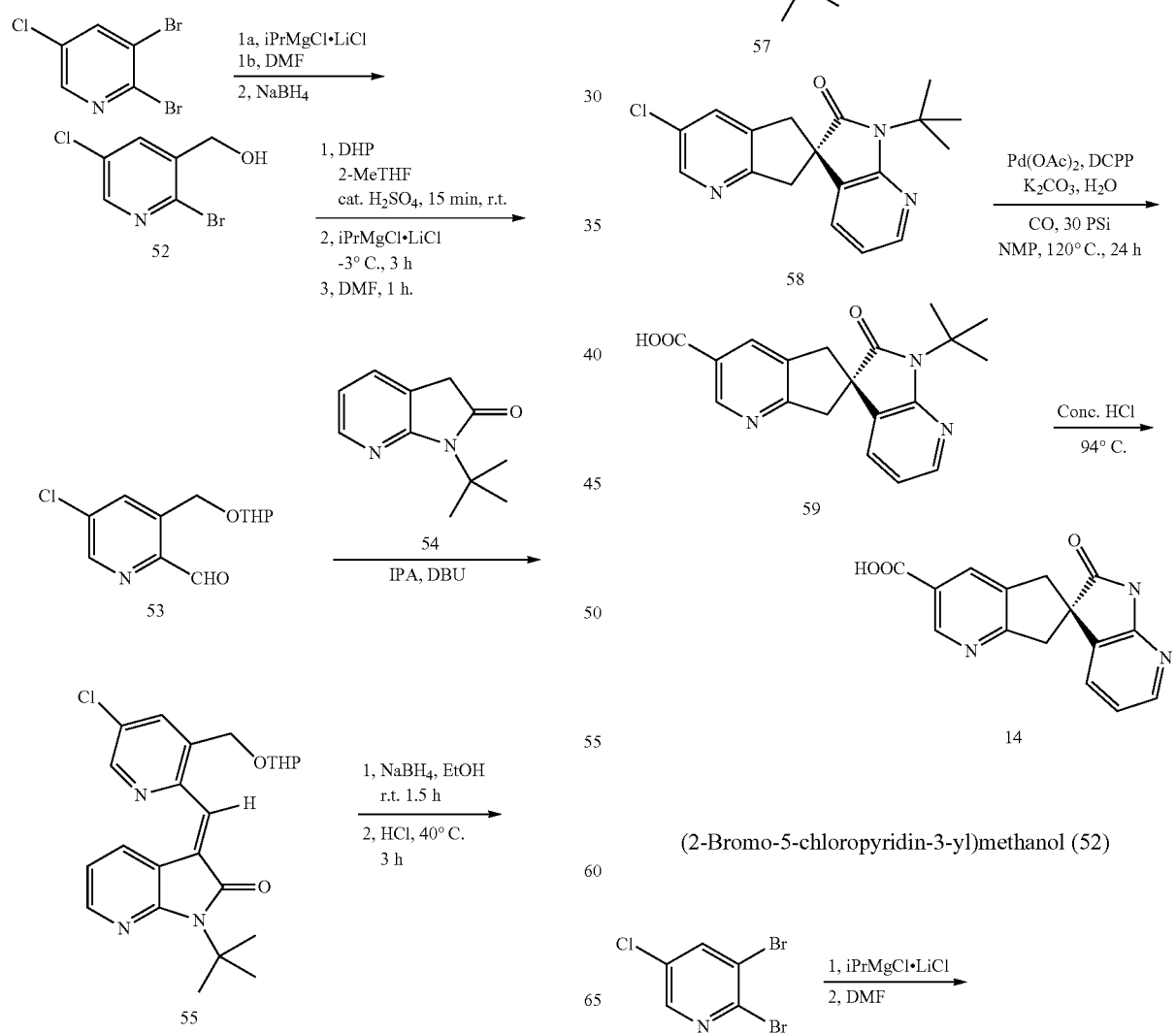

(2-Bromo-5-chloropyridin-3-yl)methanol (52)

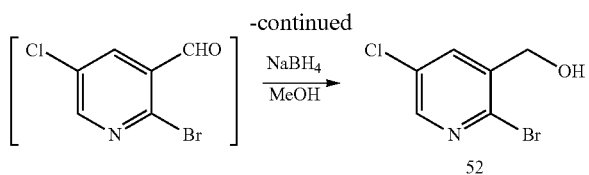

To a solution of 2,3-dibromo-5-chloropyridine (60 g, 221 mmol) in THF (500 mL) was added a solution of isopropylmagnesium chloride lithium chloride solution in THF (1.3M, 185 mL) at −40° C. over about 30 min. The solution was stirred for 30 min at −40° C. and DMF (50 mL) was added. The resulting solution was warmed up to room temperature and stirred for 30 min. The reaction was quenched with 1 N HCl (400 mL) and MTBE (200 mL) was added. Organic layer was separated and washed twice with 5% aqueous NaHCO$_3$ (200 mL). The solvent was removed under vacuum at 50° C. The resulting solids (aldehyde intermediate) were dissolved in methanol (400 mL). The solution was cooled to 5° C. under an ice bath. NaBH$_4$ (3.6 g) was added slowly over 30 min while maintaining the reaction temperature below room temperature. The reaction mixture was stirred for another 30 min followed by addition of water (125 mL). The resulting mixture was concentrated under vacuum to approximately 150 ml. Solids precipitated during the concentration. The suspension was stirred vigorously at room temperature for 1 h and solids were collected by filtration. The wet cake was dried in a vacuum oven over night at 60° C. to give 52 (45.6 g, 93%) as a solid. $^1$H NMR (CDCl$_3$, 400 MHz): δ 8.26 (d, J=2.5 Hz, 1H), 7.88 (d, J=2.5 Hz, 1H), 4.73 (d, J=5.8 Hz, 2H), 2.33 (t, J=11.4 Hz, 1H); $^{13}$C NMR (CDCl$_3$, 100 MHz): δ 147.12, 138.48, 138.39, 136.14, 132.06, 62.76.

5-Chloro-3-(((tetrahydro-2H-pyran-2-yl)oxy)methyl) picolinaldehyde (53)

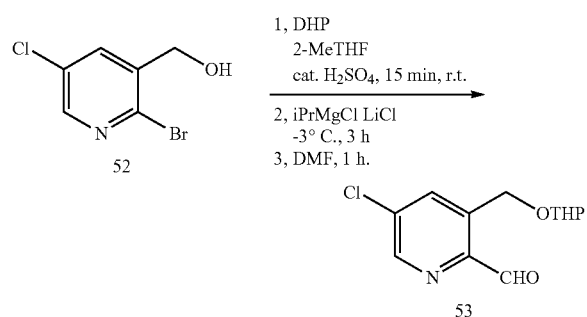

To a solution of 52 (5.0 g, 22.5 mmol) in 2-MeTHF (15 mL) was added 3,4-dihydro-2H-pyran (2.7 mL, 29.6 mmol) and concentrated sulfuric acid (125 mg) at room temperature. The solution was stirred for 10 min and was then cooled to −3° C. Isopropylmagnesium chloride lithium chloride solution (1.3 M, 30 ml, 39 mmol) was slowly added at −3 to 3° C. The resulting solution was stirred at −3° C. for 3 h until a HPLC showed the conversion was greater than 97%. DMF (5 ml) was added over 15 min below 5° C. The resulting solution was stirred for another 1 h at this temperature. The reaction mixture was quenched by addition of MTBE (50 mL), 15% aqueous citric acid (25 mL) and water (15 mL). The organic layer was separated and washed with 5% aqueous NaCl (50 mL) twice. The organic solution was concentrated under vacuum at 50° C. to give 53 as an oil (6.2 g, 68 wt %, 16.6 mmol, 74% yield). The crude product was used directly for the next step without further purification. The pure sample was isolated by flash chromatography on silica gel with 5% ethyl acetate in hexane as eluants. $^1$H NMR (CDCl$_3$, 400 MHz): δ 10.13 (s, 1H), 8.65 (s, 1H), 8.20 (s, 1H), 5.25 (d, J=16.6 Hz, 1H), 5.01 (d, J=16.6 Hz, 1H), 4.80 (m, 1H), 3.88 (m, 1H), 3.58 (m, 1H), 1.7 (m, 6H); $^{13}$C NMR (CDCl$_3$, 100 MHz): δ 194.20, 147.06, 146.32, 138.98, 136.41, 134.87, 99.04, 64.42, 62.72, 30.53, 25.30, 19.66.

(E)-1-(tert-Butyl)-3-((5-chloro-3-(((tetrahydro-2H-pyran-2-yl)oxy)methyl)pyridin-2-yl)methylene)-1H-pyrrolo[2,3-b]pyridin-2(3H)-one (55)

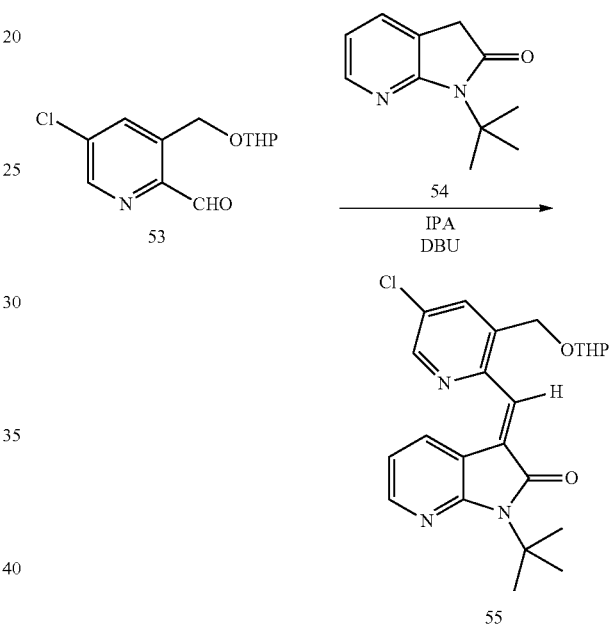

To a solution of crude 53 (6.2 g, 68 wt %, 16.6 mmol) and 54 (3.46 g, 18.3 mmol) in isopropanol (40 mL) was added DBU (0.12 g, 0.83 mmol) at −2° C. After stirring at −2° C. for 2 h, the solution was warmed up to 10° C. and stirred at this temperature for 3 h. The yellow solids precipitated from the solution. The suspension was stirred over night while the batch was allowed to warm up to room temperature slowly. The suspension was finally warm up to 50° C. and stirred for 4 h at this temperature. After cooling to 30° C., water (35 ml) was added dropwise over 30 min from an additional funnel. The suspension was cooled to room temperature and filtered. The cake was washed with a mixture of isopropanol (3 mL) and water (3 mL). The precipitates were collected and dried in a vacuum oven over night at 50° C. to give 55 (6.2 g, 87%) as a solid. $^1$H NMR (CDCl$_3$, 400 MHz): δ 8.72 (dd, J=7.5, 1.8 Hz), 8.66 (d, J=2.4 Hz, 1H), 8.18 (dd, J=5.1, 1.8 Hz, 1H), 7.94 (d, J=2.4 Hz, 1H), 7.78 (s, 1H, 1H), 6.89 (dd, J=7.5, 5.1 Hz, 1H), 4.99 (d, J=13.8 Hz, 1H), 4.80 (m, 1H), 4.70 (d, J=13.8 Hz, 1H), 3.90 (m, 1H), 3.60 (m, 1H), 1.83 (s, 9H), 2.0-1.5 (m, 6H). The conformation of the double bond as trans isomer was confirmed by NOE experiment. $^{13}$C NMR (CDCl$_3$, 100 MHz): δ 168.75, 159.64, 148.99, 147.85, 146.65, 137.01, 135.29, 133.56, 132.41, 129.50, 129.37, 117.27, 116.32, 98.77 64.80, 62.49, 58.62, 30.39, 29.01, 25.26, 19.34.

1-(tert-Butyl)-3-((5-chloro-3-(hydroxymethyl)pyridin-2-yl)methyl)-1H-pyrrolo[2,3-b]pyridin-2(3H)-one (56)

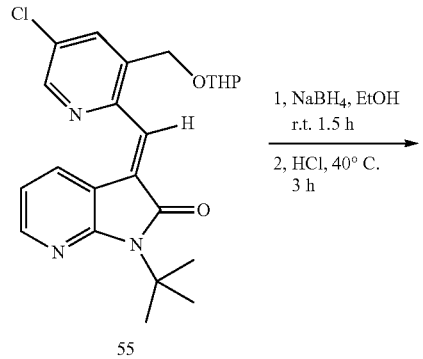

To a suspension of 55 (3.0 g, 7.0 mmol) in ethanol (25 mL) was added NaBH₄ (0.37 g) in one portion. The resulting suspension was stirred at room temperature for 1 h. The reaction was quenched by adding water (10 mL) followed by 6 N HCl solution in isopropanol (5 mL) slowly. The solution was warmed up to 40° C. and stirred for 3 h. The reaction mixture was mixed with MTBE (50 mL) and saturated aqueous NaCl (50 mL). The organic was separated and washed with water (50 mL). The solution was concentrated under vacuum at 50° C. and residue was triturated with hexane (30 mL). The resulting suspension was stirred at room temperature for 30 min. The precipitates were collected by filtration to give 56 (2.2 g, 86%) as a solid. ¹H NMR (CDCl₃, 400 MHz): δ 8.34 (s, 1H), 8.15 (d, J=4.9 Hz, 1H), 7.74 (s, 1H), 7.30 (d, J=7.1 Hz, 1H), 6.83 (t, J=5.7 Hz, 1H), 4.73 (dd, J=13.4, 4.9 Hz, 1H), 4.63 (dd, J=13.4, 5.7 Hz, 1H), 4.01 (t, J=6.1 Hz, 1H), 3.44 (dd, J=15.4, 5.2 Hz, 1H), 3.17 (dd, J=15.4, 7.2 Hz, 1H), 2.94 (t, J=5.5 Hz, 1H), 1.79 (s, 9H); ¹³C NMR (CDCl₃, 100 MHz): δ 178.72, 159.12, 153.82, 146.45, 145.83 135.72, 135.32, 130.63, 130.27, 124.04, 117.33, 61.40, 58.70, 44.12, 34.01, 28.81.

1-(tert-Butyl)-3-((5-chloro-3-(chloromethyl)pyridin-2-yl)methyl)-1H-pyrrolo[2,3-b]pyridin-2(3H)-one (57)

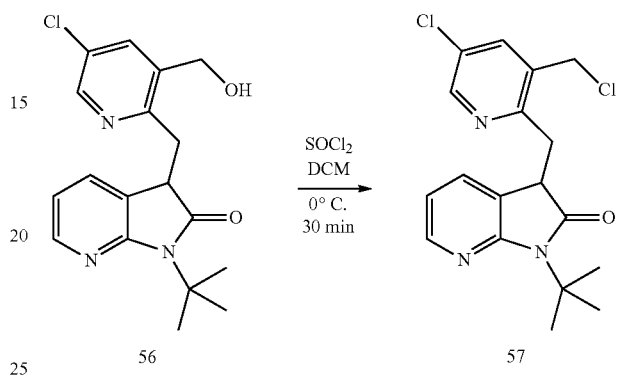

To a solution of 56 (5.8 g, 16.8 mmol) in dichloromethane (30 mL) was added DMF (60 µL) and thionyl chloride (2.2 g) at 5° C. The mixture was stirred for 30 min at this temperature followed by addition of 5% aqueous NaCl (30 mL). The organic layer was separated and washed with 5% aqueous NaCl (30 mL). The solvent was removed and the residue was dissolved in heptane (20 mL). The solution was stirred for 30 min and the product was precipitated. The suspension was cooled to 0° C. and filtered to give 57 (5.8 g, 93%) as a solid:
¹H NMR (CDCl₃, 400 MHz): δ 8.36 (d, J=2.3 Hz, 1H), 8.13 (dd, J=5.1, 1.4 Hz, 1H), 7.65 (d, J=2.3 Hz, 1H), 7.19 (om, 1H), 6.78 (dd, J=7.3, 5.2 Hz, 1H), 4.58 (m, 2H), 4.06 (m, 1H), 3.66 (dd, J=16.3, 4.6 Hz, 1H), 3.32 (dd, J=16.3, 7.5 Hz, 1H), 1.75 (s, 9H); ¹³C NMR (CDCl₃, 100 MHz): δ 178.06, 159.45, 154.58, 147.39, 145.73, 136.87, 132.47, 130.42, 130.11, 123.77, 117.03, 58.51, 43.37, 42.25, 33.69, 28.82.

(S)-1'-(tert-Butyl)-3-chloro-5,7-dihydrospiro[cyclopenta[b]pyridine-6,3'-pyrrolo[2,3-b]pyridin]-2'(1'H)-one (58)

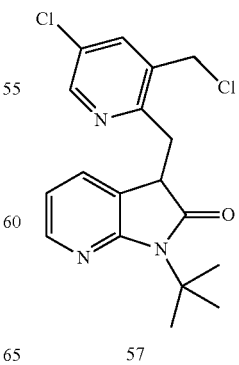

-continued

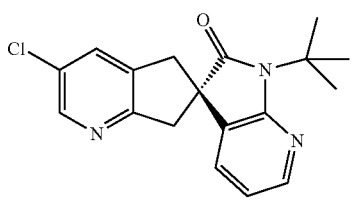

58

-continued

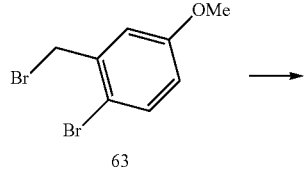

63

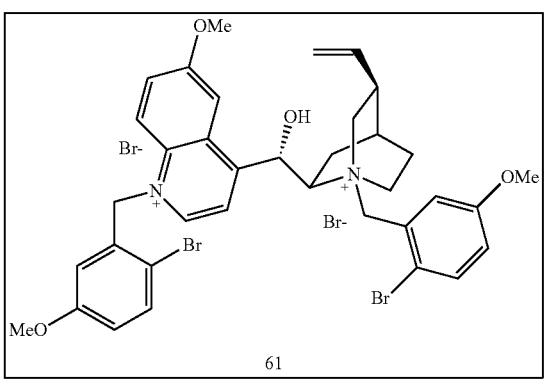

61

A solution of 57 (2.39 g, 6.56 mmol) in toluene (50 mL) was cooled to −2.5° C. under nitrogen atmosphere. Compound 61 (17 mg, 0.020 mmol) was charged, and the resulting solution was aged for about 15 min while cooled to −3.3° C. A pre-cooled (−1° C.). aqueous NaOH (26.2 mL, 0.3 N) was charged in over 4 min below −0.6° C. The reaction was aged at −1.3° C. for 3 h. The reaction was quenched with water (10 ml). The organic layer was washed with water (10 mL), concentrated, flushed with IPA to give crude product 58 (2.59 g, 94.4% ee, 83% wt by NMR against 1,3,5-trimethoxybenzene as an internal standard).

The crude product was recrystallized from IPA and water, filtered and dried in an oven at 50° C. to give 58 (1.95 g, 95.7% wt, 99% ee, 87% yield) as a solid. $^1$H NMR (CDCl$_3$, 400 MHz): δ 8.42 (s, 1H), 8.19 (d, J=5.2 Hz, 1H), 7.56 (s, 1H), 7.10 (d, J=7.3 Hz, 1H), 6.83 (dd, J=7.3, 5.2 Hz, 1H), 3.60 (dd, J=24.9, 16.8 Hz, 2H), 3.09 (dd, J=28.6, 16.8 Hz, 2H); $^{13}$C NMR (CDCl$_3$, 100 Hz): δ 179.43, 160.54, 157.82, 147.44, 146.54, 135.80, 132.17, 130.62, 129.33, 128.36, 117.69, 58.83, 51.94, 44.35, 41.57, 28.83.

(1S,2R,4S,5R)-1-(2-Bromo-5-methoxybenzyl)-2-((S)-(1-(2-bromo-5-methoxybenzyl)-6-methoxyquinolin-1-ium-4-yl)(hydroxy)methyl)-5-vinylquinuclidin-1-ium bromide (61)

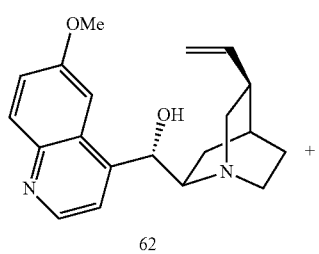

62

A slurry of quinidine (62, 8.1 g, 23.7 mmol, containing ~14% dihydroquinidine) and 2-bromo-5-methoxybenzylbromide (63, 16.59 g, 59.3 mmol) in IPA (4.0 ml) and DMF (28.4 mL) was degassed by vacuum and flushed with N$_2$, then heated to 70° C. for 7 h. The reaction mixture was cooled to 22° C., this reaction solution was charged to AcOEt (320 ml) at 22° C. over 10 min while stirring. The resulting slurry was aged at 22° C. for 1 to 2 h, filtered, rinsed with AcOEt (2×24 ml), then hexane (2×24 ml). The solid was dried under vacuum to give powder as a mixture of bis-salts (bis-quinidine salt 61 and bis-dihydroquinidine salt). (Total 19.7 g, 94% yield). The authentic sample of 61 was purified by SFC (IC column, 20×250 mm, 60% MeOH/CO$_2$, 50 mL/min, 100 bar, 35° C., 220 nm, sample concentration: 133 mg/mL in MeOH; desired peak: 3 to 4.5 min). $^1$H NMR (CDCl$_3$, 500 MHz): δ 9.34 (d, J=6.1 Hz, 1H), 8.46 (d, J=6.1 Hz, 1H), 8.38 (d, J=9.7 Hz, 1H), 8.0 (dd, J=9.7, 2.1 Hz, 1H), 7.86 (s, 1H), 7.79 (d, J=8.9 Hz, 1H), 7.74 (d, J=8.9 Hz, 1H), 7.60 (d, J=2.5 Hz, 1H), 7.42 (d, J=2.3 Hz, 1H), 7.17 (dd, J=8.8, 2.8 Hz, 1H), 7.03 (dd, J=8.8, 2.7 Hz, 1H), 6.93 (s, 1H), 6.50 (d, J=2.4 Hz, 1H), 6.06 (m, 1H), 5.24 (m, 3H), 4.95 (d, J=12.9 Hz, 1H), 4.37 (m, 1H), 4.23 (m, 4H), 4.12 (m, 1H), 3.88 (s, 3H), 3.69 (s, 3H), 3.54 (m, 1H), 3.32 (s, 2H), 3.23 (m, 1H), 2.71 (m, 1H), 2.51 (s, 2H), 2.33 (m, 1H), 1.94 (br, 1H), 1.83 (br, 2H), 1.17 (br, 1H); $^{13}$C NMR (DMSO-d$_6$, 100 Hz): δ 159.45, 159.07, 158.67, 156.12, 146.01, 137.08, 134.68, 134.30, 133.21, 132.98, 128.18, 128.03, 127.45, 122.13, 121.89, 121.22, 118.08, 117.5, 117.07, 116.73, 116.20, 115.81, 112.67, 105.09, 66.81, 65.51, 62.43, 56.75, 56.06, 55.91, 55.52, 54.80, 36.84, 25.91, 23.10, 20.75.

(S)-1'-(tert-Butyl)-2'-oxo-1',2',5,7-tetrahydrospiro[cyclopenta[b]pyridine-6,3'-pyrrolo[2,3-b]pyridine]-3-carboxylic acid (59)

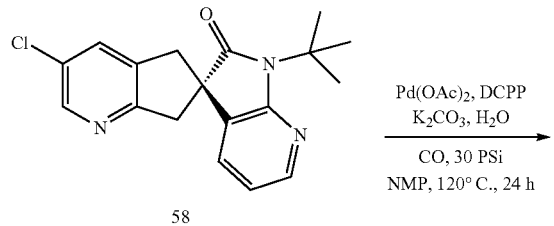

A mixture of 58 (5.0 g, 14.5 mmol), K$_2$CO$_3$ (5.01 g, 36.2 mmol), Pd(OAc)$_2$ (33 mg, 0.145 mmol), 1,3-bis(dicyclohexylphosphino)propane (DCPP, 127 mg, 0.290 mmol) and water (0.522 mL, 29.0 mmol) in NMP (32 mL) was heated at 120° C. under 30 psi of CO for 24 h. After cooling to room temperature, the resulting slurry was diluted with water (100 mL). The pH was slowly adjusted to 3-4 with 2 N HCl. The slurry was aged at room temperature for 1 h, filtered, rinsed with water (40 to 50 mL), dried under oven at 60° C. to give 59 (4.64 g, 95%) as a solid. $^1$H NMR (DMSO-d$_6$, 500 MHz): δ 8.90 (s, 1H), 8.19 (d, J=5.2 Hz, 1H), 7.54 (d, J=7.3 Hz, 1H,), 6.99 (dd, J=7.3, 5.2 Hz, 1H), 3.33 (m, 4H), 1.72 (s, 9H); $^{13}$C NMR (DMSO-d$_6$, 125 MHz): δ 180.16, 167.44, 166.97, 158.07, 149.76, 146.61, 135.39, 133.09, 130.36, 128.81, 125.48, 118.44, 58.19, 51.12, 44.56, 41.24, 28.91.

(S)-2'-Oxo-1',2',5,7-tetrahydrospiro[cyclopenta[b]pyridine-6,3'-pyrrolo[2,3-b]pyridine]-3-carboxylic acid (14)

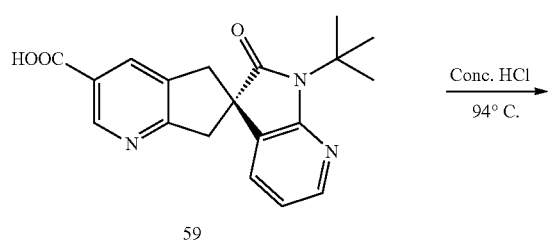

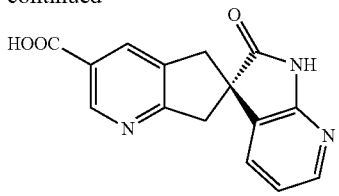

To 59 (4 g, 97% wt) was charged 37% HCl (40 to 44 mL). The slurry was heated at 94° C. for up to 48 h, cooled down to room temperature. The solvent was partially removed by reducing pressure to about total 2 vol (~4 mL water remained). The residue was diluted with water (20 mL) followed by adjusting pH to 2.6 with NaOH (3.5 N, 4.5 mL). The thick slurry was aged for 1 to 2 h, filtered, rinsed with water (2×8 mL), followed by water/acetone (1:1, 8 mL). The wet cake was dried to give compound 14 (3.1 g, 98% wt, 94%) as crystals. $^1$H NMR (DMSO-d$_6$, 500 MHz): δ 13.31 (br, 1H), 11.14 (s, 1H), 8.91 (s, 1H), 8.11 (m, 2H), 7.49 (dd, J=7.3, 1.3 Hz, 1H), 6.93 (dd, J=7.3, 5, 3 Hz, 1H), 3.36 (m, 4H); $^{13}$C NMR (DMSO-d$_6$, 125 MHz): δ 181.06, 167.36, 166.95, 156.80, 149.79, 147.32, 135.37, 133.19, 130.73, 128.88, 125.50, 118.46, 51.78, 44.12, 40.70.

Example 7

1-(tert-Butyl)-1H-pyrrolo[2,3-b]pyridin-2(3H)-one (54)

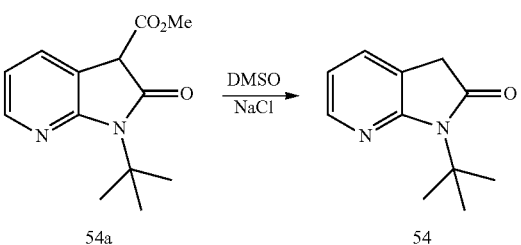

A mixture of compound 54a (10.0 g, 40.3 mmol), NaCl (2.9 g) and water (2 mL) in DMSO (50 mL) was heated at 120° C. for 30 min. The mixture was cooled to 30° C. followed by addition of MTBE (200 mL) and water (50 mL). The organic layer was separated and the aqueous layer extracted with another MTBE (50 mL). Combined organic layer was washed three times with water (50 mL). Solvent removed under vacuum and the resulting solid was dried in a vacuum oven at 30° C. to give 54 (7.0 g, 92%) as a solid. $^1$H NMR (CDCl$_3$, 400 MHz): δ 8.15 (dd, J=5.2, 1.4 Hz, 1H), 7.40 (dd, J=7.2, 1.4 Hz, 1H), 6.88 (dd, J=7.2, 5.2 Hz, 1H), 3.45 (s, 2H), 1.78 (s, 9H); $^{13}$C NMR (CDCl$_3$, 100 MHz): δ 174.99, 160.06, 145.82, 130.80, 119.51, 117.15, 58.53, 35.98, 28.80.

Example 8

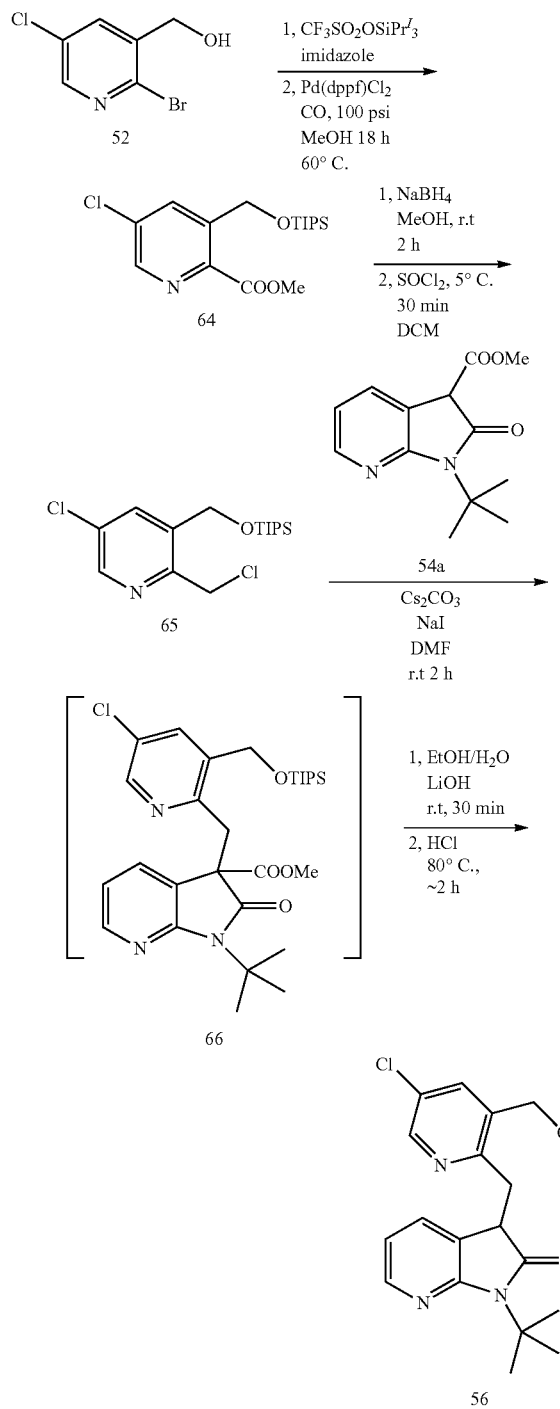

Methyl 5-chloro-3-(((triisopropylsilyl)oxy)methyl) picolinate (64)

To a solution of 52 (15.0 g, 67.4 mmol) in dichloromethane (60 mL) was added triisopropylsilyl trifluoromethanesulfonate (29.0 g, 94 mmol). The solution was cooled to 5° C. and imidazole (12.0 g, 176 mmol) was added in a few portions below 20° C. The reaction mixture was stirred at room temperature for 5 min and 5% brine (50 mL) was charged. The organic layer was separated and solvent removed under vacuum at 50° C. The resulting oil was dissolved in methanol (100 mL). The solution was kept under CO (100 psi) at 60° C. for 18 h in the presence of 5 mol % of Pd(dppf)Cl$_2$. The solvent was removed and the residue was transferred onto silica gel (60 g) on a filter funnel. The mixture was rinsed with a mixture of 10% ethyl acetate in hexane (400 mL). The resulting solution was concentrated to give crude 64 (29.2 g, 98% LCAP, 84% wt, 100% yield) as an oil, which was used directly in the next step without further purification. $^1$H NMR (CDCl$_3$, 400 MHz): δ 8.56 (d, J=2.4 Hz, 1H), 8.30 (d, J=2.4 Hz, 1H), 5.23 (s, 2H), 4.01 (s, 3H), 1.25 (m, 3H), 1.12 (d, J=6.8 Hz, 18H).

5-Chloro-2-(chloromethyl)-3-(((triisopropylsilyl) oxy)methyl)pyridine (65)

To a solution of crude 64 (29.2 g, 84 wt %, 67.4 mmol) in methanol (120 mL) was added NaBH$_4$ (11.6 g) portionwise over about 1 h at 5° C. The reaction mixture was quenched with water (150 mL) and the mixture was extracted with MTBE (150 mL). The organic solution was washed with water (100 mL). The solvent was removed under vacuum at 50° C. and the residue was dissolved in dichloromethane (60 mL). The solution was concentrated under vacuum at 60° C. The resulting residue was dissolved in dichloromethane (100 mL). The solution was cooled to 0° C. and DMF (0.5 g) was added followed by thionyl chloride (11.1 g) dropwise. The reaction mixture was then stirred for 30 min at 0° C. and quenched with 5% brine (100 mL). The organic layer was separated and washed with brine (100 mL). Solvent was removed under vacuum at 60° C. to give 65 as an oil (25 g, 92% LCAP, 70% wt, 72% yield), which was used in the next step without further purification. $^1$H NMR (CDCl$_3$, 400 MHz): δ 8.44 (d, J=2.4 Hz, 1H), 7.94 (d, J=2.4 Hz, 1H), 4.96 (s, 2H), 4.65 (s, 2H), 1.22 (m, 3H), 1.12 (d, J=6.7 Hz, 18H).

1-(tert-Butyl)-3-((5-chloro-3-(hydroxymethyl)pyridin-2-yl)methyl)-1H-pyrrolo[2,3-b]pyridin-2(3H)-one (56)

To a solution of 65 (8 g, 70% wt, 16.1 mmol) and 54a (4.15 g) of in DMF (30 mL) was added Cs$_2$CO$_3$ (5.76 g) and NaI (2.4 g). The mixture was stirred at room temperature for 1 h and the reaction mixture was mixed with MTBE (100 mL) and 15% aqueous citric acid (80 mL). The organic was washed with water (80 mL) twice and the solvent was removed. The residue (66, 90% LCAP) was dissolved in a mixture of ethanol (70 mL) and water (20 mL). After addition of LiOH (2.8 g), the solution was stirred for 30 min at room temperature. The reaction mixture was acidified with 6N HCl solution in IPA (17 mL). The resulting solution was heated at 80° C. for 2 h. After cooling to room temperature, the mixture was diluted with MTBE (100 mL) and 5% brine (50 mL). The organic layer was washed with water (50 mL) and dried over MgSO$_4$. The solution was concentrated under vacuum at 50°

C. and residue crystallized from hexane (30 mL), to give 56 (3.75 g, 67% from 65) as crystals.

Example 9

SCHEME

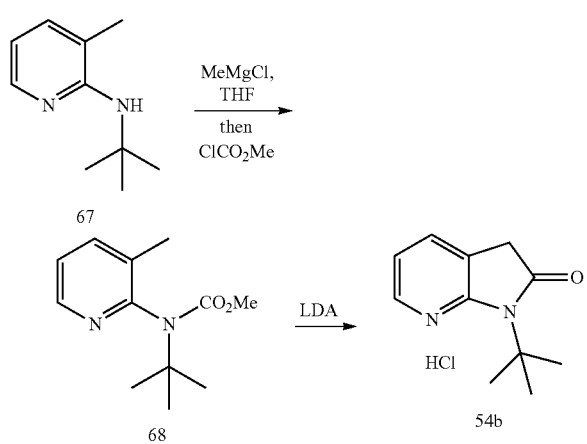

Methyl tert-butyl(3-methylpyridin-2-yl)carbamate (68)

To N-(tert-butyl)-3-methylpyridin-2-amine (67) (16.78 g, 92% wt, 102 mmol) in THF (100 ml) was addition MeMgCl (44.3 mL, 3M, 133 mmol) in THF under −10° C. over 5 min. The reaction mixture was warmed up to room temperature and aged for 80 min, then cooled to −20 to −15° C. and methyl chloroformate (8.7 ml, 112 mol) was added over 10 min under −8° C. The reaction mixture was gradually warmed up and aged overnight at room temperature. The reaction mixture was quenched by addition of 15% aqueous citric acid (13 mL), water (40 mL) and MTBE (33 mL) at 0° C. The organic layer was separated and washed with water (50 mL), saturated $NaHCO_3$/water (1:3, 50 ml), brine (50 mL) and water (50 mL), in turns. The organic layer was concentrated and flushed with THF to give 68 (19.3 g, 92%).

1-(tert-Butyl)-1H-pyrrolo[2,3-b]pyridin-2(3H)-one hydrochloride (54b)

Compound 68 (5 g, 97% wt, 21.8 mmol) in THF (30 ml) or toluene (50 ml) was degassed, cooled to −45° C. LDA (45.8 mL, 1.0 N) was added between −45 to −40° C. over 13 min. (Note: LDA was prepared separately in another flask by using 1.0 equiv n-BuLi and 1.1 equiv diisopropylamine in THF at −35° C. to 0 to 12° C., then cooled to 0° C.) The above reaction mixture was gradually warmed up to 13° C. over 4.5 h, cooled under an ice bath, and quenched with 2N HCl (~40 mL) (pH~4) and toluene (15 mL) below 20° C. The organic layer was separated and washed water (15 mL), brine (15 mL), and water (15 mL), in turns. The organic solution contained 54 (3.79 g, 91% assay yield) was concentrated, flushed with toluene to remove water. To a solution of the residue in toluene (7.6 mL), 2N HCl in ether (12 mL) was added over 30 min. To the mixture was added hexane (8 ml) and aged 1 h. The precipitates were filtered, rinsed toluene/hexane (1:2, 8 mL), then hexane (8 mL), and dried under vacuum with nitrogen stream to give salt 54b (3.92 g, 87%) as a solid. $^1H$ NMR ($CDCl_3$, 400 MHz): δ 11.9 (br, 1H), 8.13 (dd, J=5.2, 0.8 Hz, 1H), 7.54 (dd, J=7.2, 1.1 Hz, 1H), 6.96 (dd, J=7.2, 5.2 Hz, 1H), 3.52 (s, 2H), 1.69 (s, 9H); $^{13}C$ NMR (DMSO-$d_6$, 100 MHz): δ 174.99, 159.8, 145.67, 131.77, 120.54, 117.68, 57.89, 35.80, 28.99.

Example 10

SCHEME

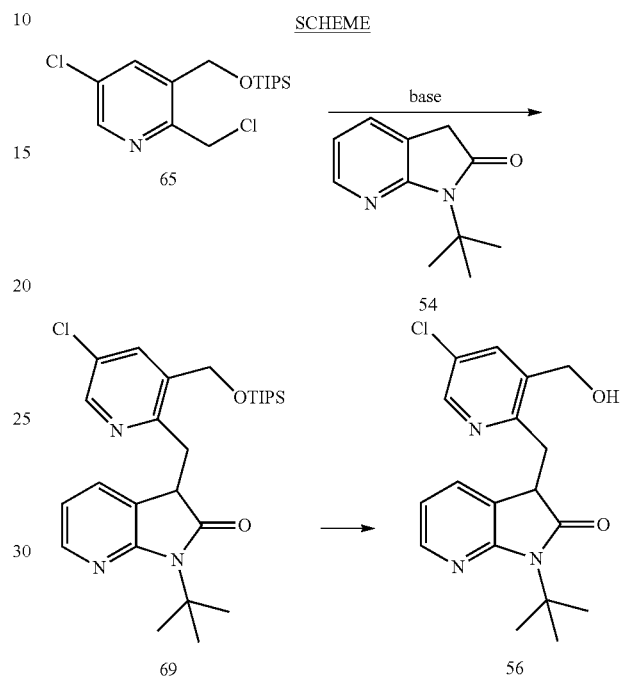

1-(tert-Butyl)-3-((5-chloro-3-(((triisopropylsilyl)oxy) methyl)pyridin-2-yl)methyl)-1H-pyrrolo[2,3-b]pyridin-2(3H)-one (69)

A solution of 65 (23.84 g, 60.7 mmol) and 54 (17.32 g, 91 mmol) in THF (200 ml) was degassed by vacuum/flush $N_2$ below 5° C. To the solution was added lithium amoxide solution in heptanes (27.4 mL, 40%, 85 mmol) maintaining below 7° C. The reaction was aged below 5° C. for 40 min, then quenched with saturated aqueous $NH_4Cl$ (10 mL), diluted with hexane (120 mL). The organic layer was separated, washed with saturated aqueous $NH_4Cl$ (100 mL) and water (150 mL), concentrated and purified by silica gel column (0 to 5% AcOEt/hexane) to obtain 69, which was used in the next reaction without further purification. HRMS m/z calcd. for $C_{28}H_{41}ClN_3O_2Si$ 502.2651 (M+H). found 502.2641

1-(tert-Butyl)-3-((5-chloro-3-(hydroxymethyl)pyridin-2-yl)methyl)-1H-pyrrolo[2,3-b]pyridin-2(3H)-one (56)

A solution of 69 (max 60.7 mmol) in THF (50 mL) obtained from the previous step was degassed with vacuum/flush $N_2$, cooled below 5° C. followed by charged TBAF (79 ml, 1.0 N in THF). The reaction aged at room temperature for 1 h 20 min, cooled below 10° C., quenched with water (100 ml), and diluted with AcOEt (200 mL). Aqueous layer was extracted with AcOEt (100 mL). The combined organic layer

Example 11

(S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide trihydrate 1.4 g of amorphous (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide freebase was slurried in 28 ml of 95:5 water:acetonitrile for 3 days, filtered and dried to yield ~1.1 g of the trihydrate.

Example 12

(S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol solvate 500 mg of (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide freebase monohydrate were dissolved in ~3.5 ml of MeOH and dissolved at 50° C. The solution was cooled to room temperature and allowed to cool and yielding crystalline MK-8031 Methanol solvate after about an hour.

Example 13

(S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide methanol water solvate 500 mg of (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide freebase monohydrate was slurried in 7:3 MeOH: water at room temperature for 3 days yielding crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide freebase methanol-water mixed solvate.

Example 14

(S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide acetonitrile water solvate To a mixture of 598 g (0.99 mol) of (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide trihydrate and 3.2 L of acetonitrile was added 0.8 L of water. The mixture was heated to 30° C. to dissolve all solids. The solution was cooled to 20° C. and 6 g of acetonitrile/water solvate seeds was introduced. After the mixture was stirred at 20° C. 30 minutes, 4 L of water was added slowly over 4 hours. During the addition of water solids precipitated as acetonitrile/water mixed solvate.

Example 15

(S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide acetonitrile solvate (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide trihydrate was dissolved in acetonitrile until solution until material gelled. White solids formed out of the gel and this was suspended in additional acetonitrile and stirred overnight yielding crystalline acetonitrile solvate.

Example 16

Amorphous (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide Drying of (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide acetonitrile-water solvate at 75° C. under vacuum for one hour yields an X-ray Amorphous Form.

Example 17

(S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide acetonitrile solvate (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate was slurried in acetonitrile for 3 days yielding solids of an acetonitrile solvate.

Example 18

(S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal To suspension of 500 mg of (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'-pyrrolo[2,3-b]pyridine]-3-carboxamide trihydrate in 5 mL of acetonitrile was added 5 mL of water slowly. ~2 mL of addition of water, it became homogeneous. 124 mg of L-tartaric acid was added and sonicated followed by stirring for 3 hours. Crystalline materials was filtered and dried overnight at 40° C. yielding crystalline (S)—N-((3S,5S,6R)-6-methyl-2-oxo-5-phenyl-1-(2,2,2-trifluoroethyl)piperidine-3-yl)-2'-oxo-1',2',5,7-tetrahydrospiro[cyclopenta[b]pyridine-6,3'- pyrrolo[2,3-b]pyridine]-3-carboxamide L-tartaric acid cocrystal form.

Example 19

(S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal 3 g of (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide monohydrate and 0.724 g of L-tartaric acid was slurried in 15 ml MIBK overnight yielding a thick suspension. 45 ml of additional MIBK was added and slurrying continued for another day. The solids were isolated and dried for 3 days under flowing nitrogen purge yielding crystalline (S)—N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide L-tartaric acid cocrystal form.

---

What is claimed is:

1. A process for making a compound of Formula I

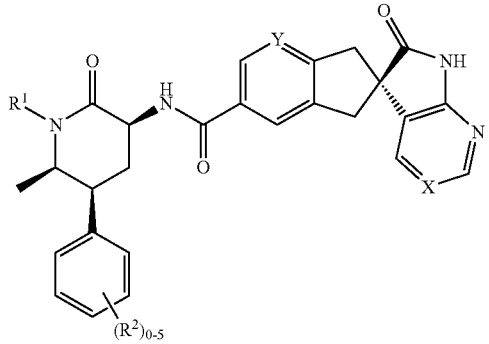

or a pharmaceutically acceptable salt thereof, wherein:
X is —C(R$^3$)═ or N—, wherein R$^3$ is hydrogen, F or CN;
Y is CH or N;
R$^1$ is: C$_{1-4}$alkyl, cyclopropylmethyl, cyclobutylmethyl, or [1-(trifluoromethyl)cyclopropyl]methyl, each of which may optionally be substituted with one or more substituents as allowed by valence, which are independently: F or hydroxy; and
R$^2$ is 0 to 5 substituents which are independently for each occurrence: methyl, F, Cl, or Br;
said process comprising crystallizing the compound of Formula A Formula A

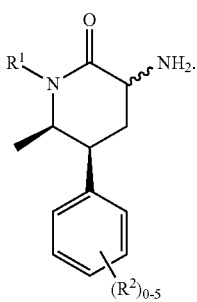

in the presence of an arylaldehyde derivative and a first acid in a first organic solvent to yield the compound of Formula B Formula B

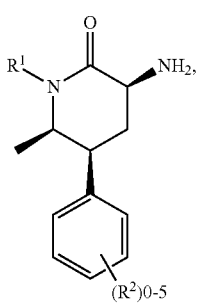

optionally as a salt, and coupling the compound of Formula B with a compound of Formula C Formula C

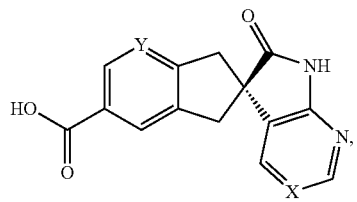

or a salt thereof, under conditions for an amide bond formation between an acid and an amine to yield a compound of Formula I.

2. The process according to claim 1 where the compound of Formula B is coupled with a compound of Formula C after salt break by reacting the reagents with an amide coupling reagent in a non-reactive solvent to yield a compound of Formula I.

3. The process according to claim 2 wherein the amide coupling regant is selected from the group consisting of EDC, HATU, T3P® and CDI, and the non-reactive solvent is an organic/aqueous mixture selected from the group consisting of DCM/water, iPAC/water, acetonitrile/water, acetone/water, iPA/water and THF/water.

4. The process according to claim 2 futher comprising an amide coupling reagent additive selected from the group consisting of HOBT and HOPO.

5. The process according to claim 1 wherein a salt of a compound of Formula C is coupled to the compound of Formula B.

6. The process according to claim 1 wherein the arylaldehyde derivative is selected from 2-hydroxybenzaldehyde, 2-hydroxy-5-nitrobenzaldehyde and 2-hydroxy-3,5-dichlorobenzaldehyde.

7. The process according to claim 1 further comprising making the compound of Formula A by reacting a compound of Formula D Formula D

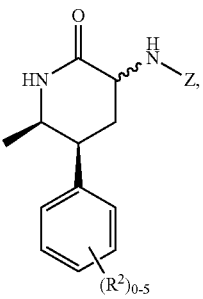

wherein Z is an amine protecting group, with an electrophilic alkylating agent that delivers a cationic R$^1$, in the presence of a base, optionally an additive in a second organic solvent and optionally salt additive to yield a compound of Formula E

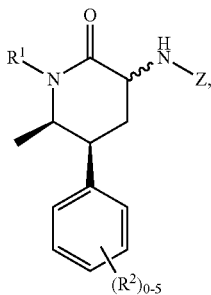

Formula E and deprotecting the compound of Formula E to yield a compound of Formula A.

8. The process according to claim 7 wherein the electrophilic alkylating agent is $R^1$—$OS(O)_2CF_3$ or $R^1$—$OS(O)_2F$, or $R^1$—$OS(O)_2R_F$, wherein $R_F$ is a polyfluorinated one to six membered carbon chain.

9. The process according to claim 8 wherein: Z is t-butyl-O—C(O)—, deprotection is effected by reacting the compound of Formula D with a second acid, the base is a lithium base, the additive is an aprotic polar solvent, and the second organic solvent is selected from the group consisting of THF, Me-THF and MTBE.

10. The process according to claim 9 wherein the lithium base is selected from the group consisting of LiOBut and LiOPent$^t$.

11. The process according to claim 9 wherein the second acid selected from the group consisting of HCl, MeSO$_3$H, H$_2$SO$_4$, p-toluenesulfonic acid and benzenesulfonic acid.

* * * * *